United States Patent
Nomura et al.

(10) Patent No.: US 8,313,845 B2
(45) Date of Patent: Nov. 20, 2012

(54) QUINOXALINE DERIVATIVE, AND LIGHT-EMITTING ELEMENT, LIGHT-EMITTING DEVICE, LIGHTING DEVICE, AND ELECTRONIC DEVICE USING QUINOXALINE DERIVATIVE

(75) Inventors: Hiroko Nomura, Fukuoka (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 207 days.

(21) Appl. No.: 12/748,859

(22) Filed: Mar. 29, 2010

(65) Prior Publication Data
US 2010/0244671 A1    Sep. 30, 2010

(30) Foreign Application Priority Data
Mar. 31, 2009    (JP) ................... 2009-085977

(51) Int. Cl.
*H01L 51/54* (2006.01)
*C07D 241/36* (2006.01)

(52) U.S. Cl. ........ 428/690; 428/917; 313/504; 313/506; 544/353

(58) Field of Classification Search .......... None
See application file for complete search history.

(56) References Cited

U.S. PATENT DOCUMENTS

| | | | |
|---|---|---|---|
| 6,541,129 B1 | 4/2003 | Kawamura et al. | |
| 7,601,435 B2 * | 10/2009 | Shitagaki et al. | 428/690 |
| 7,696,348 B2 * | 4/2010 | Egawa et al. | 544/353 |
| 8,008,489 B2 * | 8/2011 | Egawa et al. | 544/353 |
| 2002/0013427 A1 * | 1/2002 | Tsuji et al. | 525/523 |

(Continued)

FOREIGN PATENT DOCUMENTS

EP    1 029 909 A1    8/2000

(Continued)

OTHER PUBLICATIONS

Chemistry of Materials, (2002), 14(9), pp. 3852-3859.*

(Continued)

*Primary Examiner* — Dawn L. Garrett
(74) *Attorney, Agent, or Firm* — Husch Blackwell LLP

(57) ABSTRACT

A quinoxaline derivative represented by General Formula (G1) is provided. The quinoxaline derivative is bipolar and has excellent electron-transporting and hole-transporting properties. Also, the quinoxaline derivative has a high glass transition temperature and excellent thermal stability. By using the quinoxaline derivative, a light-emitting element and a light-emitting device with high efficiency can be obtained.

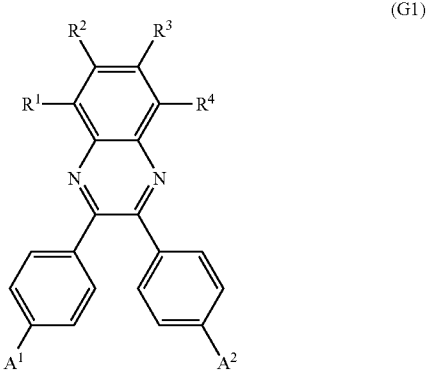

(G1)

17 Claims, 14 Drawing Sheets

U.S. PATENT DOCUMENTS

| | | |
|---|---|---|
| 2005/0186446 A1 | 8/2005 | Shitagaki et al. |
| 2005/0242715 A1 | 11/2005 | Inoue et al. |
| 2007/0059553 A1 | 3/2007 | Egawa et al. |
| 2007/0222374 A1 | 9/2007 | Egawa et al. |

FOREIGN PATENT DOCUMENTS

| | | |
|---|---|---|
| EP | 1 616 864 A1 | 1/2006 |
| JP | 2000-309566 | 11/2000 |
| WO | WO 2004/094389 A1 | 11/2004 |
| WO | WO 2005/054261 A1 | 6/2005 |

OTHER PUBLICATIONS

Advanced Functional Materials, (2006), 16(11), pp. 1449-1456.*

Tang, C.W. et al, "Organic Electroluminescent Diodes," Applied Physics Letters, vol. 51, No. 12, Sep. 21, 1987, pp. 913-915.

Adachi, C. et al, "Electroluminescence in Organic Films with Three-Layer Structure," Japanese Journal of Applied Physics, vol. 27, No. 2, Feb. 1988, pp. L269-L271.

Thomas, K.R.J. et al, "Quinoxalines Incorporating Triarylamines: Potential Electroluminescent Materials with Tunable Emission Characteristics," Chem. Mater., vol. 14, No. 6, May 3, 2002, pp. 2796-2802.

Huang et al, "Quinoxalines Incorporating Triarylamines: Dipolar Electroluminescent Materials with Tunable Emission Characteristics," Journal of the Chinese Chemical Society, 2006, vol. 53, No. 1, pp. 233-242.

* cited by examiner (HOMO)

(LUMO)

QUINOXALINE DERIVATIVE, AND
LIGHT-EMITTING ELEMENT,
LIGHT-EMITTING DEVICE, LIGHTING
DEVICE, AND ELECTRONIC DEVICE USING
QUINOXALINE DERIVATIVE

BACKGROUND OF THE INVENTION

1. Field of the Invention

The present invention relates to a quinoxaline derivative, and a light-emitting element, a light-emitting device, a lighting device, and an electronic device using the quinoxaline derivative.

2. Description of the Related Art

Organic compounds can have a wide variety of structures as compared with inorganic compounds, and have a possibility to provide materials with various functions by appropriate molecular design. Because of these advantages, photo electronics and electronics which use a functional organic material have been attracting attention in recent years.

As examples of electronic devices using an organic compound as a functional material, there are solar cells, light-emitting elements, organic transistors, and the like. These devices utilize electrical properties and optical properties of the organic compound. In particular, the light-emitting elements have been significantly developed.

It is considered that the light emission mechanism of a light-emitting element is as follows: when a voltage is applied between a pair of electrodes with a light-emitting layer interposed therebetween, electrons injected from the cathode and holes injected from the anode are recombined in the light emission center of the light-emitting layer to form molecular excitons, and energy is released and light is emitted when the molecular excitons relax to the ground state. A singlet excited state and a triplet excited state are known as the excited states, and it is thought that light emission can be obtained through either of the excited states.

Such a light-emitting element has a lot of problems that depend on the organic materials. In order to solve these problems, improvement of an element structure, development of a material, and the like have been carried out.

As the most basic structure of a light-emitting element, the following structure is known: a hole-transport layer formed of an organic compound with hole-transporting properties and an electron-transport light-emitting layer formed of an organic compound with electron-transporting properties are stacked to form a thin film with a total thickness of about 100 nm, and this thin film is interposed between electrodes (for example, see Reference 1).

When a voltage is applied to the light-emitting element described in Reference 1, light emission can be obtained from an organic compound having light-emitting and electron-transporting properties.

Furthermore, in the light-emitting element described in Reference 1, functions of the thin film are appropriately separated in such a manner that the hole-transport layer transports holes while the electron-transport layer transports electrons and emits light. However, various interactions (for example, exciplex formation) occur at the interface of stacked layers, which may cause a change in emission spectrum or a decrease in emission efficiency.

In order to suppress the change in emission spectrum and the decrease in emission efficiency that are caused by the interaction at the interface, a light-emitting element in which functions of the thin film are further separated has been developed. For example, a light-emitting element having such a structure that a light-emitting layer is sandwiched between a hole-transport layer and an electron-transport layer has been proposed (for example, see Reference 2).

REFERENCE

[Reference 1] C. W. Tang et al., *Applied Physics Letters*, vol. 51, No. 12, pp. 913-915 (1987)
[Reference 2] Chihaya Adachi et al., Japanese Journal of Applied Physics, vol. 27, No. 2, L269-L271 (1988)

SUMMARY OF THE INVENTION

It is an object of an embodiment of the present invention to provide a novel bipolar organic compound. It is an object of an embodiment of the present invention to provide a quinoxaline derivative with excellent thermal stability.

It is an object of an embodiment of the present invention to provide a light-emitting element and a light-emitting device with high efficiency by using the bipolar organic compound. It is also an object to provide a light-emitting element and a light-emitting device with a low driving voltage and low power consumption by using the bipolar organic compound of an embodiment of the present invention.

Furthermore, it is an object to provide an electronic device and a lighting device with a low driving voltage and low power consumption by using the bipolar organic compound of an embodiment of the present invention.

An embodiment of the present invention is a quinoxaline derivative represented by General Formula (G1).

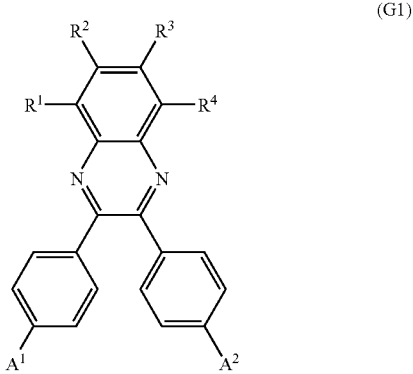

(G1)

In General Formula (G1), $R^1$ to $R^4$ each independently represent hydrogen, an alkyl group having 1 to 4 carbon atoms, or an aryl group having 6 to 10 carbon atoms in a ring. $A^1$ and $A^2$ each independently represent a hydrogen atom, an alkyl group having 1 to 4 carbon atoms, an aryl group having 6 to 10 carbon atoms in a ring, or a substituent represented by General Formula (A1) below. Note that at least one of $A^1$ and $A^2$ has the substituent represented by General Formula (A1).

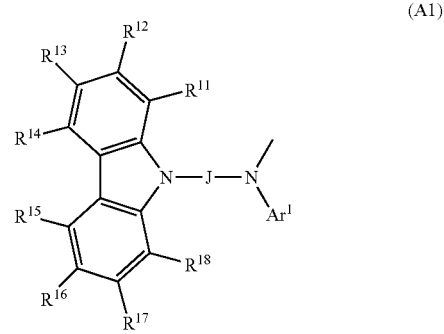

(A1)

In General Formula (A1), $Ar^1$ represents a substituted or unsubstituted heteroaryl group having 4 to 9 carbon atoms in a ring. Note that in the case where Ar¹ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring. J represents a substituted or unsubstituted arylene group having 6 to 12 carbon atoms. Note that in the case where J has a substituent, the substituent is an alkyl group having 1 to 4 carbon atoms.

Another embodiment of the present invention is a quinoxaline derivative represented by General Formula (G2).

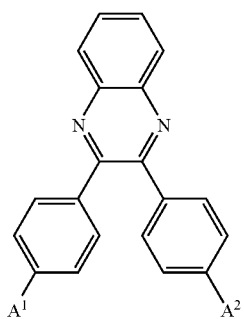

(G2)

In General Formula (G2), $A^1$ and $A^2$ each independently represent a hydrogen atom, an alkyl group having 1 to 4 carbon atoms, an aryl group having 6 to 10 carbon atoms in a ring, or a substituent represented by General Formula (A2). Note that at least one of $A^1$ and $A^2$ has the substituent represented by General Formula (A2) below.

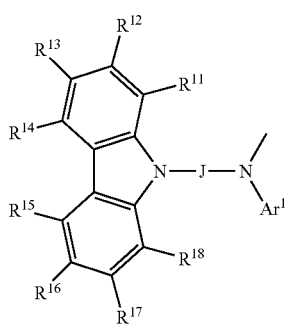

(A2)

In General Formula (A2), Ar¹ represents a substituted or unsubstituted heteroaryl group having 4 to 9 carbon atoms in a ring. Note that in the case where Ar¹ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring. J represents a substituted or unsubstituted arylene group having 6 to 12 carbon atoms. Note that in the case where J has a substituent, the substituent is an alkyl group having 1 to 4 carbon atoms.

Another embodiment of the present invention is a quinoxaline derivative represented by General Formula (G3).

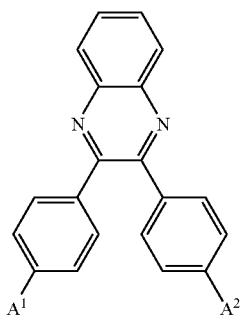

(G3)

In General Formula (G3), $A^1$ and $A^2$ each independently represent a hydrogen atom, an alkyl group having 1 to 4 carbon atoms, an aryl group having 6 to 10 carbon atoms in a ring, or a substituent represented by General Formula (A3) below. Note that at least one of $A^1$ and $A^2$ has the substituent represented by General Formula (A3).

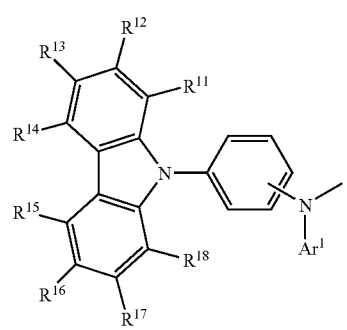

(A3)

In General Formula (A3), Ar¹ represents a substituted or unsubstituted heteroaryl group having 4 to 9 carbon atoms in a ring. Note that in the case where Ar¹ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring.

Another embodiment of the present invention is a quinoxaline derivative represented by General Formula (G4).

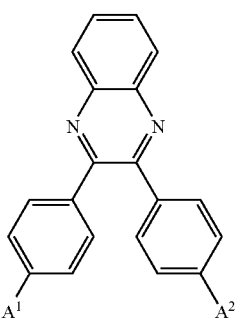

(G4)

In General Formula (G4), $A^1$ and $A^2$ each independently represent a hydrogen atom, an alkyl group having 1 to 4 carbon atoms, an aryl group having 6 to 10 carbon atoms in a ring, or a substituent represented by General Formula (A4) below. Note that at least one of A¹ and A² has the substituent represented by General Formula (A4).

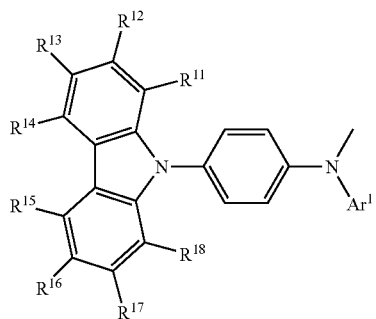

(A4)

In General Formula (A4), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring.

Another embodiment of the present invention is a quinoxaline derivative represented by General Formula (G5).

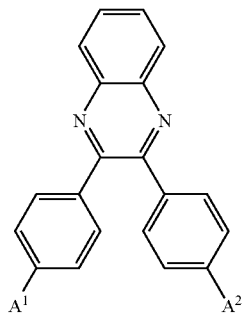

(G5)

In General Formula (G5), $A^1$ and $A^2$ each independently represent a hydrogen atom, an alkyl group having 1 to 4 carbon atoms, an aryl group having 6 to 10 carbon atoms in a ring, or a substituent represented by General Formula (A5) below. Note that at least one of $A^1$ and $A^2$ has the substituent represented by General Formula (A5).

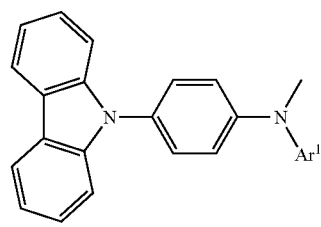

(A5)

In General Formula (A5), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring.

An embodiment of the present invention is a light-emitting element using any of the above quinoxaline derivatives. Specifically, an embodiment of the present invention is a light-emitting element including any of the above quinoxaline derivatives between a pair of electrodes.

Another embodiment of the present invention is a light-emitting element including any of the above quinoxaline derivatives in a light-emitting layer provided between a pair of electrodes.

Another embodiment of the present invention is a light-emitting element including any of the above quinoxaline derivatives and a substance which provides a fluorescent emission in a light-emitting layer provided between a pair of electrodes.

Another embodiment of the present invention is a light-emitting element including any of the above quinoxaline derivatives and a substance which provides a phosphorescent emission in a light-emitting layer provided between a pair of electrodes.

Another embodiment of the present invention is a light-emitting element having a light-emitting layer between a pair of electrodes and a layer including any of the above quinoxaline derivatives in contact with the light-emitting layer.

Another embodiment of the present invention is a light-emitting device having a light-emitting element including any of the above quinoxaline derivatives in a layer including a light-emitting substance provided between a pair of electrodes. Another embodiment of the present invention has a control unit configured to control light emission of a light-emitting element. Note that the term "light-emitting device" in this specification includes image display devices, light-emitting devices, and light sources (including lighting devices). In addition, the term "light-emitting devices" in this specification includes all types of modules such as follows: a module in which a connector, such as a flexible printed circuit (FPC), a tape automated bonding (TAB) tape, or a tape carrier package (TCP), is attached to a panel; a module in which a printed wiring board is provided at an end of a TAB tape or a TCP; and a module in which an integrated circuit (IC) is directly mounted on a light-emitting device by a chip-on-glass (COG) technique.

The present invention includes in its scope an electronic device including a light-emitting element of an embodiment of the present invention in a display portion. Thus, an embodiment of the present invention is an electronic device having a display portion which includes the above light-emitting element and a control means which controls light emission of the light-emitting element.

Another embodiment of the present invention is a lighting device formed with the use of a light-emitting device.

The quinoxaline derivative of an embodiment of the present invention is bipolar and has excellent electron-transporting and hole-transporting properties. In addition, the quinoxaline derivative of an embodiment of the present invention has a high glass transition temperature and excellent thermal stability.

Furthermore, by using the quinoxaline derivative of an embodiment of the present invention that is bipolar, a light-emitting element and a light-emitting device with a low driving voltage and low power consumption can be obtained. In addition, a light-emitting element with high emission efficiency can be obtained.

In addition, by using the quinoxaline derivative of an embodiment of the present invention that has a high glass transition temperature, a light-emitting element and a light-emitting device with high thermal stability can be obtained.

Further, by using the quinoxaline derivative of an embodiment of the present invention, an electronic device and a lighting device with low power consumption and a low driving voltage can be obtained.

DETAILED DESCRIPTION OF THE INVENTION

Figure 1:
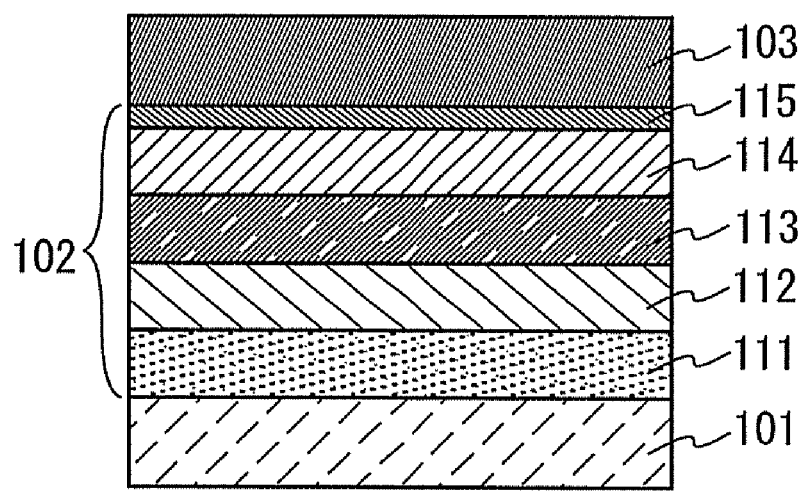
FIG. 1 illustrates a light-emitting element.

Embodiments of the present invention will be described below with reference to the drawings. Note that the present invention is not limited to the following description, and it is easily understood by those skilled in the art that modes and details of the present invention can be variously changed without departing from the spirit and the scope of the present invention. Therefore, the present invention should not be construed as being limited to the description of the following embodiments.

Embodiment 1

In this embodiment, a quinoxaline derivative of an embodiment of the present invention will be explained.

The quinoxaline derivative of an embodiment of the present invention is a quinoxaline derivative represented by General Formula (G1).

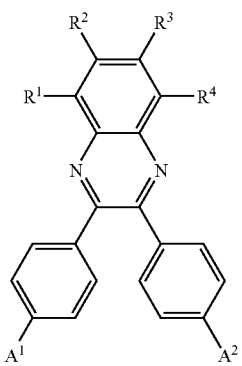

(G1)

In General Formula (G1), $R^1$ to $R^4$ each independently represent hydrogen, an alkyl group having 1 to 4 carbon atoms, or an aryl group having 6 to 10 carbon atoms in a ring. $A^1$ and $A^2$ each independently represent a hydrogen atom, an alkyl group having 1 to 4 carbon atoms, an aryl group having 6 to 10 carbon atoms in a ring, or a substituent represented by General Formula (A1) below. Note that at least one of $A^1$ and $A^2$ has the substituent represented by General Formula (A1).

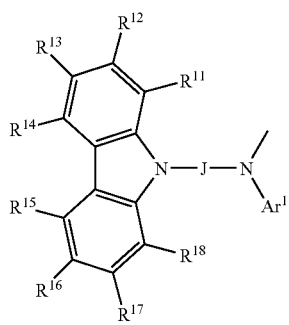

(A1)

In General Formula (A1), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring. J represents a substituted or unsubstituted arylene group having 6 to 12 carbon atoms. Note that in the case where J has a substituent, the substituent is an alkyl group having 1 to 4 carbon atoms. Note that the number of carbon atoms of an aryl group or an arylene group given in this specification refers to the number of carbon atoms which form a ring in the main skeleton and does not include the number of carbon atoms in a substituent which is bonded to the main skeleton.

Among quinoxaline derivatives represented by General Formula (G1), a quinoxaline derivative represented by General Formula (G2) is preferable because of its ease of synthesis and low material cost.

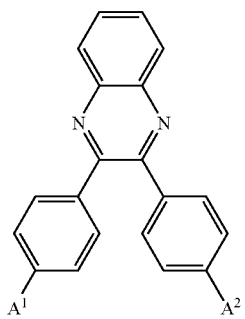
(G2)

In General Formula (G2), $A^1$ and $A^2$ each independently represent a hydrogen atom, an alkyl group having 1 to 4 carbon atoms, an aryl group having 6 to 10 carbon atoms in a ring, or a substituent represented by General Formula (A2) below. Note that at least one of $A^1$ and $A^2$ has the substituent represented by General Formula (A2).

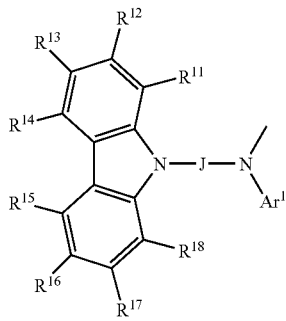
(A2)

In General Formula (A2), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring. J represents a substituted or unsubstituted arylene group having 6 to 12 carbon atoms. Note that in the case where J has a substituent, the substituent is an alkyl group having 1 to 4 carbon atoms.

Among the quinoxaline derivatives represented by General Formula (G1), a quinoxaline derivative represented by General Formula (G3) is preferable because of its ease of synthesis and high triplet level.

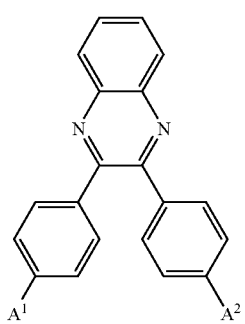
(G3)

In General Formula (G3), $A^1$ and $A^2$ each independently represent a hydrogen atom, an alkyl group having 1 to 4 carbon atoms, an aryl group having 6 to 10 carbon atoms in a ring, or a substituent represented by General Formula (A3) below. Note that at least one of $A^1$ and $A^2$ has the substituent represented by General Formula (A3).

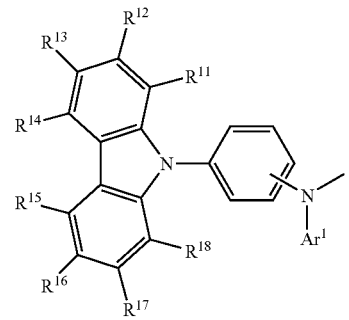
(A3)

In General Formula (A3), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring.

Furthermore, among the quinoxaline derivatives represented by General Formula (G1), a quinoxaline derivative represented by General Formula (G4) is preferable because of its ease of synthesis.

(G4)

[Structure of G4 - quinoxaline derivative]

In General Formula (G4), $A^1$ and $A^2$ each independently represent a hydrogen atom, an alkyl group having 1 to 4 carbon atoms, an aryl group having 6 to 10 carbon atoms in a ring, or a substituent represented by General Formula (A4) below. Note that at least one of $A^1$ and $A^2$ has the substituent represented by General Formula (A4).

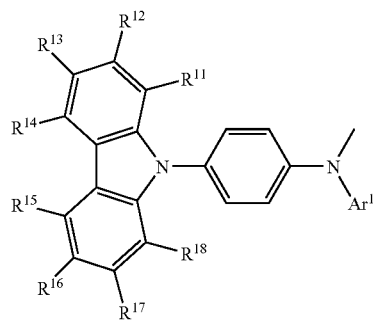
(A4)

In General Formula (A4), Ar$^1$ represents a substituted or unsubstituted heteroaryl group having 4 to 9 carbon atoms in a ring. Note that in the case where Ar$^1$ has a substituent, the substituent is an alkyl group having 1 to 4 carbon atoms, an aryl group having 6 to 10 carbon atoms in a ring, or a heteroaryl group having 4 to 9 carbon atoms in a ring. R$^{11}$ to R$^{18}$ each independently represent a hydrogen atom, an alkyl group having 1 to 4 carbon atoms, or a substituted or unsubstituted aryl group having 6 to 10 carbon atoms in a ring. Note that in the case where R$^{11}$ to R$^{18}$ have substituents, the substituents are each independently an alkyl group having 1 to 4 carbon atoms or an aryl group having 6 to 10 carbon atoms in a ring.

Furthermore, among the quinoxaline derivatives represented by General Formula (G1), a quinoxaline derivative represented by General Formula (G5) is preferable because of its ease of synthesis and high triplet level.

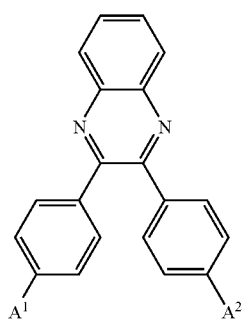

(G5)

In General Formula (G5), A$^1$ and A$^2$ each independently represent a hydrogen atom, an alkyl group having 1 to 4 carbon atoms, an aryl group having 6 to 10 carbon atoms in a ring, or a substituent represented by General Formula (A5) below. Note that at least one of A$^1$ and A$^2$ has the substituent represented by General Formula (A5).

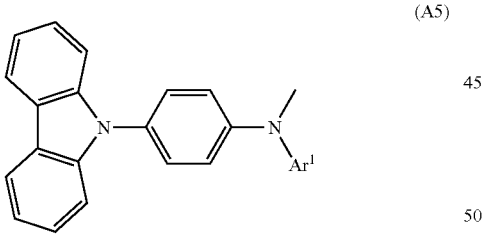

(A5)

In General Formula (A5), Ar$^1$ represents a substituted or unsubstituted heteroaryl group having 4 to 9 carbon atoms in a ring. Note that in the case where Ar$^1$ has a substituent, the substituent is an alkyl group having 1 to 4 carbon atoms, an aryl group having 6 to 10 carbon atoms in a ring, or a heteroaryl group having 4 to 9 carbon atoms in a ring.

As examples of specific structures of R$^1$ to R$^4$ in the above general formula (G1), there are substituents represented by Structural Formulae (1-1) to (1-22).

 (1-1)

 (1-2)

-continued

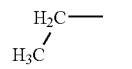 (1-3)

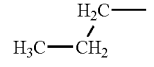 (1-4)

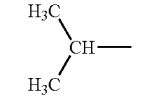 (1-5)

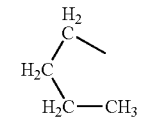 (1-6)

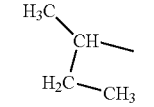 (1-7)

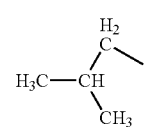 (1-8)

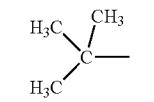 (1-9)

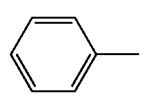 (1-10)

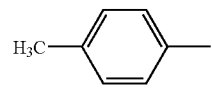 (1-11)

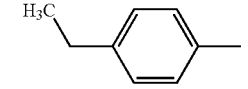 (1-12)

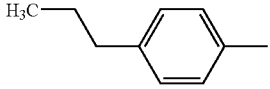 (1-13)

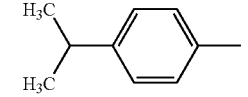 (1-14)

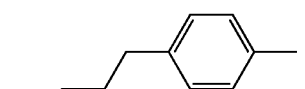 (1-15)

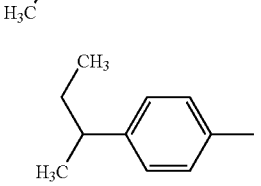 (1-16)

(1-17) 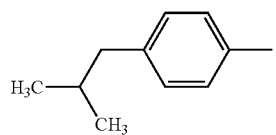
(1-18) 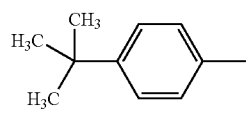
(1-19) 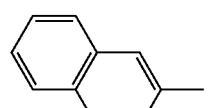
(1-20) 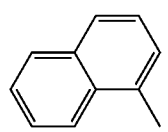
(1-21) 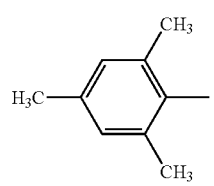
(1-22) 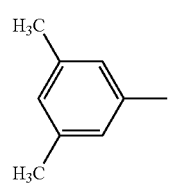
As examples of specific structures of J in the above general formulae (A1) and (A2), there are substituents represented by Structural Formulae (2-1) to (2-20).
(2-1) 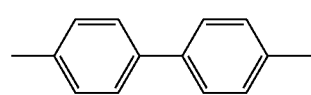
(2-2) 
(2-3) 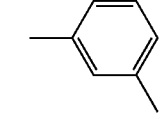
(2-4) 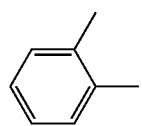
(2-5) 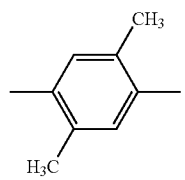
(2-6) 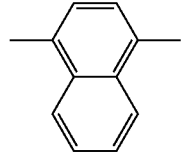
(2-7) 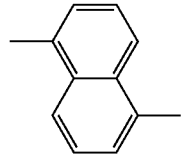
(2-8) 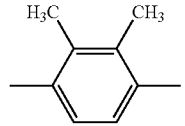
(2-9) 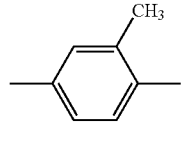
(2-10) 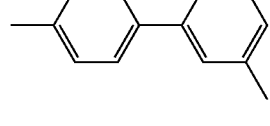
(2-11) 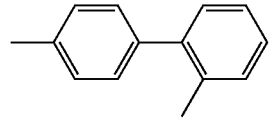
(2-12) 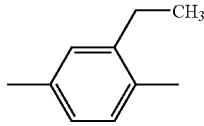
(2-13) 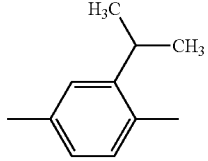
(2-14) 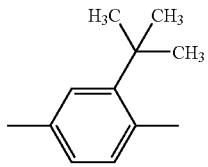

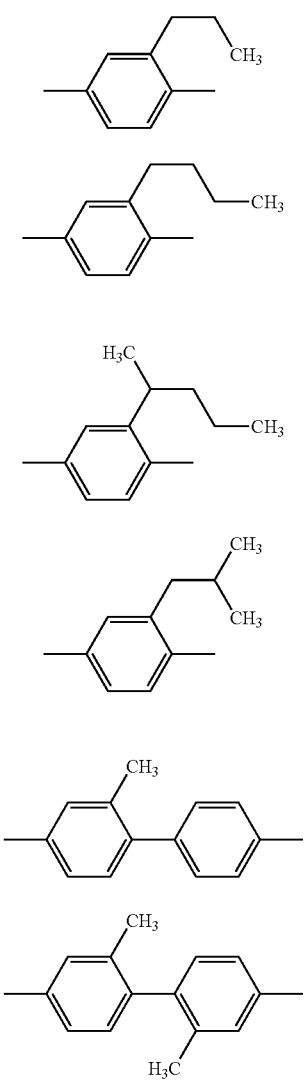
As examples of specific structures of $R^{11}$ to $R^{18}$ in the above general formulae (A1) to (A4), there are substituents represented by Structural Formulae (3-1) to (3-30).
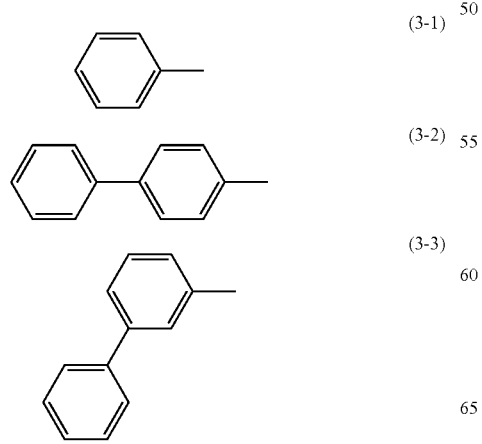
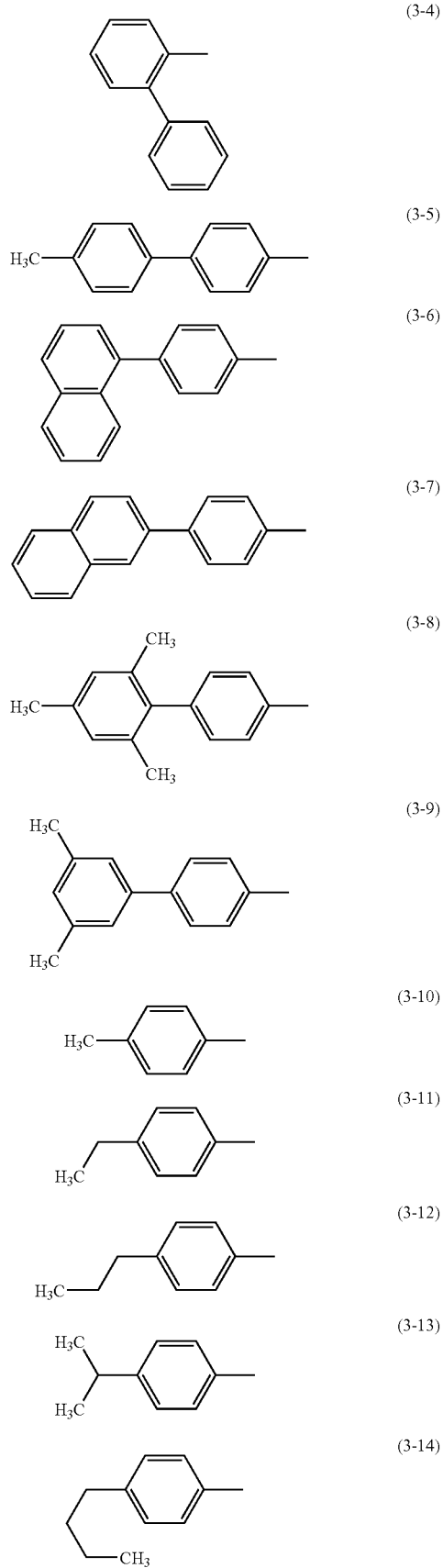

-continued
(3-15) 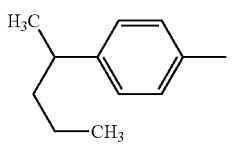
(3-16) 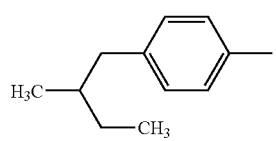
(3-17) 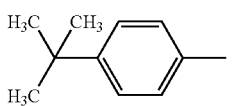
(3-18) 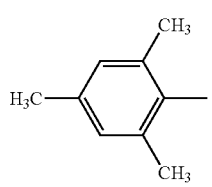
(3-19) 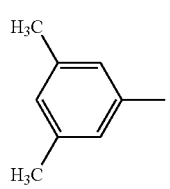
(3-20) 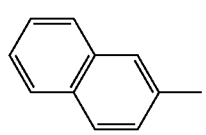
(3-21) 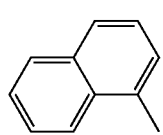
(3-22) 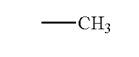
(3-23) 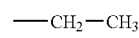
(3-24) 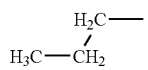
(3-25) 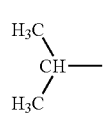
(3-26) 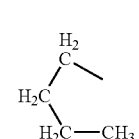
(3-27) 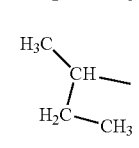
-continued
(3-28) 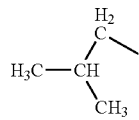
(3-29) 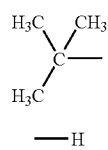
(3-30) —H
As examples of specific structures of $Ar^1$ in the above general formulae (A1) to (A5), there are substituents represented by Structural Formulae (4-1) to (4-29).
(4-1) 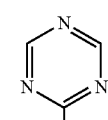
(4-2) 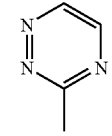
(4-3) 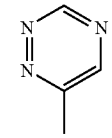
(4-4) 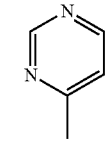
(4-5) 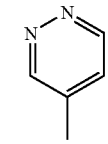
(4-6) 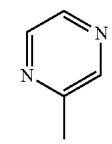
(4-7) 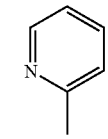
(4-8) 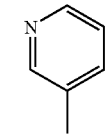

-continued
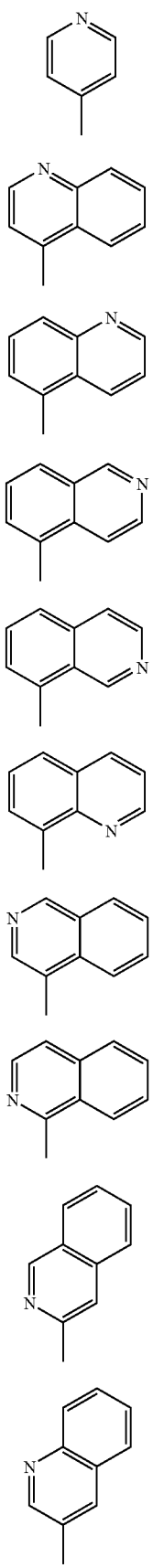
(4-9)
(4-10)
(4-11)
(4-12)
(4-13)
(4-14)
(4-15)
(4-16)
(4-17)
(4-18)
-continued
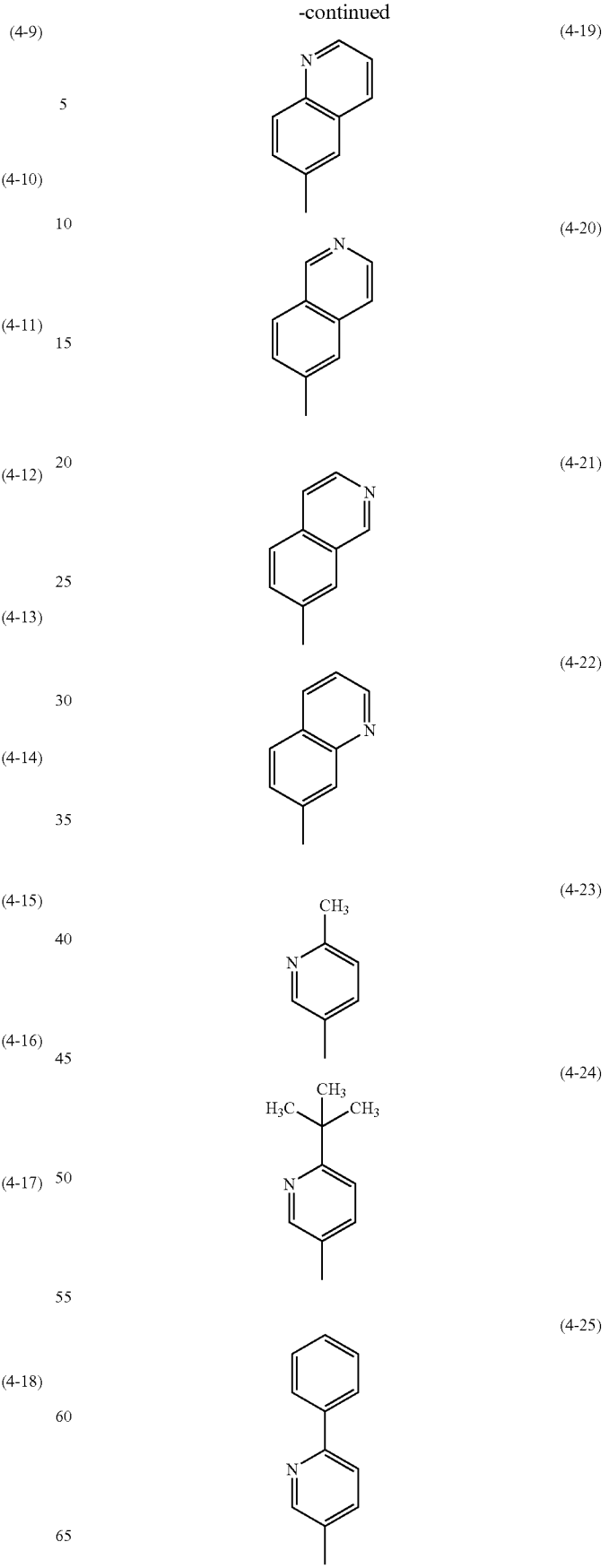
(4-19)
(4-20)
(4-21)
(4-22)
(4-23)
(4-24)
(4-25)

-continued
(4-26)
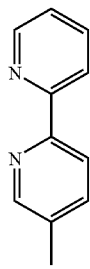
(4-27)
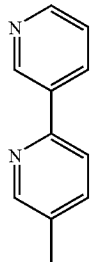
(4-28)
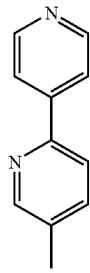
(4-29)
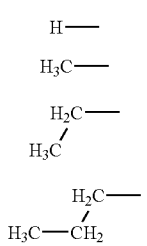
As examples of specific structures of the hydrogen atom, the alkyl group having 1 to 4 carbon atoms, or the aryl group having 6 to 10 carbon atoms in a ring, which is represented by $A^1$ or $A^2$ in the above general formulae (A1) to (A4), there are substituents represented by Structural Formulae (5-1) to (5-22).
(5-1) H—
(5-2) H$_3$C—
(5-3) 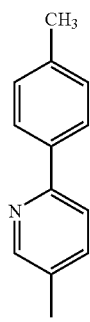
(5-4) 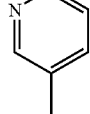
-continued
(5-5) 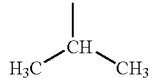
(5-6) 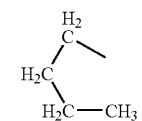
(5-7) 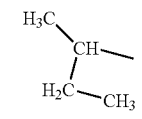
(5-8) 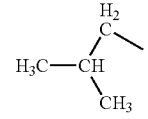
(5-9) 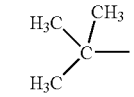
(5-10) 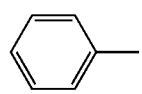
(5-11) 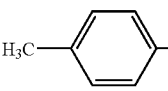
(5-12) 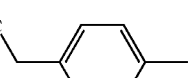
(5-13) 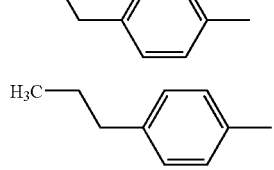
(5-14) 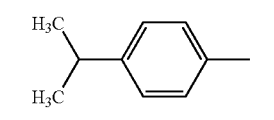
(5-15) 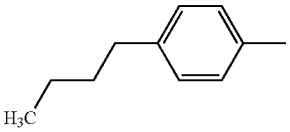
(5-16) 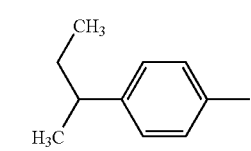

(5-17) 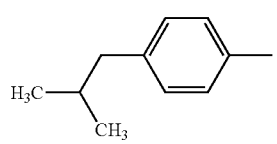
(5-18) 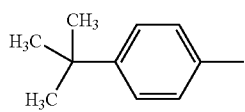
(5-19) 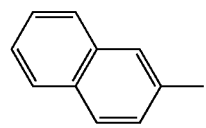
(5-20) 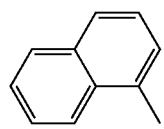
(5-21) 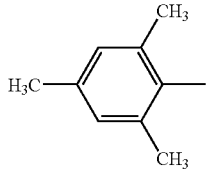
(5-22) 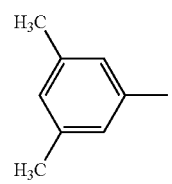
As specific examples of the quinoxaline derivative of an embodiment of the present invention, represented by General Formula (G1), there are quinoxaline derivatives represented by Structural Formulae (100) to (218). Note that this embodiment is not limited to these examples.
(100)
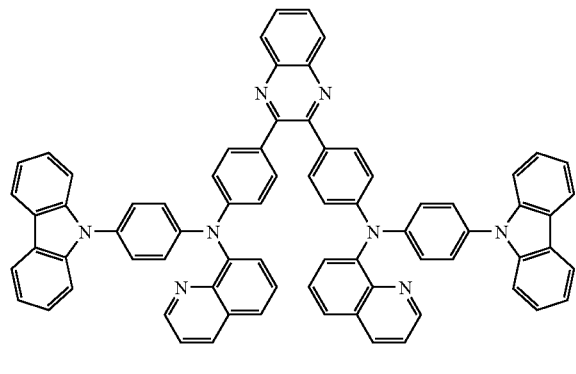
(101)
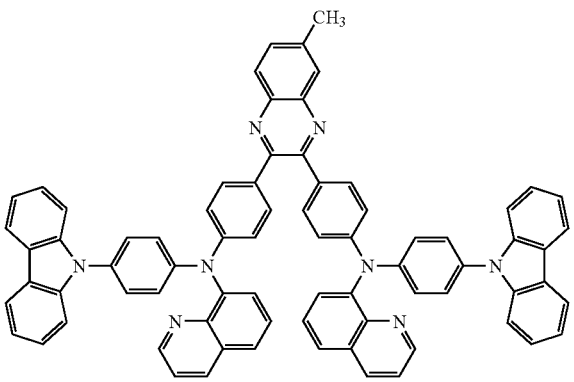
(102)
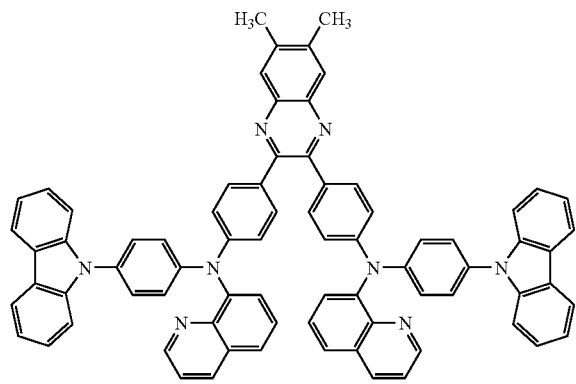
(103)
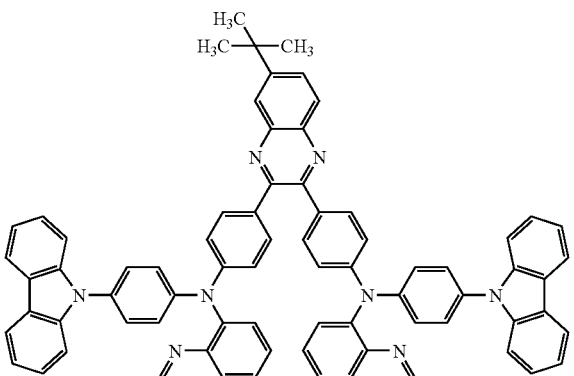

-continued
(104)
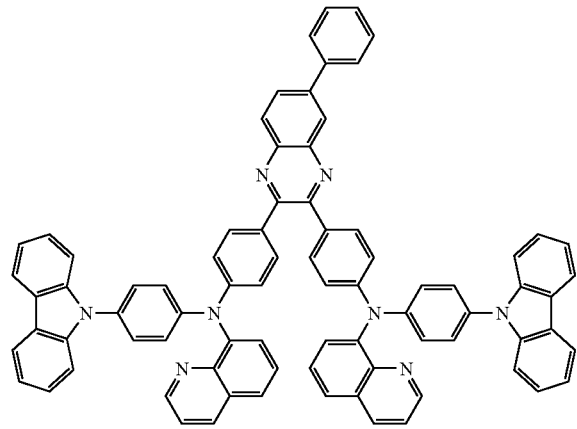
(105)
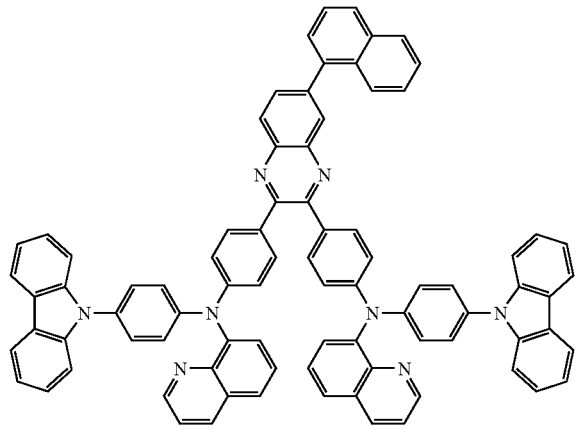
(106)
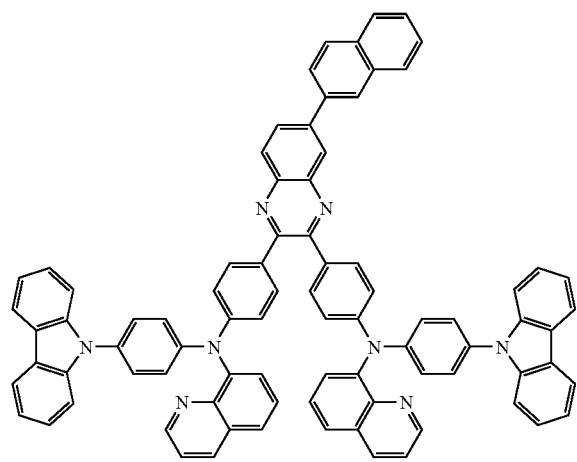
(107)
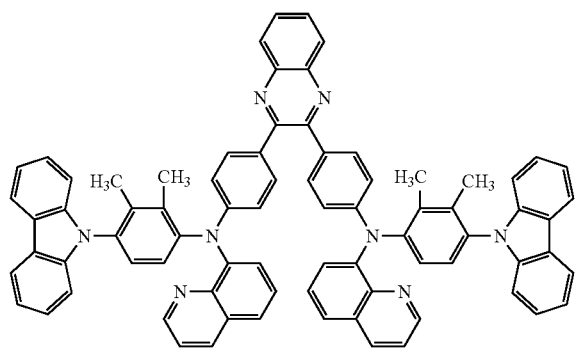
(108)
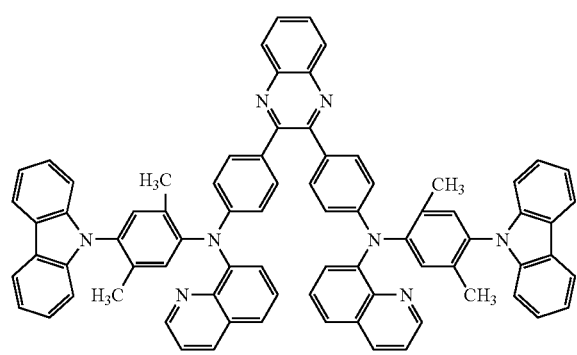
(109)
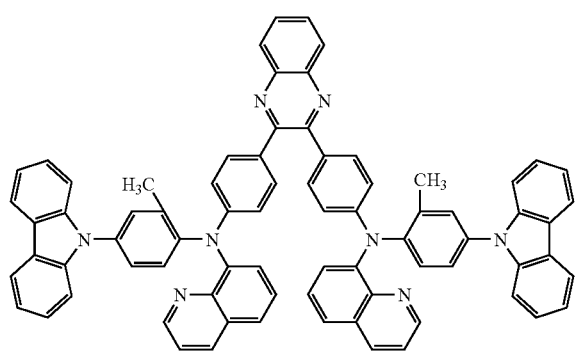
(110)
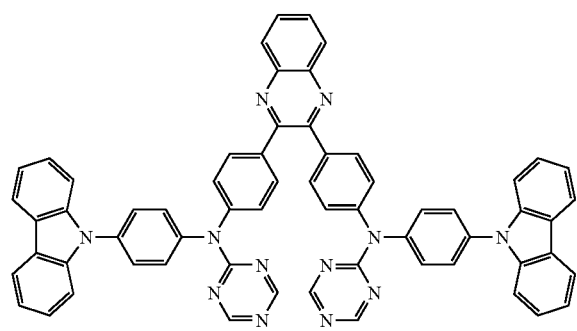
(111)
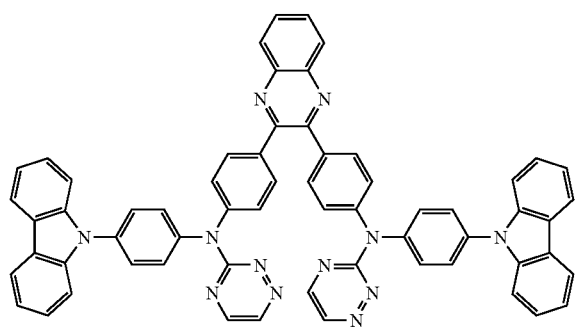

-continued
(112)
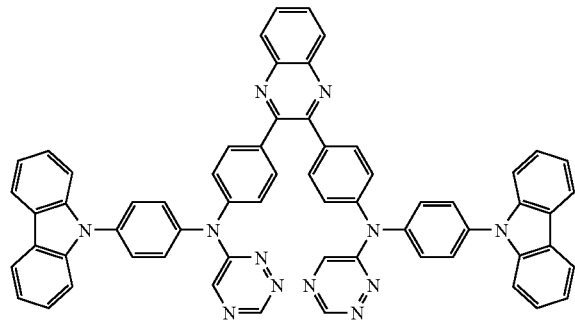
(113)
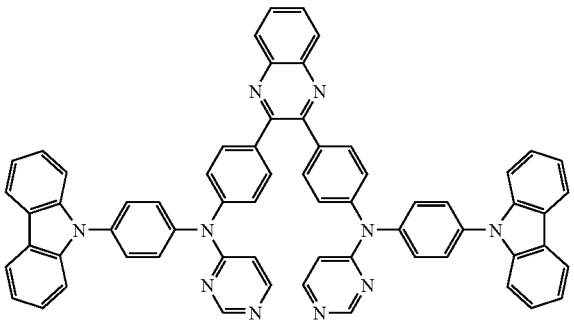
(114)
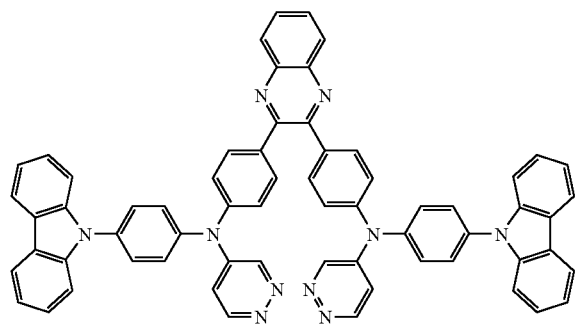
(115)
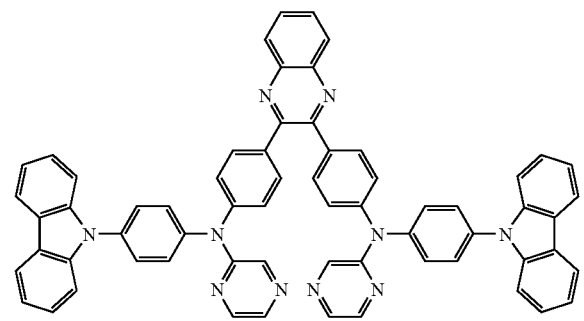
(116)
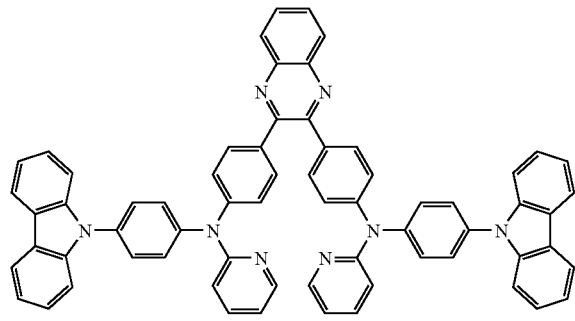
(117)
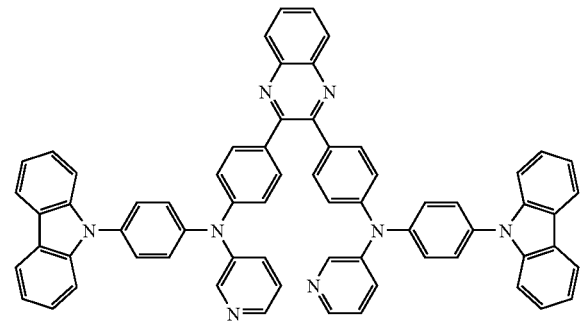
(118)
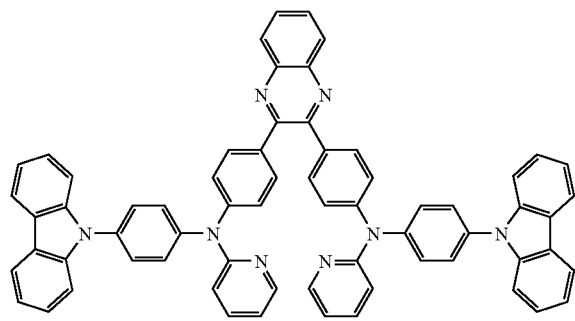
(119)
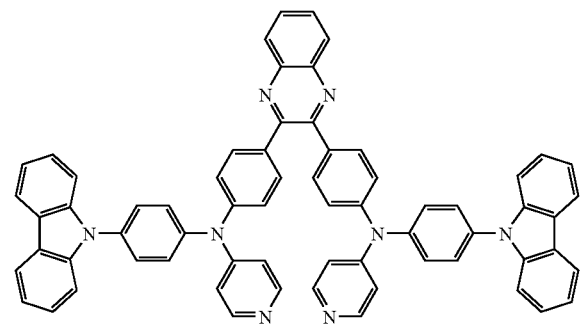

-continued
(120)
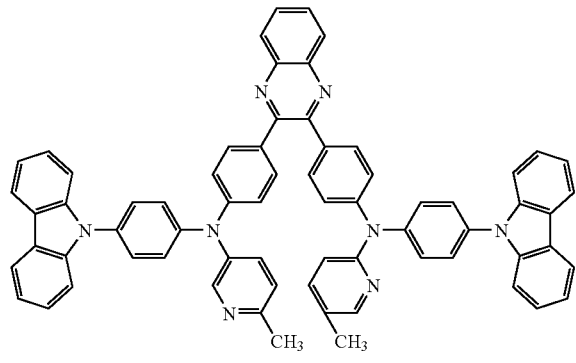
(121)
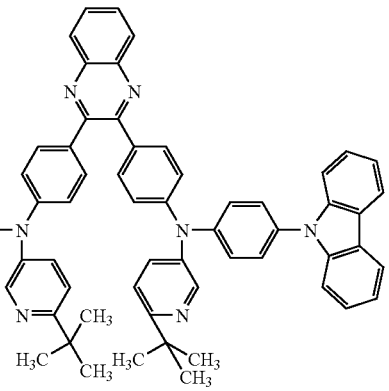
(122)
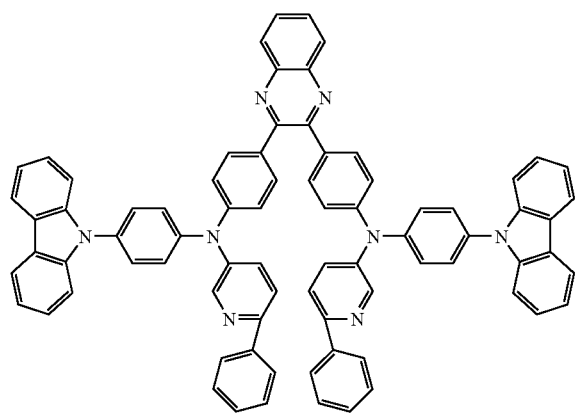
(123)
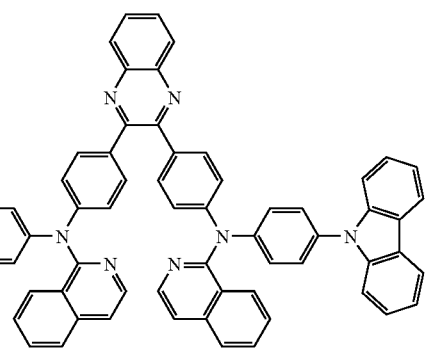
(124)
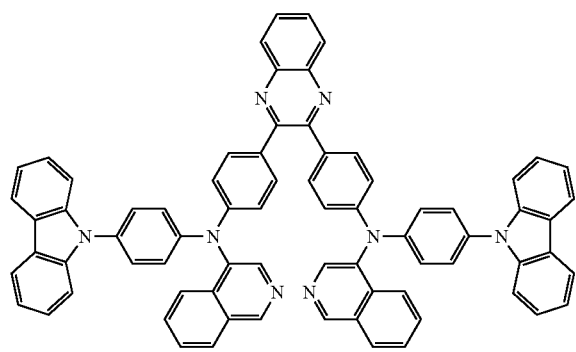
(125)
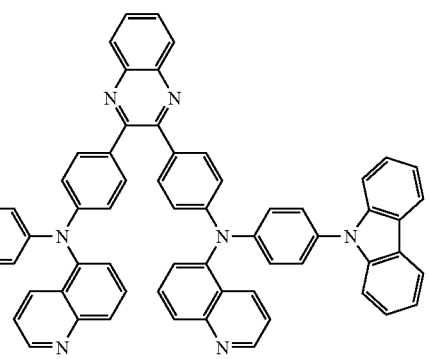
(126)
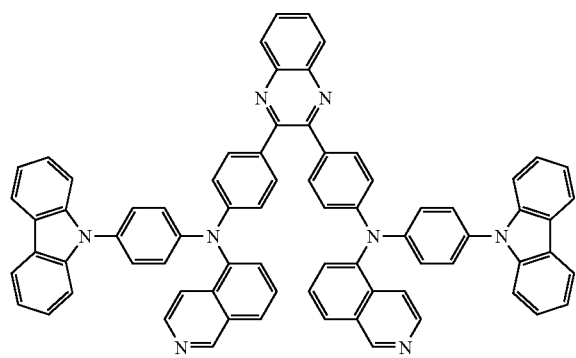
(127)
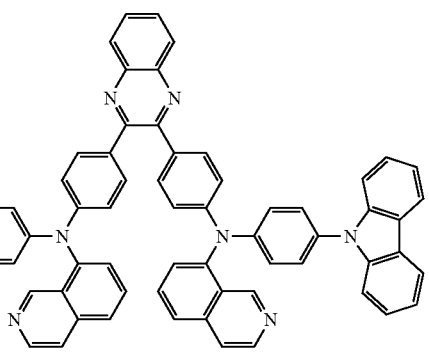

-continued
(128)
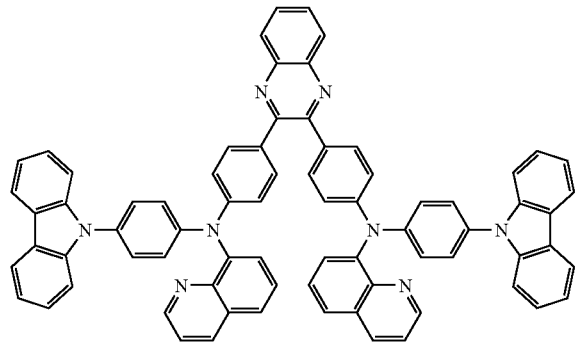
(129)
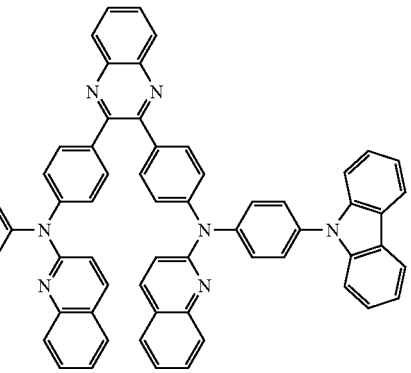
(130)
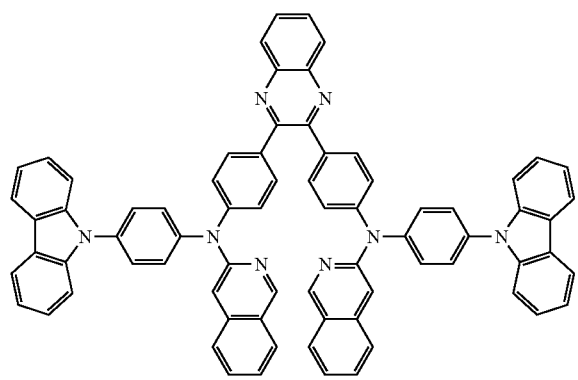
(131)
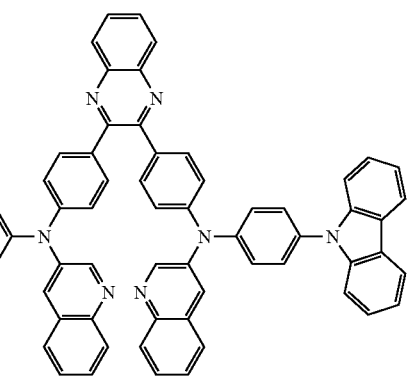
(132)
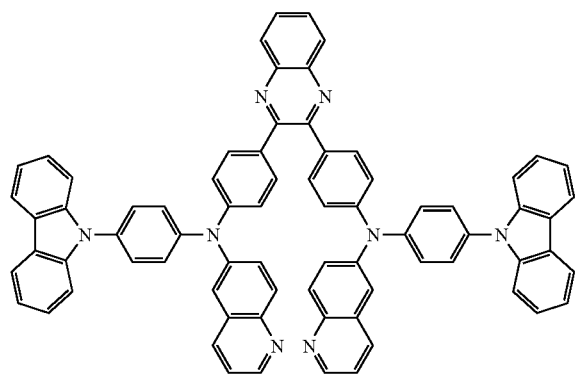
(133)
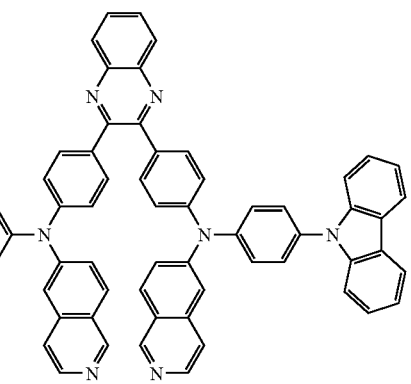
(134)
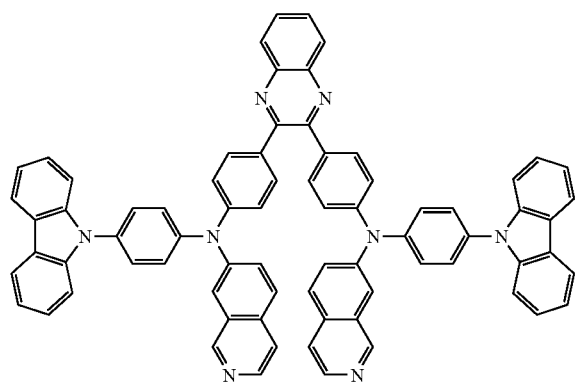
(135)
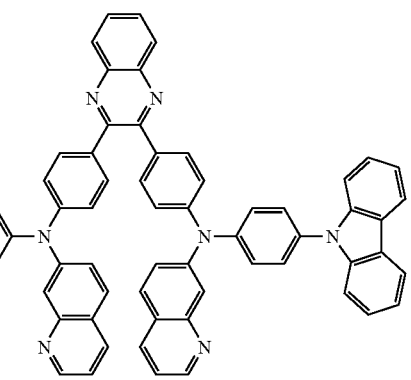

-continued
(136)
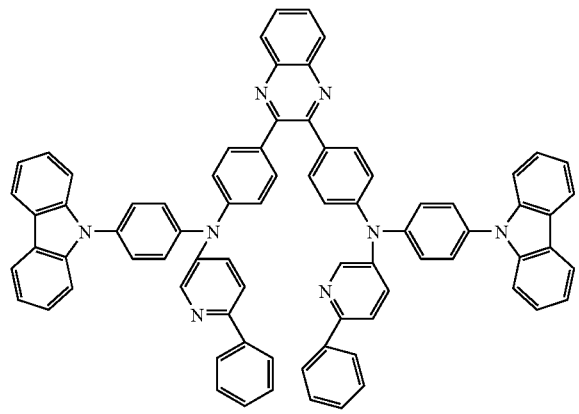
(137)
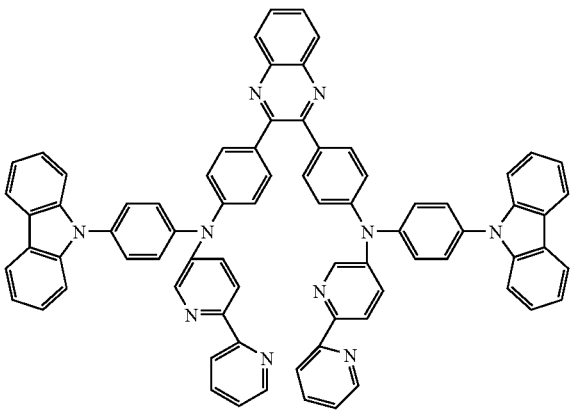
(138)
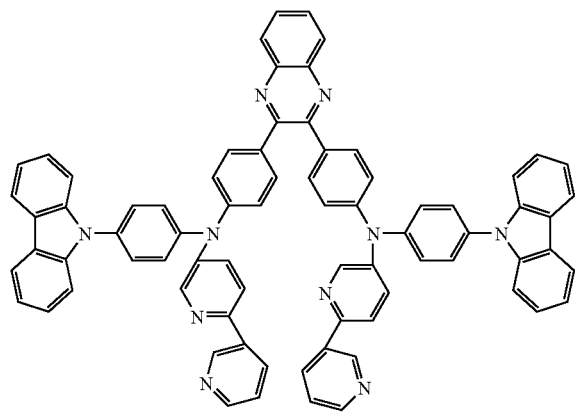
(139)
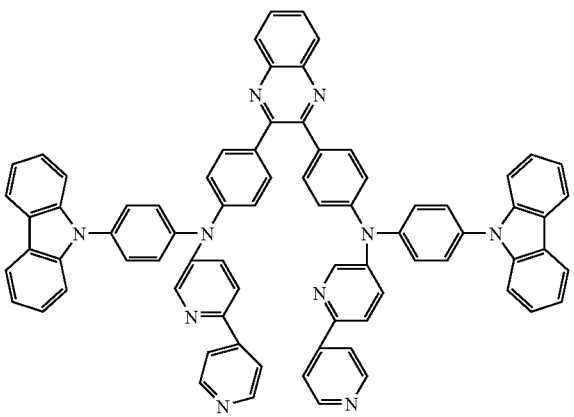
(140)
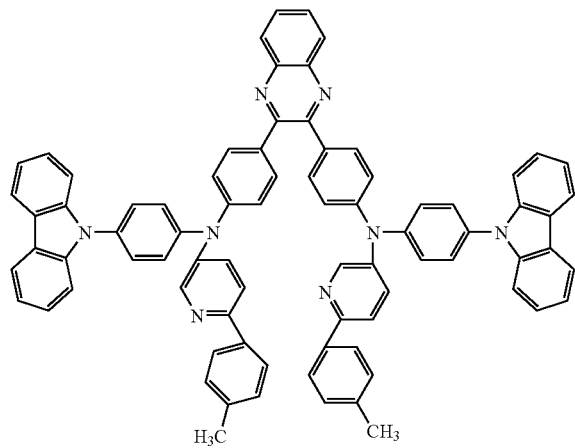

(141)
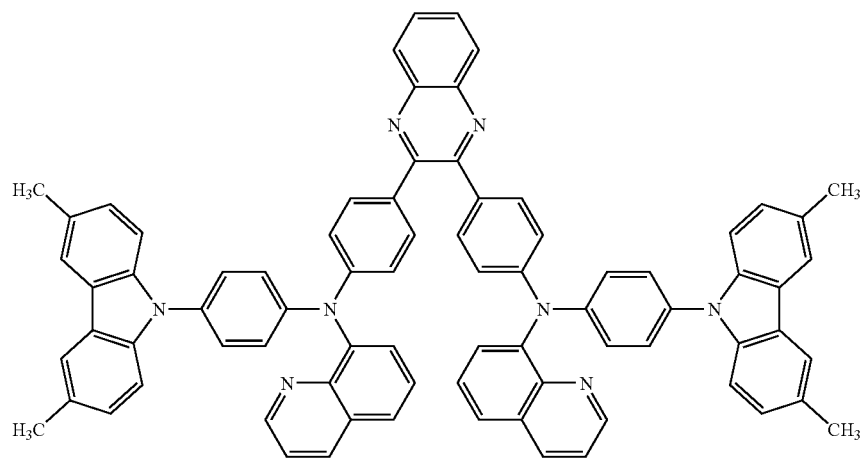
(142)
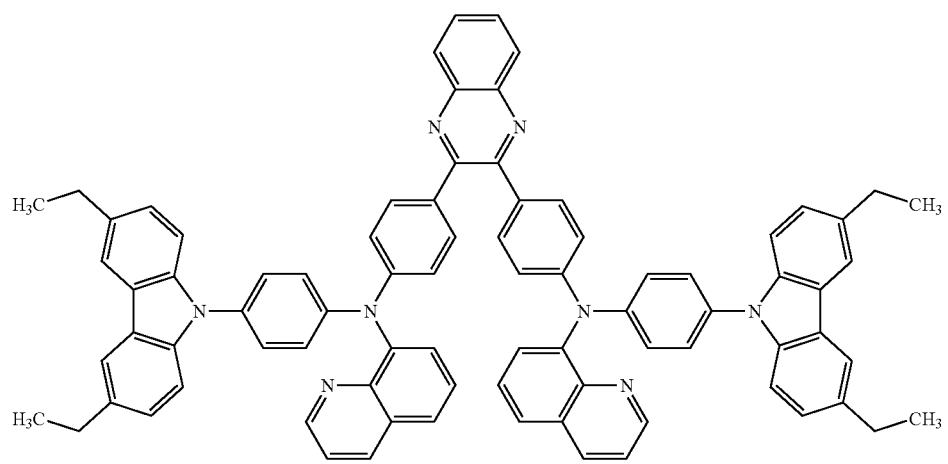
(143)
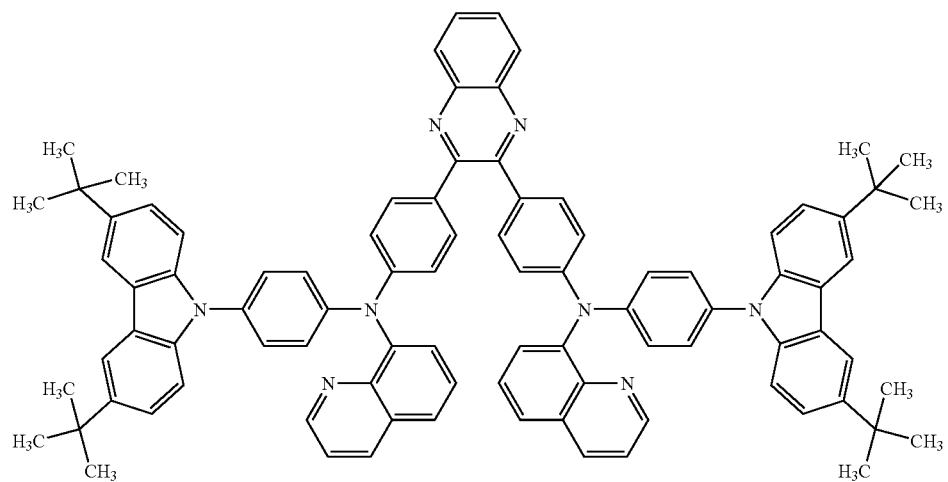

(144)
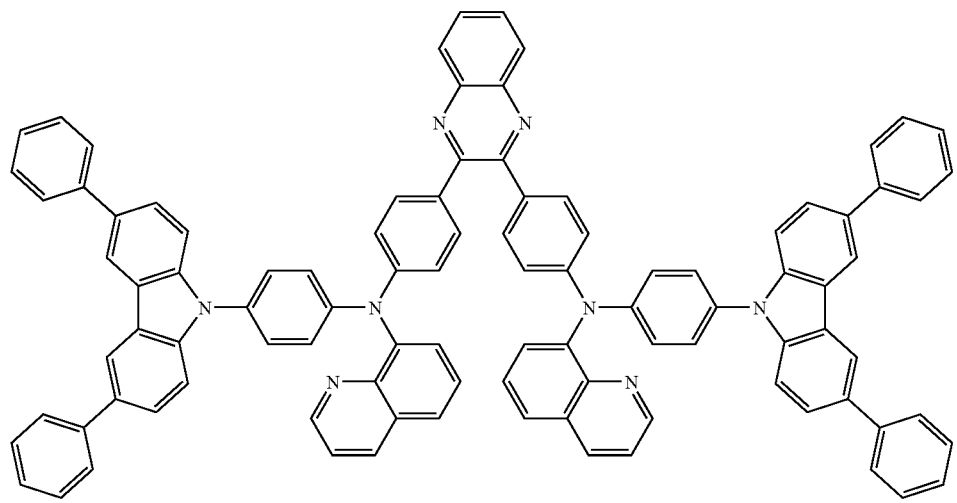
(145)
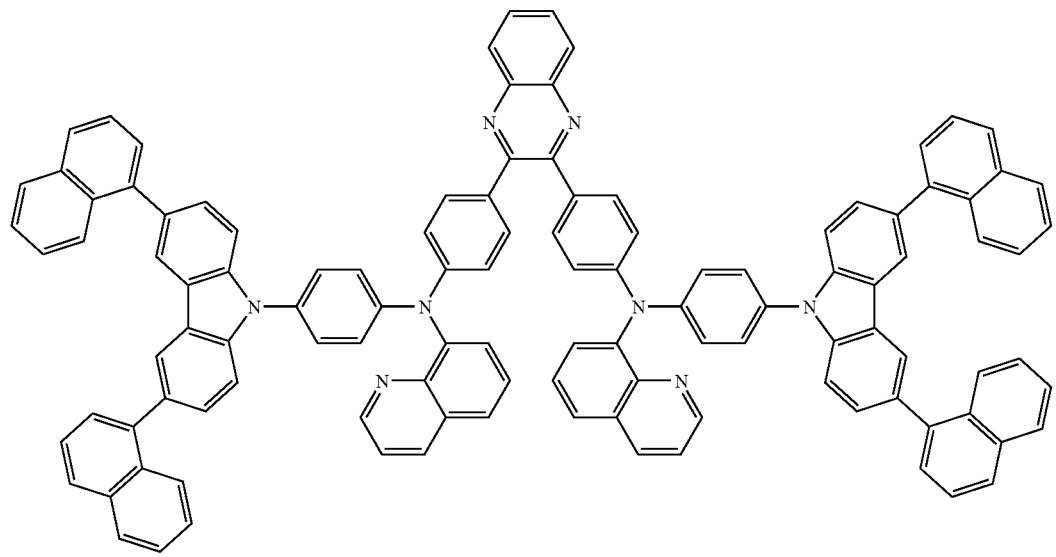
(146)
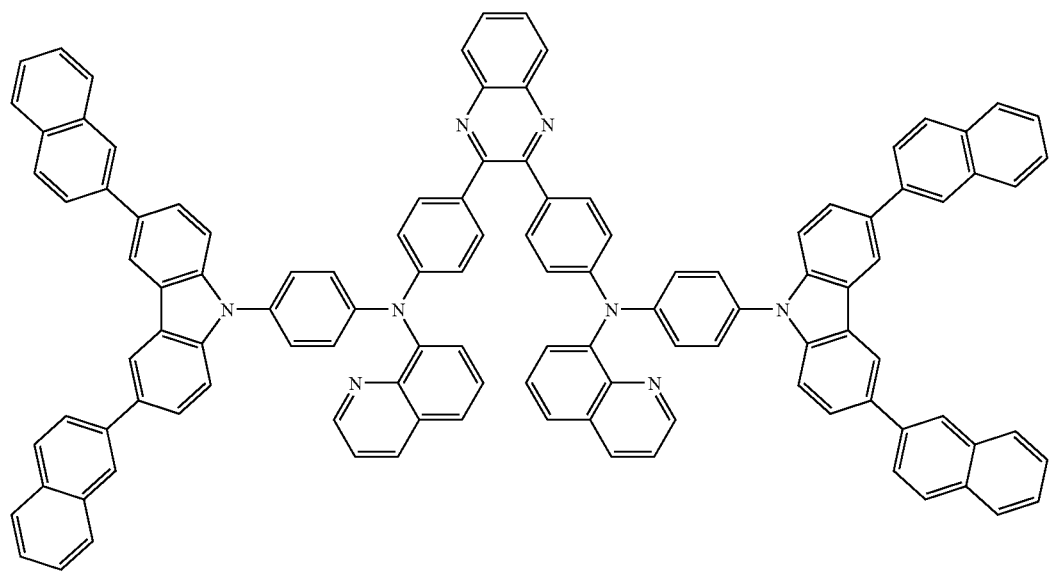

(147)
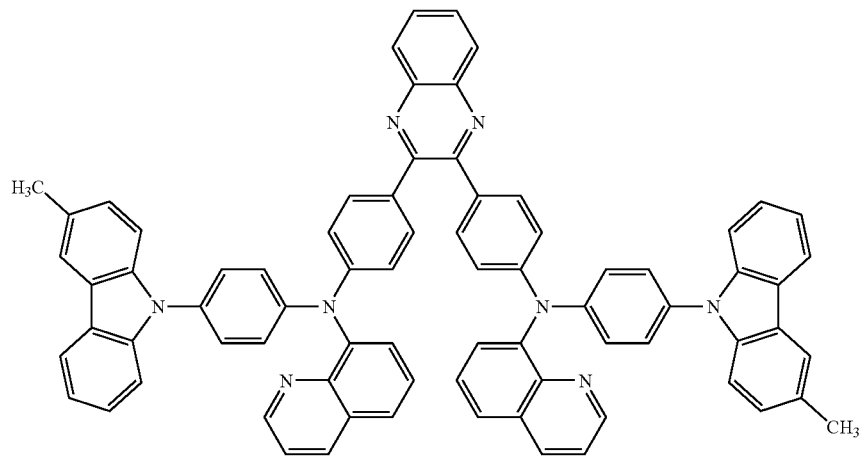
(148)
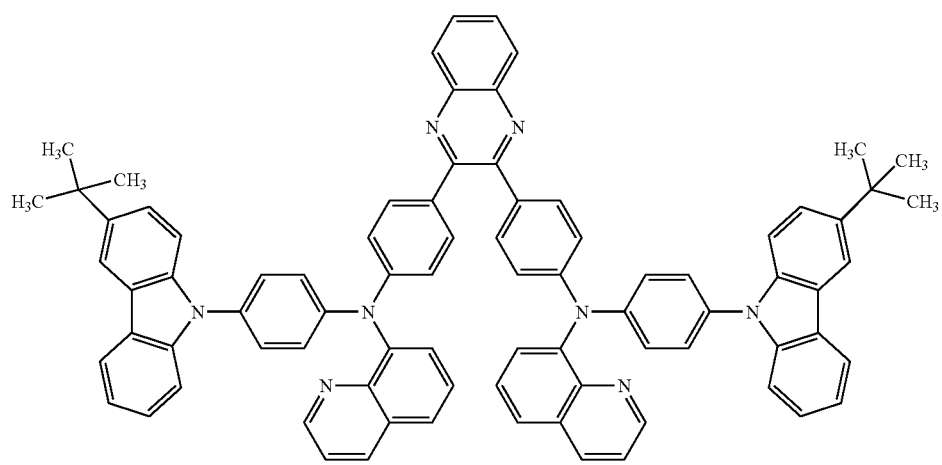
(149)
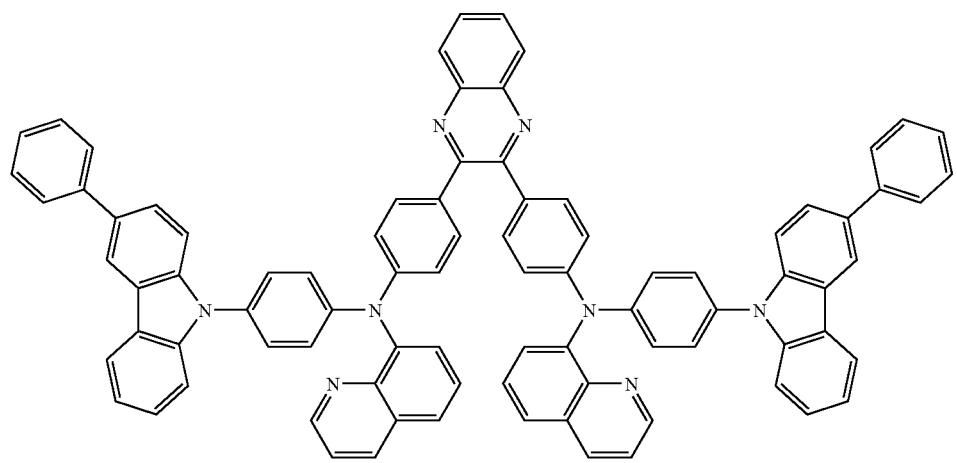

-continued
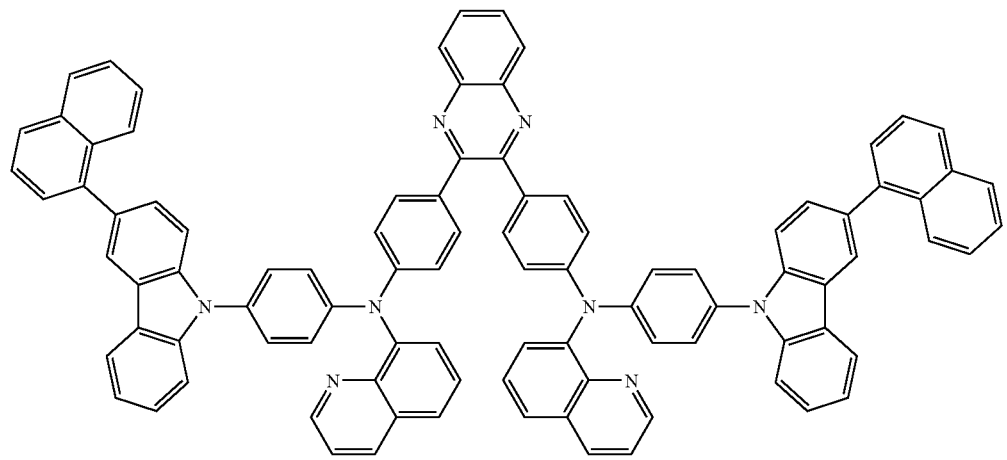
(150)
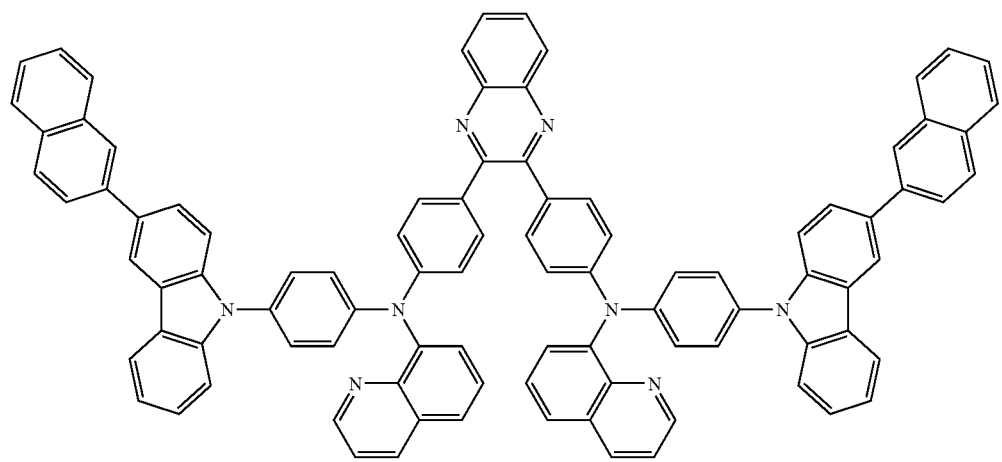
(151)
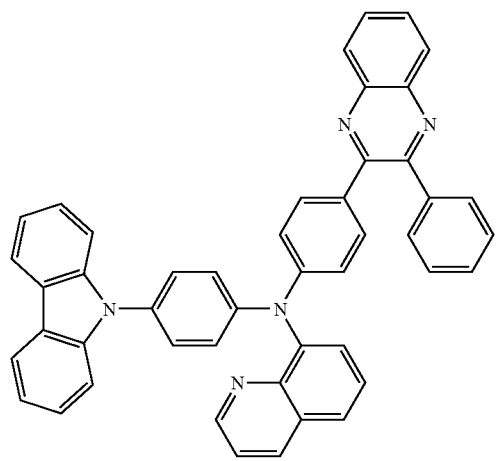
(152)
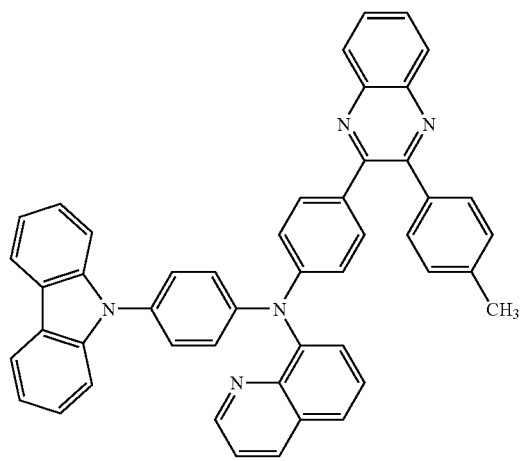
(153)

-continued
(154)
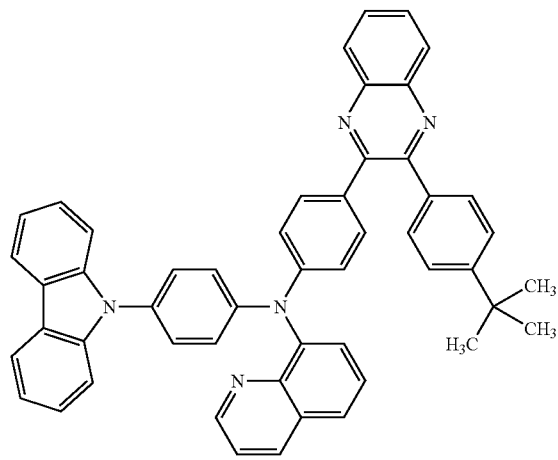
(155)
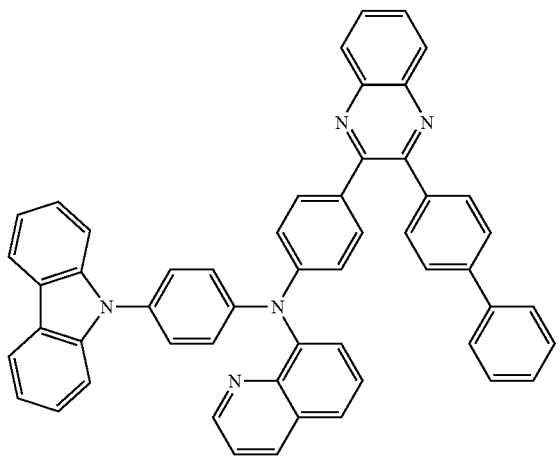
(156)
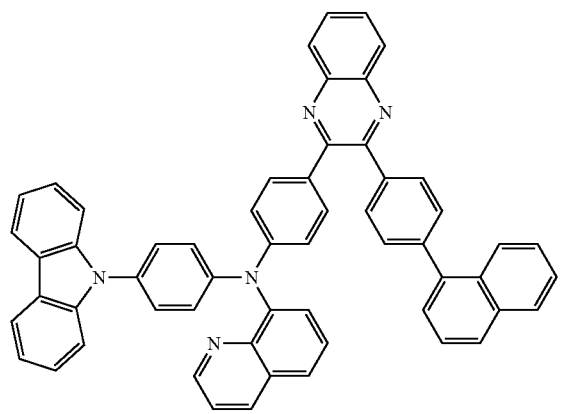
(157)
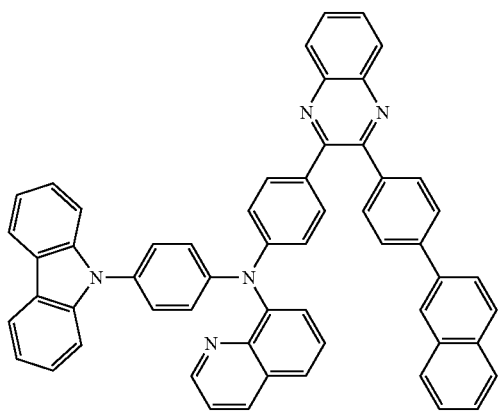
(158)
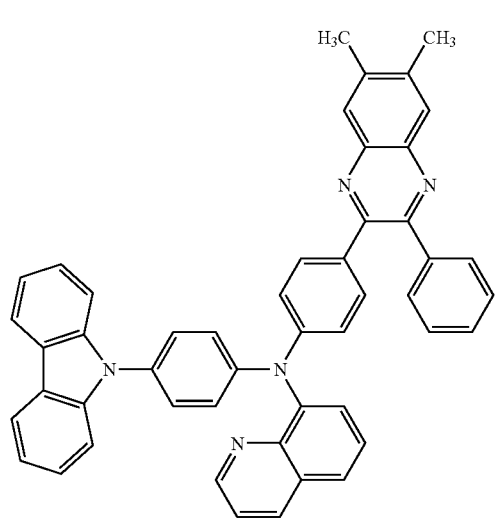
(159)
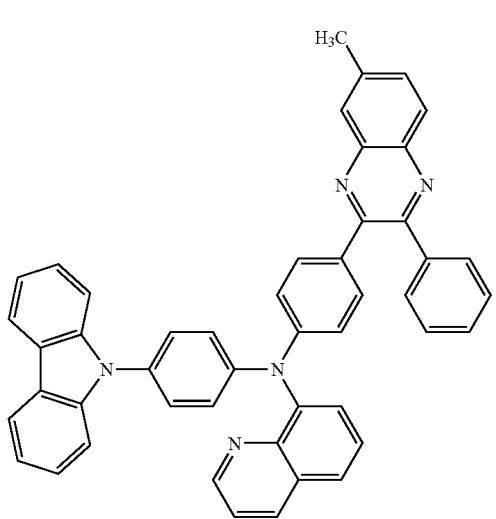

-continued
(160)
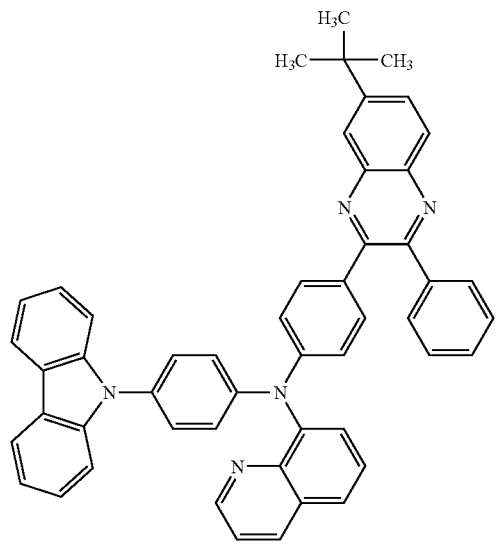
(161)
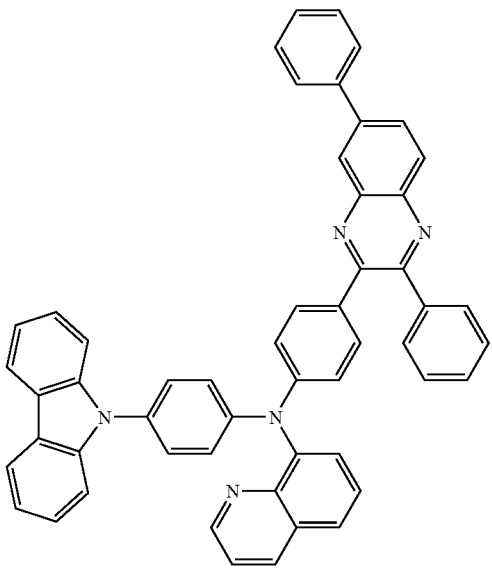
(162)
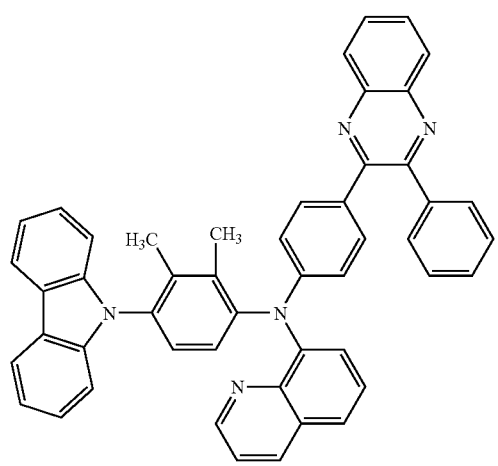
(163)
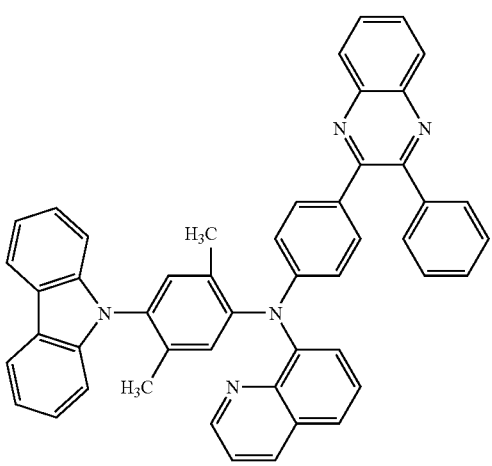
(164)
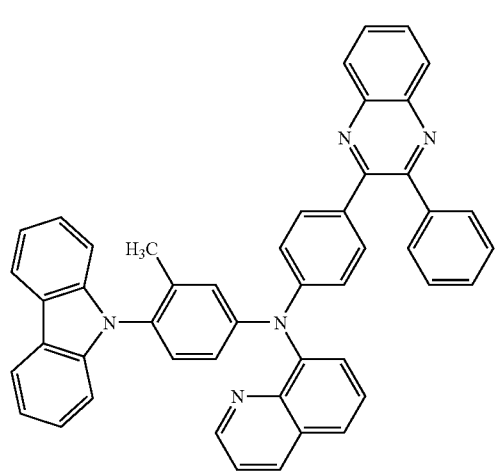
(165)
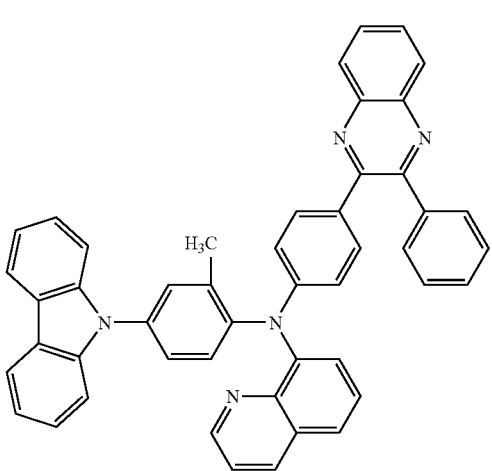

-continued
(166)
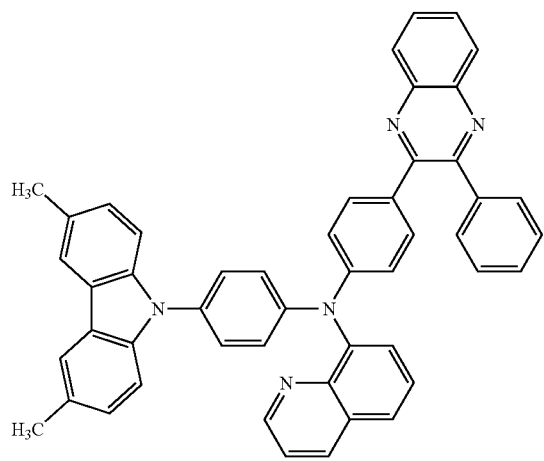
(167)
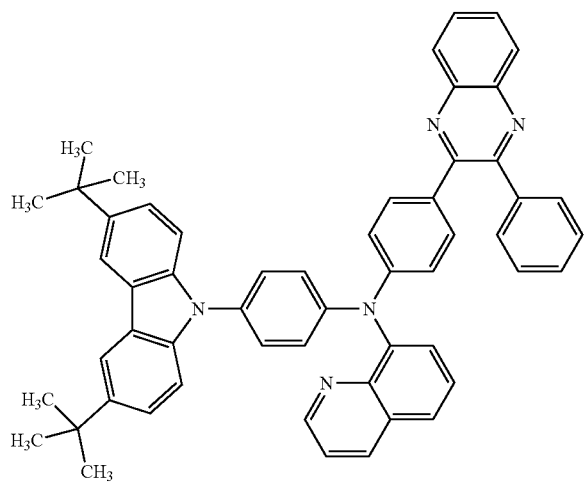
(168)
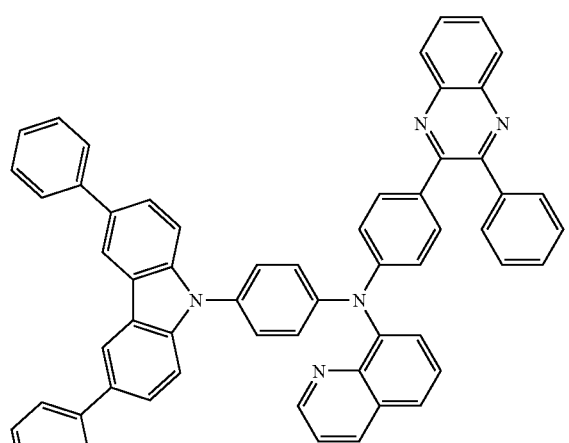
(169)
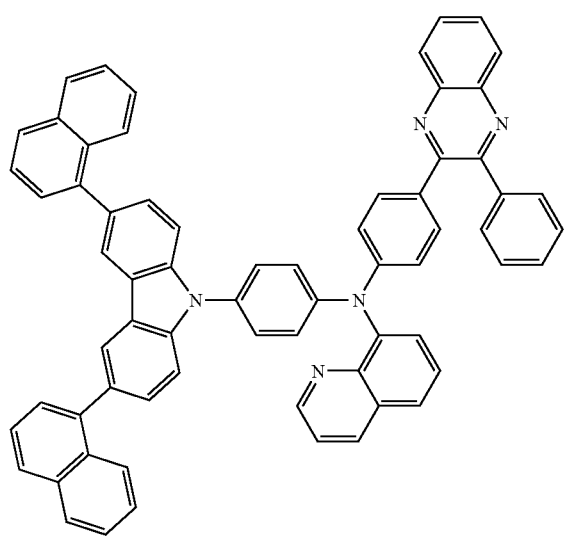
(170)
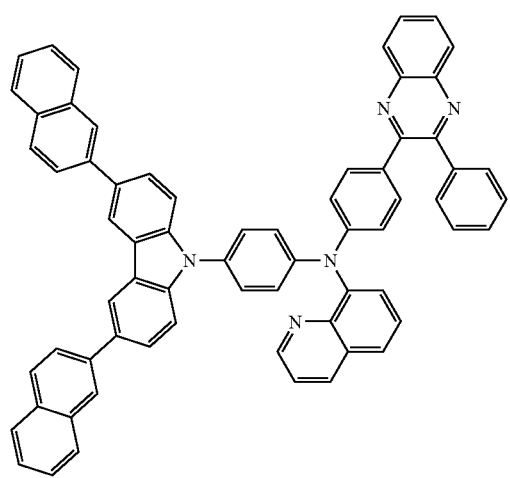
(171)
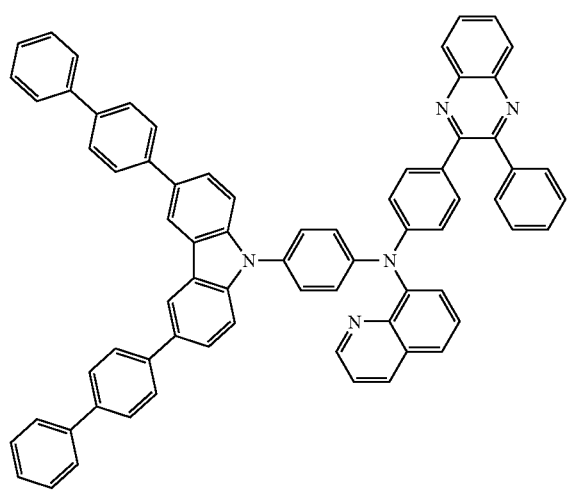

-continued
(172)
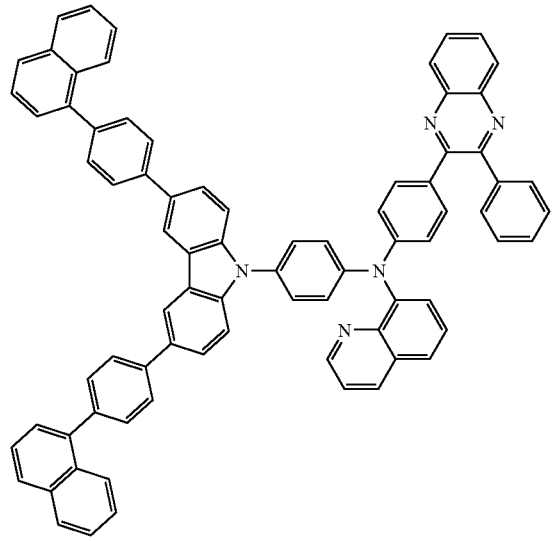
(173)
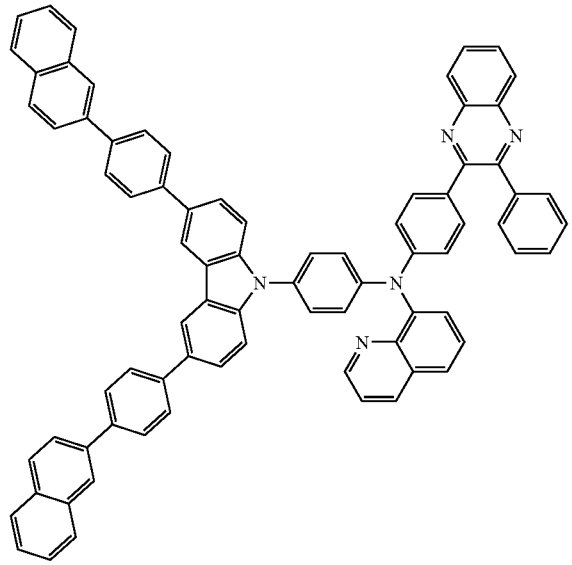
(174)
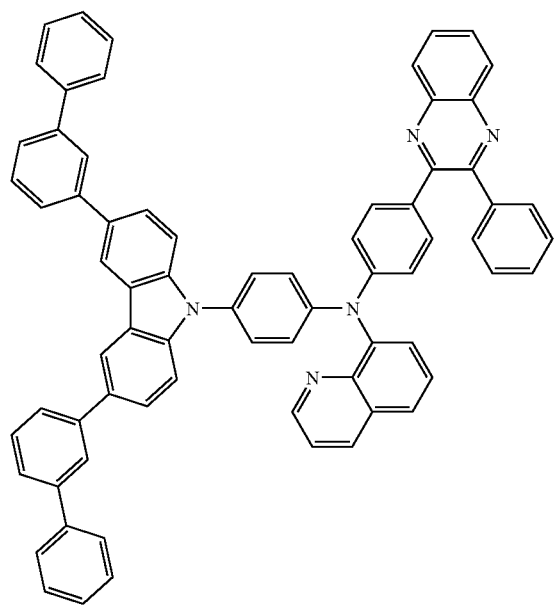
(175)
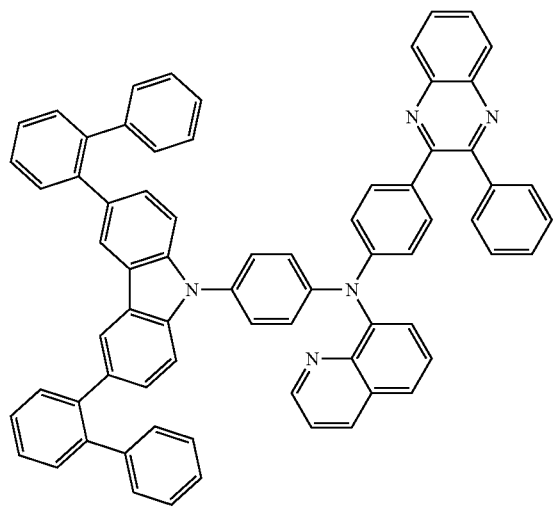
(176)
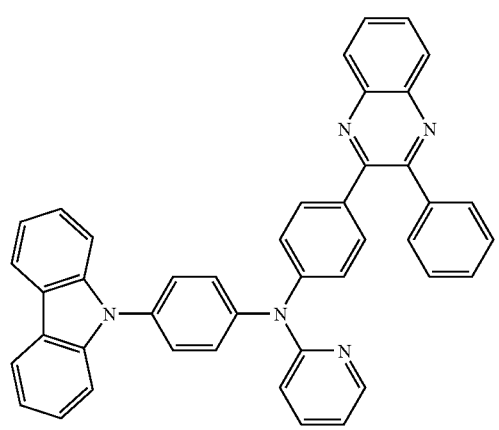
(177)
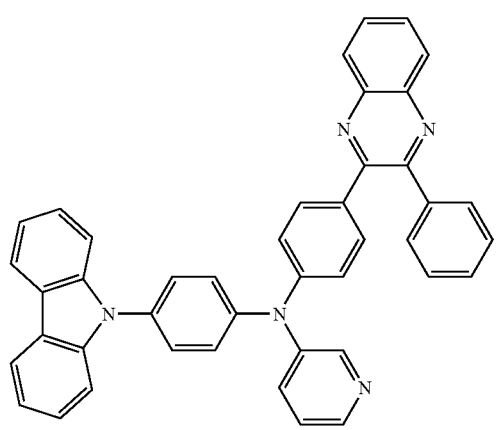

-continued
(178)
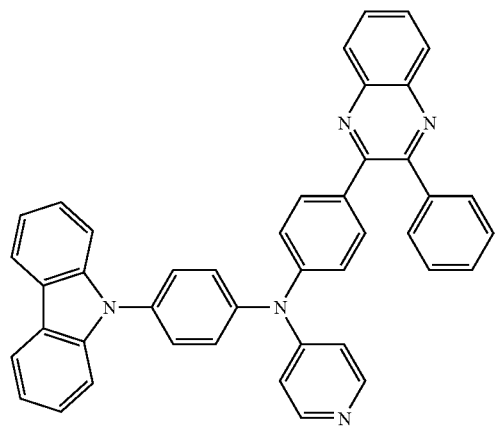
(179)
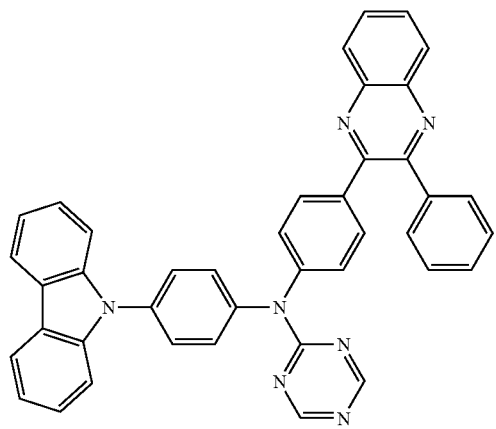
(180)
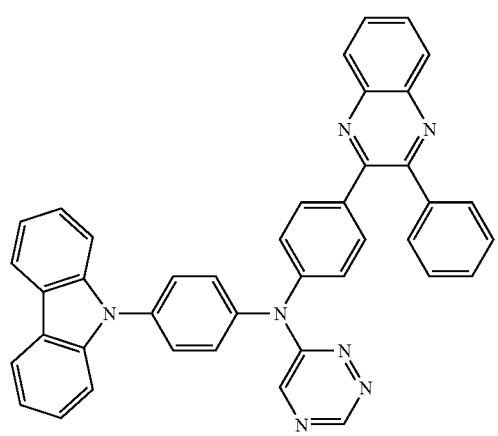
(181)
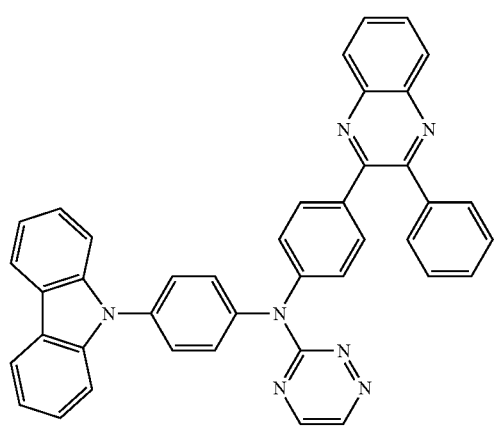
(182)
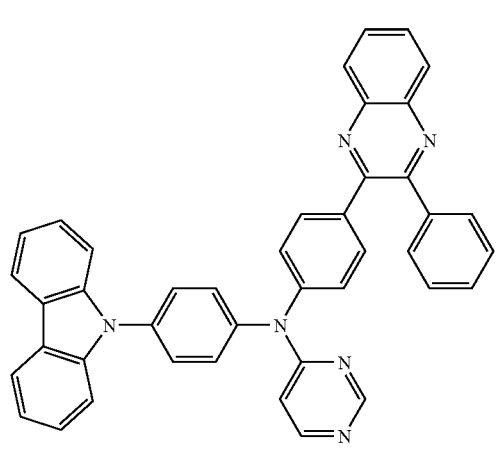
(183)
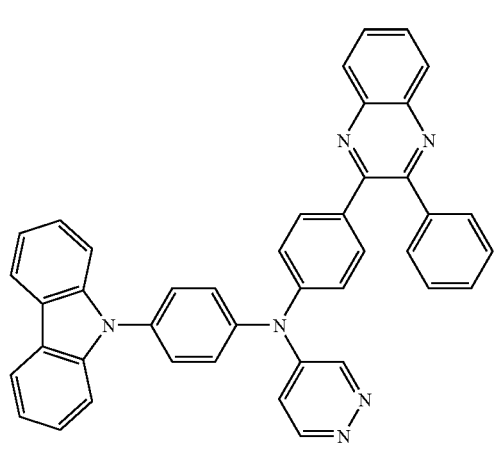

(184)
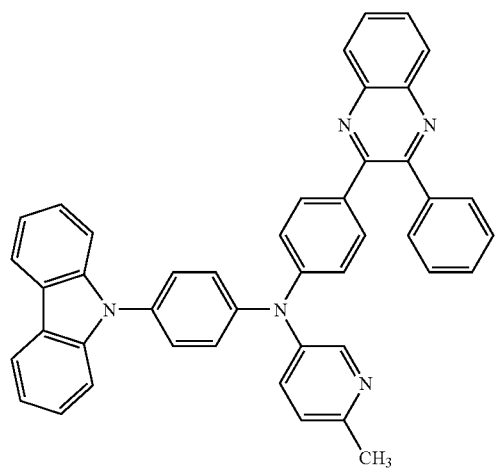
(185)
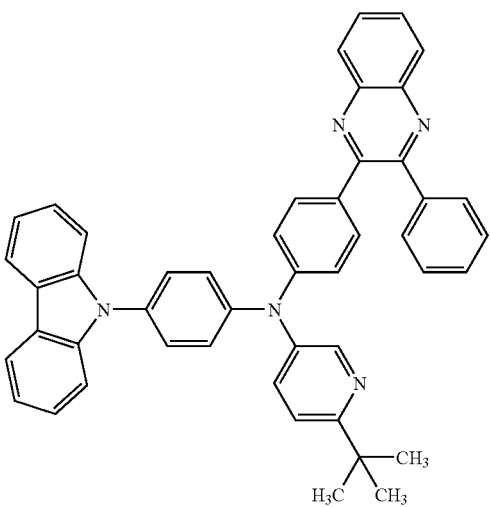
(186)
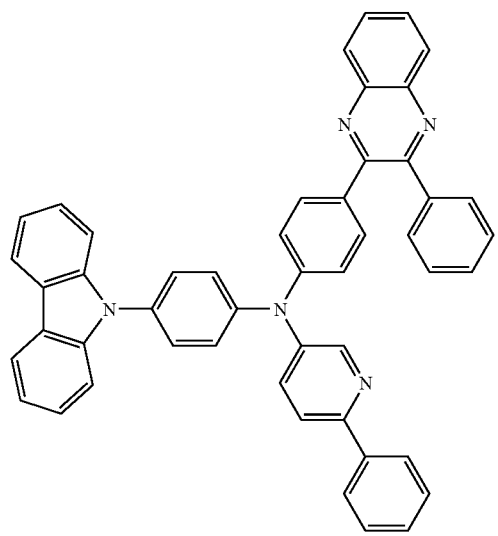
(187)
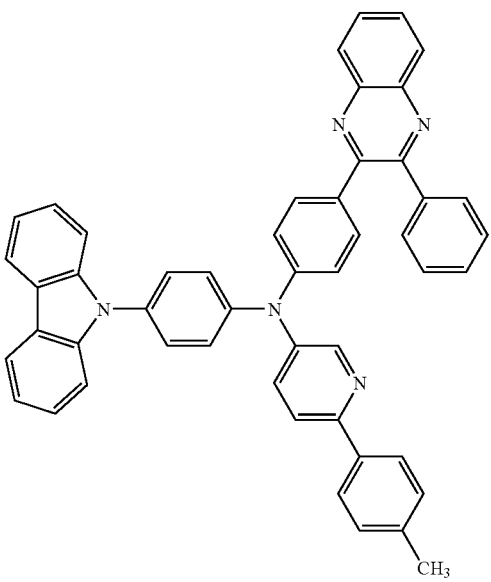
(188)
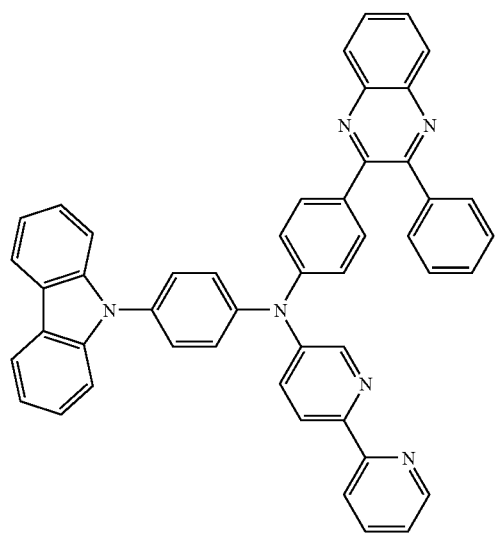
(189)
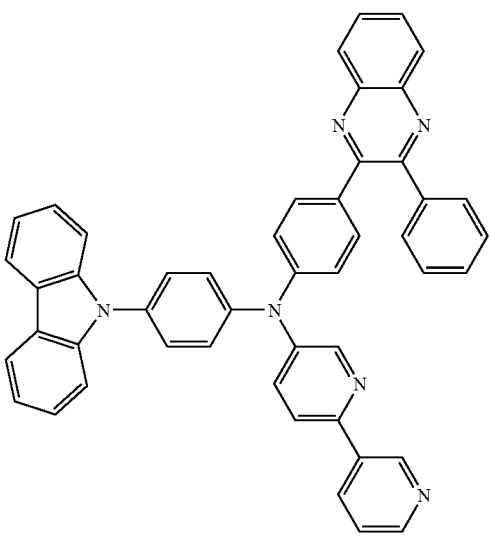

-continued
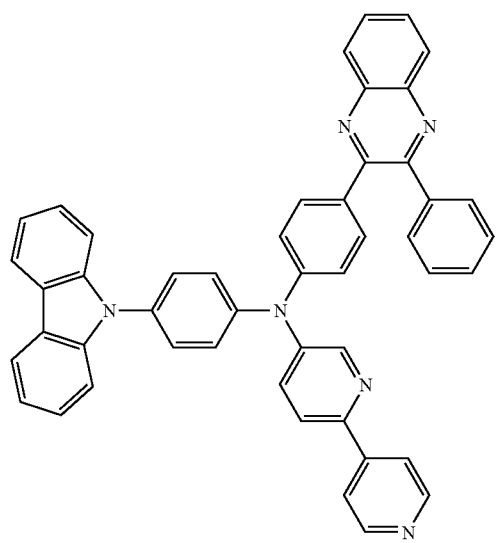
(190)
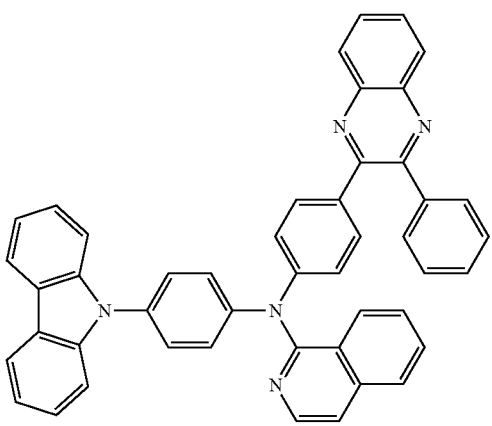
(191)
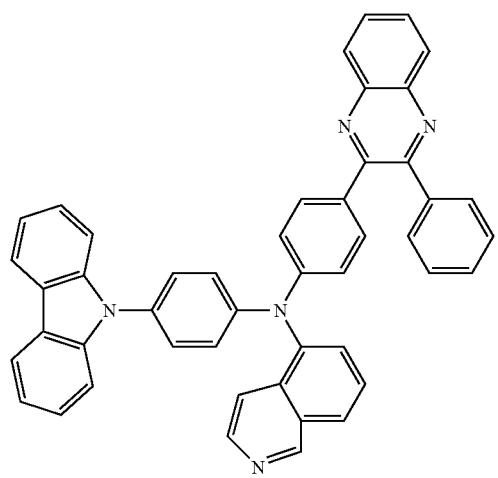
(192)
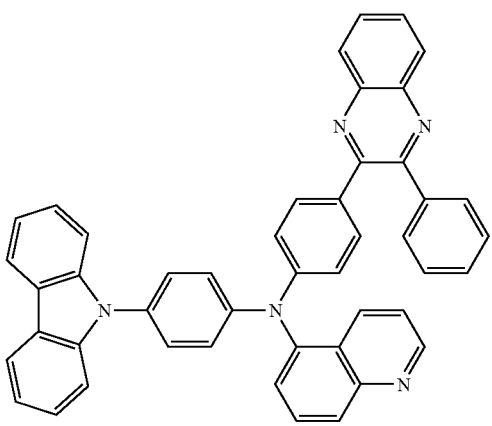
(193)
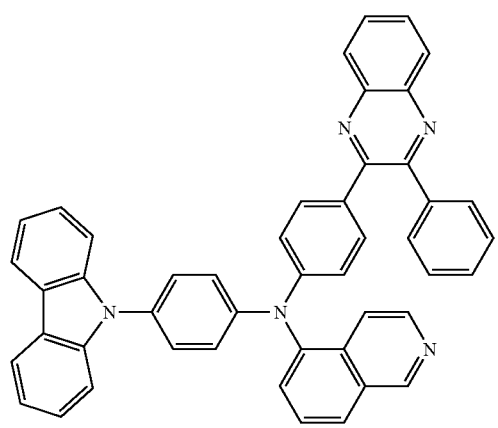
(194)
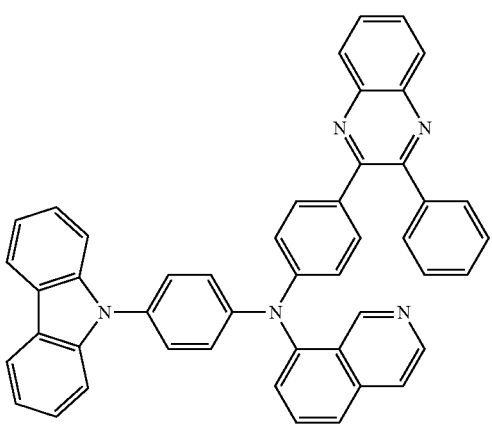
(195)

-continued
(196)
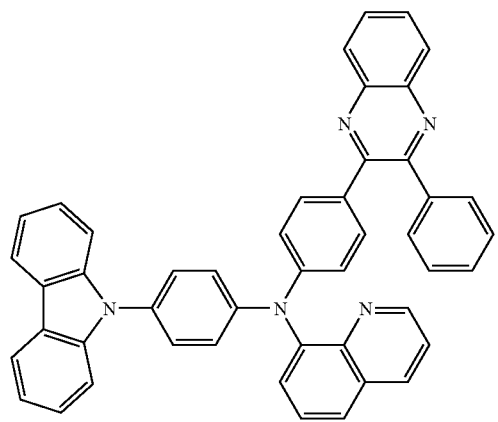
(197)
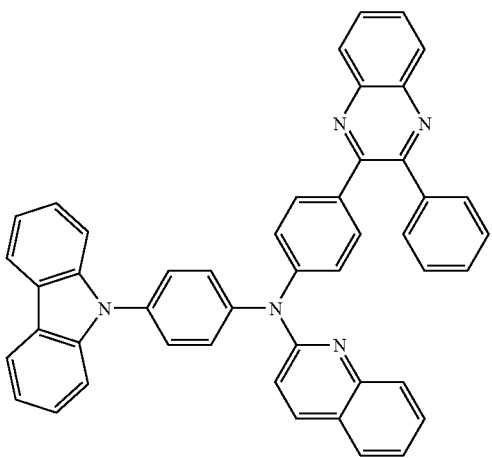
(198)
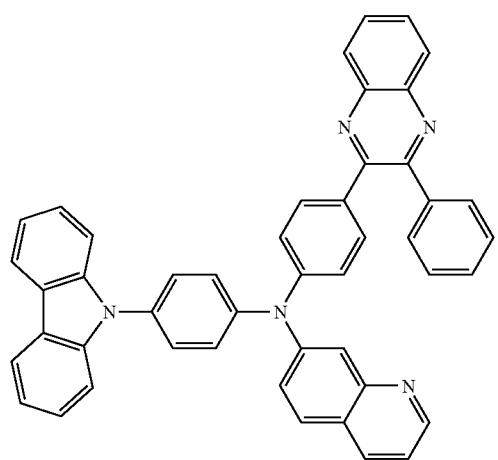
(199)
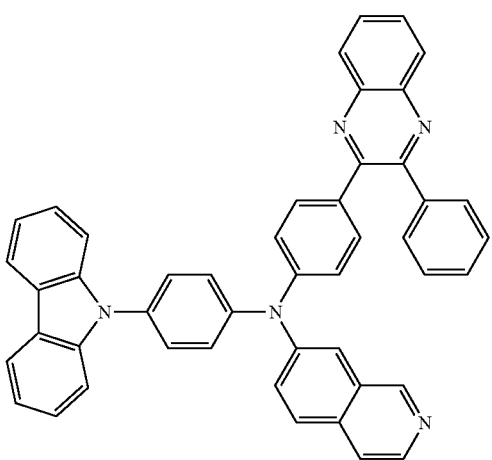
(200)
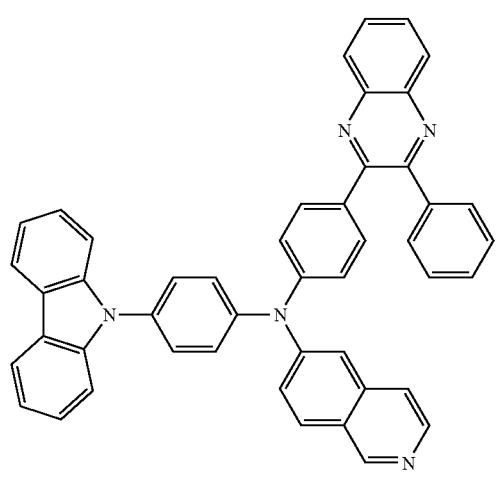
(201)
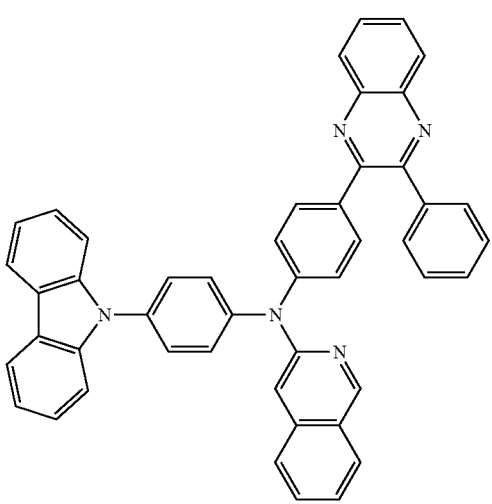

-continued
(202)
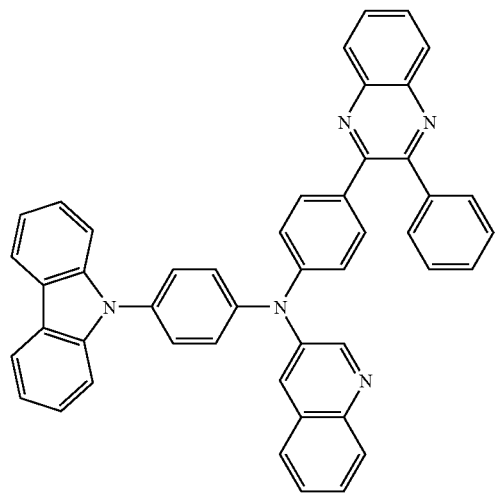
(203)
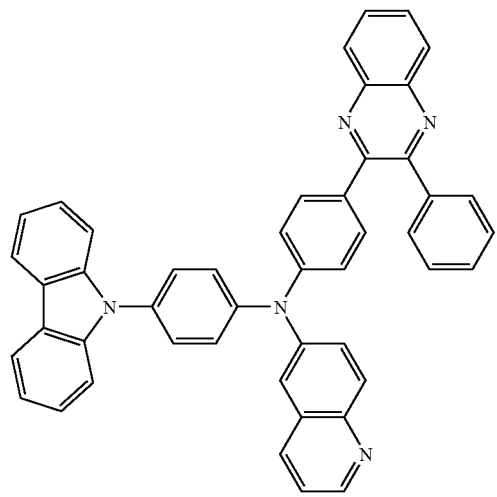
(204)
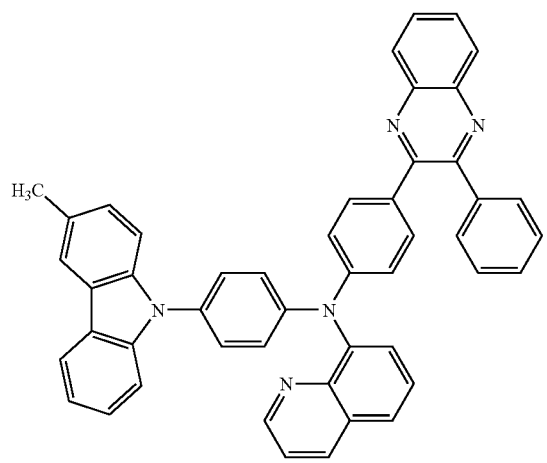
(205)
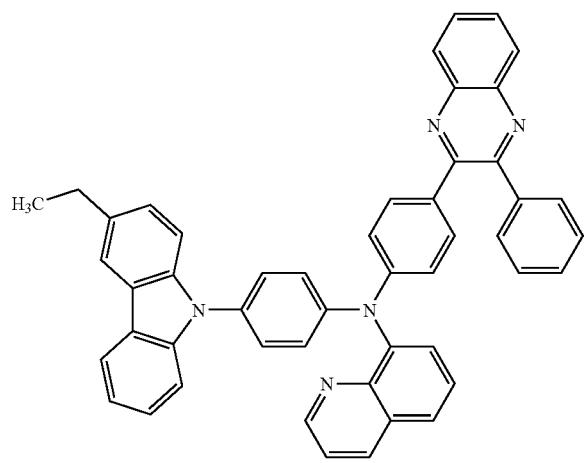
(206)
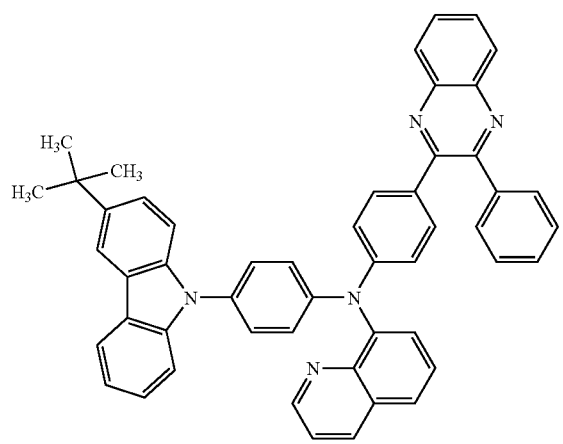
(207)
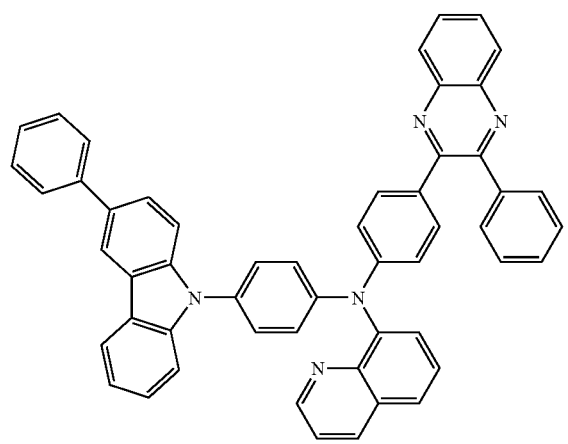

-continued
(208)
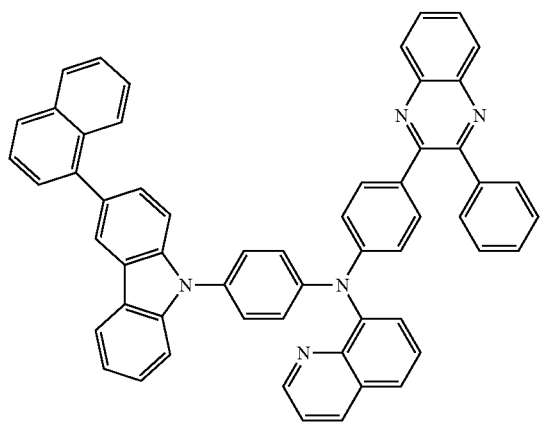
(209)
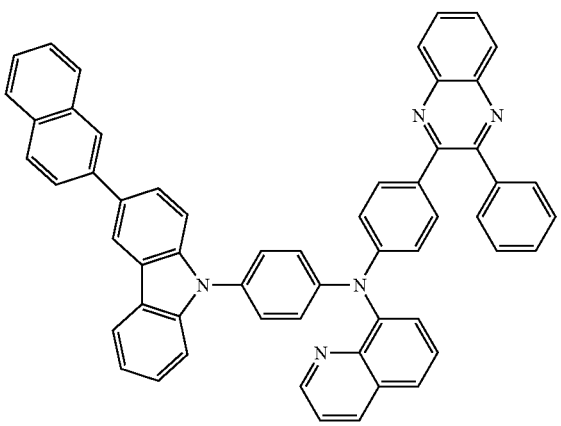
(210)
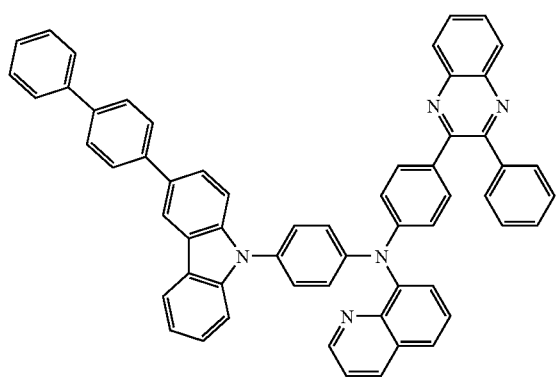
(211)
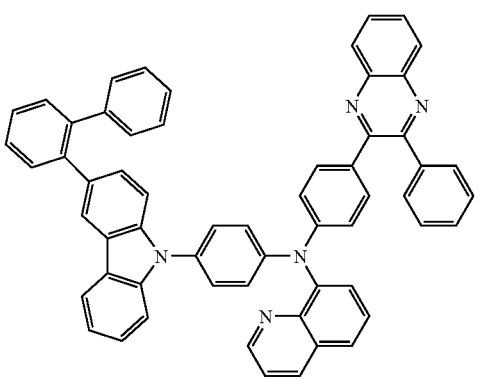
(212)
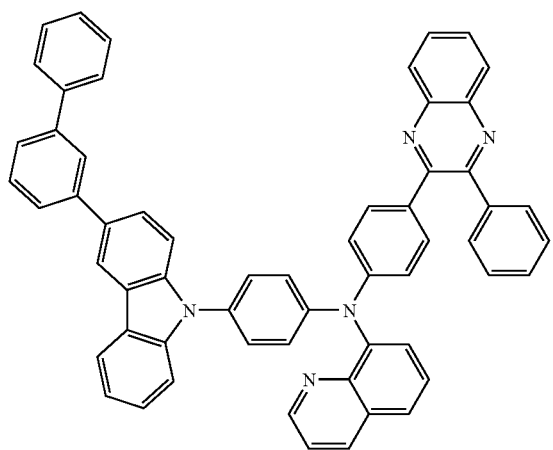

-continued
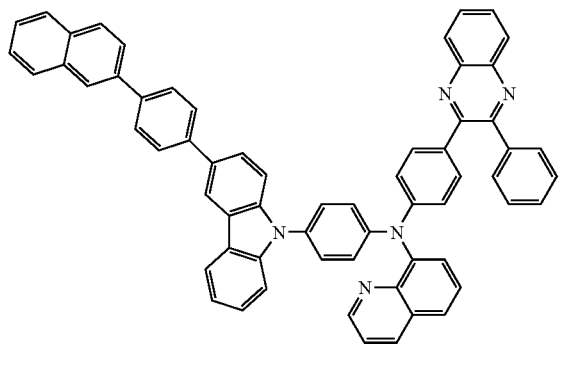
(213)
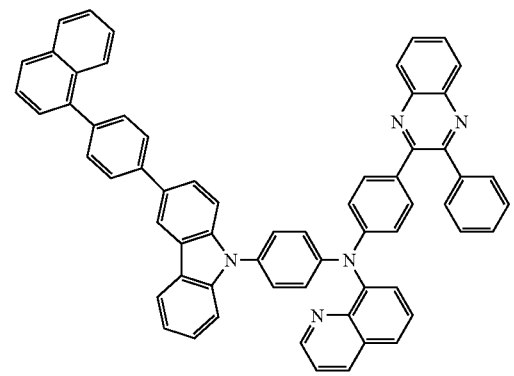
(214)
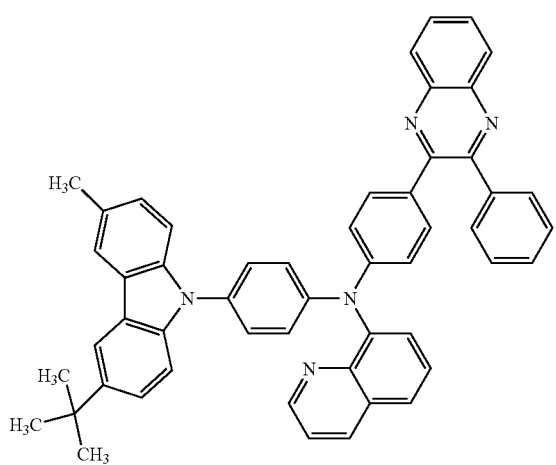
(215)
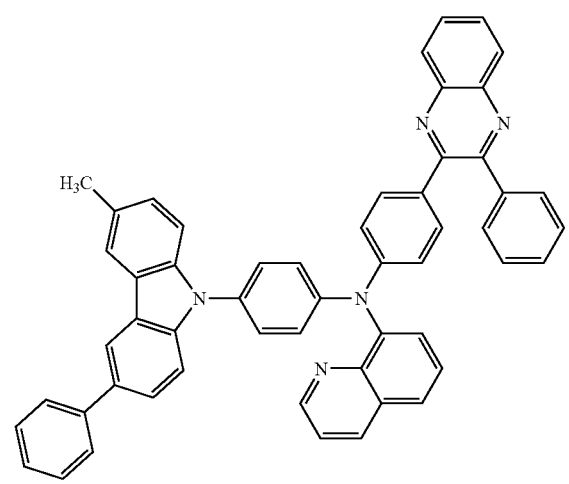
(216)
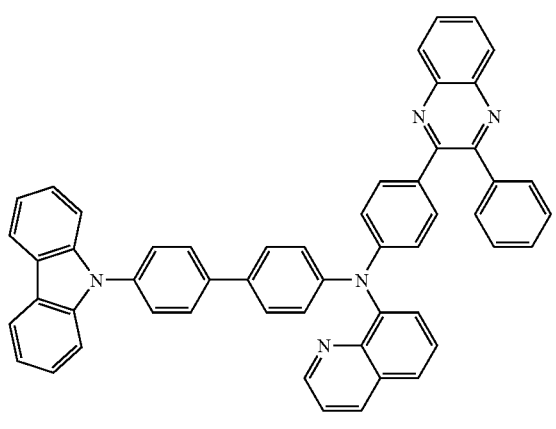
(217)
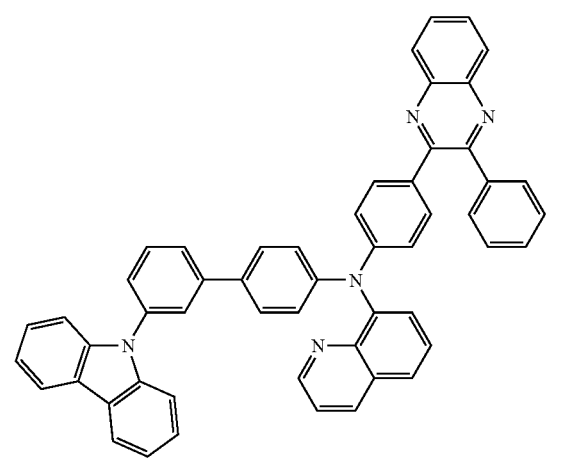
(218)

Various reactions can be applied to synthesis of the quinoxaline derivatives of this embodiment. For example, the quinoxaline derivatives represented by General Formula (G1) can be synthesized by a reaction represented by Reaction Scheme (A-1) or (B-1) below.

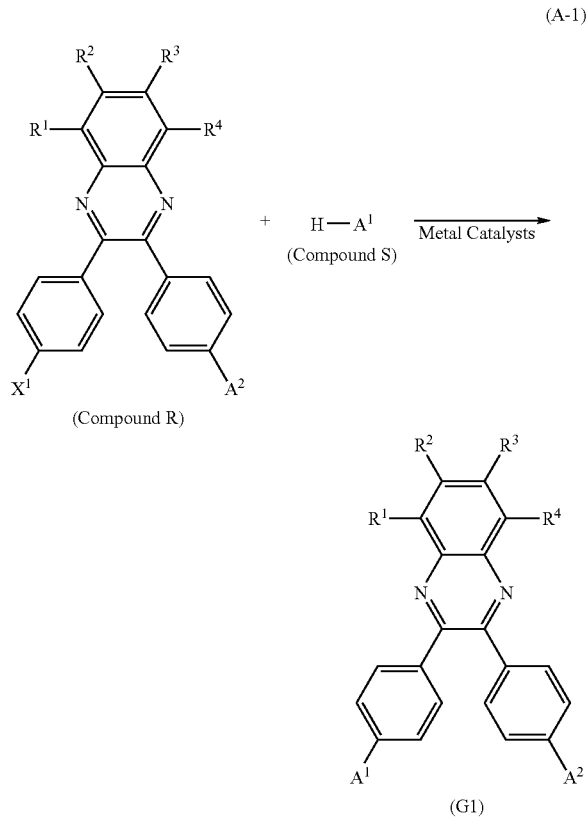

(A-1)

(Compound R) + H—A$^1$ (Compound S) →[Metal Catalysts]

(G1)

The quinoxaline derivatives of this embodiment represented by General Formula (G1) can be obtained by coupling of a halogenated quinoxaline compound (Compound R) and an amine compound (Compound S) in the presence of a base according to a Hartwig-Buchwald reaction with a palladium catalyst or according to an Ullmann reaction with copper or a copper compound (Reaction Scheme (A-1)).

In Reaction Scheme (A-1), $X^1$ represents a halogen, which is preferably iodine or bromine. $R^1$ to $R^4$ each independently represent hydrogen, an alkyl group having 1 to 4 carbon atoms, or an aryl group having 6 to 10 carbon atoms in a ring. $A^2$ represents a hydrogen atom, an alkyl group having 1 to 4 carbon atoms, an aryl group having 6 to 10 carbon atoms in a ring, or a substituent represented by General Formula (A1) below. $A^1$ represents a substituent represented by General Formula (A1) below.

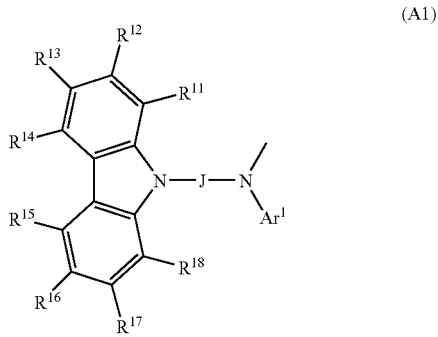

(A1)

In General Formula (A1), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring. J represents a substituted or unsubstituted arylene group having 6 to 12 carbon atoms. Note that in the case where J has a substituent, the substituent is an alkyl group having 1 to 4 carbon atoms.

In the case where the Hartwig-Buchwald reaction is performed in Reaction Scheme (A-1), a palladium catalyst which can be used may be bis(dibenzylideneacetone)palladium(0), palladium(II) acetate, or the like. Examples of ligands of the palladium catalysts which can be used in Reaction Scheme (A-1) are tri(tert-butyl)phosphine, tri(n-hexyl)phosphine, tricyclohexylphosphine, and the like. Examples of bases which can be used in Reaction Scheme (A-1) are organic bases such as sodium tert-butoxide, inorganic bases such as potassium carbonate, and the like. Examples of solvents which can be used in Reaction Scheme (A-1) are toluene, xylene, benzene, tetrahydrofuran, and the like.

The case of performing the Ullmann reaction in accordance with Reaction Scheme (A-1) is explained. Examples of copper compounds which can be used in Reaction Scheme (A-1) are copper(I) iodide, copper(II) acetate, and the like. Furthermore, copper can be used instead of copper compounds. Examples of bases which can be used in Reaction Scheme (A-1) are inorganic bases such as potassium carbonate. Examples of solvents which can be used in Reaction Scheme (A-1) are 1,3-dimethyl-3,4,5,6-tetrahydro-2(1H)pyrimidinone (DMPU), toluene, xylene, benzene, and the like. In the Ullmann reaction, the desired substance can be obtained in a shorter time and in a higher yield when the reaction temperature is 100° C. or higher; therefore, it is preferable to use DMPU or xylene that has a high boiling point. It is further preferable that the reaction temperature is higher than or equal to 150° C.; therefore, it is more preferable to use DMPU.

In the case where $A^1$ and $A^2$ are identical in General Formula (G1) and $A^1$ and $A^2$ are represented by General Formula (A1), a quinoxaline derivative can be synthesized as shown in Reaction Scheme (B-1).

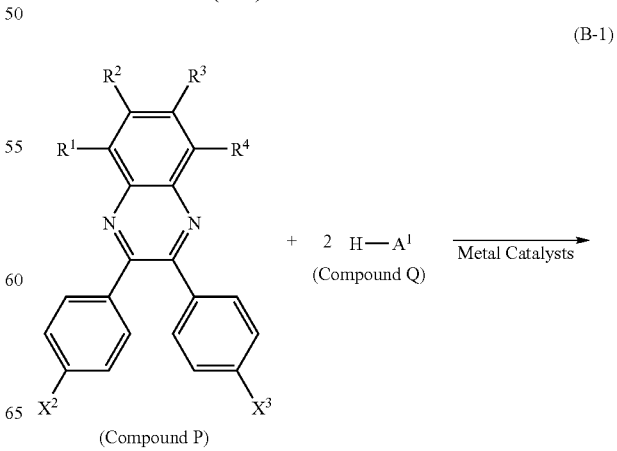

(B-1)

(Compound P) + 2 H—A$^1$ (Compound Q) →[Metal Catalysts]

-continued

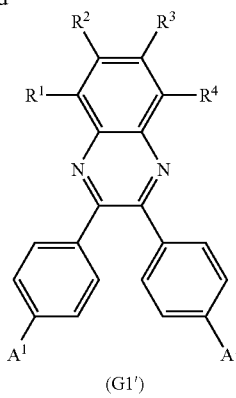

(G1')

A quinoxaline derivative of this embodiment, represented by General Formula (G1'), can be obtained by coupling of a halogenated quinoxaline compound (Compound P) and an amine compound (Compound Q) in the presence of a base according to a Hartwig-Buchwald reaction with a palladium catalyst or according to an Ullmann reaction with copper or a copper compound (Reaction Scheme (B-1)).

In Reaction Scheme (B-1), $X^2$ and $X^3$ represent a halogen, which is preferably iodine or bromine. $R^1$ to $R^4$ each independently represent hydrogen, an alkyl group having 1 to 4 carbon atoms, or an aryl group having 6 to 10 carbon atoms in a ring. $A^1$ represents a substituent represented by General Formula (A1) below.

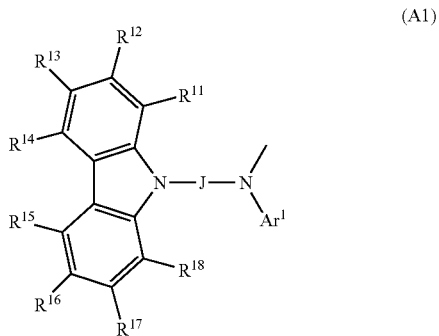

(A1)

In General Formula (A1), $Ar^1$ represents a substituted or unsubstituted heteroaryl group having 4 to 9 carbon atoms in a ring. Note that in the case where $Ar^1$ has a substituent, the substituent is an alkyl group having 1 to 4 carbon atoms, an aryl group having 6 to 10 carbon atoms in a ring, or a heteroaryl group having 4 to 9 carbon atoms in a ring. $R^{11}$ to $R^{18}$ each independently represent a hydrogen atom, an alkyl group having 1 to 4 carbon atoms, or a substituted or unsubstituted aryl group having 6 to 10 carbon atoms in a ring. Note that in the case where $R^{11}$ to $R^{18}$ have substituents, the substituents are each independently an alkyl group having 1 to 4 carbon atoms or an aryl group having 6 to 10 carbon atoms in a ring. J represents a substituted or unsubstituted arylene group having 6 to 12 carbon atoms. Note that in the case where J has a substituent, the substituent is an alkyl group having 1 to 4 carbon atoms.

In the case where the Hartwig-Buchwald reaction is performed in Reaction Scheme (B-1), a palladium catalyst which can be used may be bis(dibenzylideneacetone)palladium(0), palladium(II) acetate, or the like. Examples of ligands of the palladium catalysts which can be used in Reaction Scheme (B-1) are tri(tert-butyl)phosphine, tri(n-hexyl)phosphine, tricyclohexylphosphine, and the like. Examples of bases which can be used in Reaction Scheme (B-1) are organic bases such as sodium tert-butoxide, inorganic bases such as potassium carbonate, and the like. Examples of solvents which can be used in Reaction Scheme (B-1) are toluene, xylene, benzene, tetrahydrofuran, and the like.

The case of performing the Ullmann reaction in accordance with Reaction Scheme (B-1) is explained. Examples of copper compounds which can be used in Reaction Scheme (B-1) are copper(I) iodide, copper(II) acetate, and the like. Further, copper can be used instead of copper compounds. Examples of bases which can be used in Reaction Scheme (B-1) are inorganic bases such as potassium carbonate. Examples of solvents which can be used in Reaction Scheme (B-1) are 1,3-dimethyl-3,4,5,6-tetrahydro-2(1H)pyrimidinone (DMPU), toluene, xylene, benzene, and the like. In the Ullmann reaction, the desired substance can be obtained in a shorter time and in a higher yield when the reaction temperature is 100° C. or higher; therefore, it is preferable to use DMPU or xylene that has a high boiling point. It is further preferable that the reaction temperature is higher than or equal to 150° C.; therefore, it is more preferable to use DMPU.

Although examples of synthesis methods are described above, the quinoxaline derivatives of embodiments of the disclosed invention, represented by General Formulas (G1) to (G5), may be synthesized by any other synthesis method.

The quinoxaline derivative of an embodiment of the present invention is bipolar and excellent in both electron-transporting properties and hole-transporting properties. Thus, by using the quinoxaline derivative of an embodiment of the present invention for a light-emitting element, favorable electrical characteristics can be obtained. In addition, the quinoxaline derivative of an embodiment of the present invention has a high glass transition temperature and excellent thermal stability. Thus, by using the quinoxaline derivative of an embodiment of the present invention, a light-emitting element with excellent thermal stability can be obtained.

Embodiment 2

In this embodiment, an examples of a light-emitting element in which any of the quinoxaline derivatives described in the above embodiment is used for a light-emitting layer will be described with reference to a drawing.

FIG. 1 illustrates an example of a light-emitting element in which an EL layer 102 including a light-emitting layer 113 is interposed between a first electrode 101 and a second electrode 103.

By application of a voltage to such a light-emitting element, holes injected from the first electrode 101 side and electrons injected from the second electrode 103 side recombine in the light-emitting layer 113, whereby a light-emitting organic compound is raised to an excited state. Then, the organic compound in the excited state emits light in returning to the ground state. Note that in the light-emitting element described in this embodiment, the first electrode 101 functions as an anode and the second electrode 103 functions as a cathode. Further, in the structure illustrated in FIG. 1, the order of stacked layers may naturally be reversed.

The first electrode 101 functioning as an anode is preferably formed using a metal, an alloy, an electrically conductive compound, a mixture thereof, or the like which has a high work function (specifically, 4.0 eV or more). Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide, and the like. Other than these, there are gold (Au), platinum (Pt), nickel (Ni), tungsten (W), chromium (Cr), molybdenum (Mo), iron (Fe), cobalt (Co), copper (Cu), palladium (Pd), titanium (Ti), and the like.

Note that, when a layer of the EL layer 102 which is in contact with the first electrode 101 is formed using a composite material of an organic compound and an electron acceptor, a substance used for the first electrode 101 can be selected without being limited by the work function. For example, aluminum (Al), silver (Ag), an alloy including aluminum (e.g., Al—Si), or the like can also be used.

Note that the first electrode 101 can be formed by, for example, a sputtering method, an evaporation method (including a vacuum evaporation method), or the like.

The EL layer 102 formed over the first electrode 101 includes at least the light-emitting layer 113 and is formed to include any of the quinoxaline derivatives described in the above embodiment. The EL layer 102 can also include a known substance as a part, for which either a low molecular compound or a high molecular compound may be used. Note that the substances forming the EL layer 102 may include an inorganic compound as a part.

Further, as illustrated in FIG. 1, the EL layer 102 includes not only the light-emitting layer 113 but also an appropriate combination of the following layers: a hole-injection layer 111 including a substance having a high hole-injecting property, a hole-transport layer 112 including a substance having a high hole-transporting property, an electron-transport layer 114 including a substance having a high electron-transporting property, an electron-injection layer 115 including a substance having a high electron-injecting property, and the like.

The hole-injection layer 111 includes a substance having a high hole-injecting property. As the substance having a high hole-injecting property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Alternatively, any of the following aromatic amine compounds which are low molecular organic compounds can be used: 4,4',4''-tris(N,N-diphenylamino)triphenylamine (abbreviation: 1 DATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Further, a high molecular compound (such as an oligomer, a dendrimer, or a polymer) can be used. For example, any of the following high molecular compounds can be used: poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), poly[N,N'-bis(4-butylphenyl)-N,N'-bis(phenyl)benzidine] (abbreviation: Poly-1PD), and the like. Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Alternatively, for the hole-injection layer 111, a composite material formed by mixing an organic compound and an electron acceptor may be used. Such a composite material has excellent hole-injecting and hole-transporting properties because the electron acceptor produces holes in the organic compound. In this case, as the organic compound, a material that can efficiently transport the produced holes (a substance having a high hole-transporting property) is preferably used.

The organic compound used for the above composite material preferably has a high hole-transporting property. Specifically, a substance having a hole mobility of $10^{-6}$ $cm^2/Vs$ or higher is preferably used. Specific examples of organic compounds that can be used for the composite material are given below.

Examples of the organic compounds that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), and N,N'-bis(3-methylphenyl)-N,N'-diphenyl-[1,1'-biphenyl]-4,4'-diamine (abbreviation: TPD) and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene.

Any of the following aromatic hydrocarbon compounds may be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, and 2,3,6,7-tetramethyl-9,10-di(1-naphthyl)anthracene.

Any of the following aromatic hydrocarbon compounds may also be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Any of the quinoxaline derivatives described in Embodiment 1 may also be used.

Examples of electron acceptors that can be used for the composite material include organic compounds such as 7,7,8,8-tetracyano-2,3,5,6-tetrafluoroquinodimethane (abbreviation: $F_4$-TCNQ) and chloranil, transition metal oxides, and the like. Oxides of metals belonging to Groups 4 to 8 of the periodic table may also be used. For example, vanadium oxide, niobium oxide, tantalum oxide, chromium oxide, molybdenum oxide, tungsten oxide, manganese oxide, and rhenium oxide are suitable because of their high electron-accepting properties. Among these, molybdenum oxide is suitable because it is easy to handle due to its stability in air and its low hygroscopic property.

Note that a composite material formed using any of the above-mentioned high molecular compounds such as PVK, PVTPA, PTPDMA, and Poly-TPD and any of the above-mentioned electron acceptors may be used for the hole-injection layer 111.

The hole-transport layer 112 includes a substance having a high hole-transporting property. As a substance having a high hole-transporting property, there are aromatic amine compounds such as NPB, TPD, 4,4'-bis[N-(9,9-dimethylfluoren-2-yl)-N-phenylamino]biphenyl (abbreviation: DFLDPBi), and 4,4'-bis[N-(Spiro-9,9'-bifluoren-2-yl)-N-phenylamino]biphenyl (abbreviation: BSPB). The substances mentioned here are mainly substances which have a hole mobility of $10^{-6}$ $cm^2/Vs$ or higher. Note that the hole-transport layer 112 may have a single-layer structure or a stacked-layer structure.

Further alternatively, for the hole-transport layer 112, a high molecular compound such as PVK, PVTPA, PTPDMA, or Poly-TPD can be used.

The quinoxaline derivatives described in Embodiment 1 can be used as hole-transport materials because they are bipolar and have a hole-transporting property.

The light-emitting layer 113 includes a substance having a high light-emitting property. Note that in this embodiment, a description is given of an example in which any of the quinoxaline derivatives described in the above embodiment is used for the light-emitting layer. The above quinoxaline derivatives are suitably used as a host material in a light-emitting layer where a substance having a high light-emitting property (guest material) is dispersed in another substance (host material). However, embodiments of the disclosed invention are not to be construed as being limited to this structure. Any of quinoxaline derivatives of an embodiment of the present invention may be used alone in the light-emitting layer.

In the case where any of the quinoxaline derivatives described in the above embodiment is used as a host material and a material that emits fluorescence is used as a guest material, it is preferable to use, as the guest material, a material whose lowest unoccupied molecular orbital (LUMO) level is lower and highest occupied molecular orbital (HOMO) level is higher than those of the quinoxaline derivatives described in the above embodiment. Examples of materials for yellow light emission include rubrene, 5,12-bis(1,1'-biphenyl-4-yl)-6,11-diphenyltetracene (abbreviation: BPT), and the like. Furthermore, examples of materials for red light emission include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Alternatively, in the case where any of the quinoxaline derivatives described in the above embodiment is used as a host material and a material that emits phosphorescence is used as a guest material, it is preferable to use, as the guest material, a material whose triplet excitation energy is lower than that of the quinoxaline derivatives described in the above embodiment. Examples of such materials include organometallic complexes such as bis[2-(2'-benzo[4,5-α]thienyl)pyridinato-N,$C^3$]iridium(III) acetylacetonate (abbreviation: Ir(btp)$_2$(acac)), bis(1-phenylisoquinolinato-N,$C^{2'}$)iriidium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), (2,3,7,8,12,13,17,18-octaethyl-21H,23H-porphyrin) platinum(III) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

The quinoxaline derivatives described in the above embodiment are bipolar and have an electron-transporting property, with which a light-emitting layer having an excellent electron-transporting property can be obtained. A light-emitting layer of such a structure can provide highly efficient light emission when a guest material having a high electron-trapping property is used.

In addition, as a substance (host material) in which a light-emitting substance (guest material) is dispersed, plural kinds of substances can be used. Therefore, the light-emitting layer may include a second host material in addition to any of the quinoxaline derivatives described in the above embodiment.

Further, any of the above quinoxaline derivatives described in Embodiment 1 can be used alone as a light-emitting substance, or as a guest material.

The electron-transport layer 114 includes a substance having a high electron-transporting property. For the electron-transport layer 114, it is possible to use a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$). Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridine-diyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances mentioned here are mainly substances which have an electron mobility of $10^{-6}$ $cm^2/Vs$ or higher.

Any of the quinoxaline derivatives described in Embodiment 1 may also be used for the electron-transport layer.

In addition, the electron-transport layer 114 may have a single-layer structure or a stacked-layer structure.

The electron-injection layer 115 includes a substance having a high electron-injecting property. For the electron-injection layer 115, an alkali metal, an alkaline earth metal, or a compound thereof, such as lithium (Li), cesium (Cs), calcium (Ca), lithium fluoride (LiF), cesium fluoride (CsF), calcium fluoride (CaF$_2$), or lithium oxide (LiO$_x$), can be used. Alternatively, a rare earth metal compound such as erbium fluoride (ErF$_3$) can also be used. Further alternatively, any of the above-mentioned substances that are used to form the electron-transport layer 114 may be used.

For the electron-injection layer 115, a composite material formed by mixing an organic compound and an electron donor may be used. Such a composite material has excellent electron-injecting and electron-transporting properties because the electron donor produces electrons in the organic compound. In this case, as the organic compound, a material that can efficiently transport the produced electrons is preferably used; for example, any of the above-mentioned substances that are used to form the electron-transport layer 114 can be used. Any of the quinoxaline derivatives of an embodiment of the present invention may also be used. Further, as the electron donor, a substance exhibiting an electron-donating property to the organic compound is used. Specifically, it is preferable to use any of alkali metals, alkaline earth metals, or rare earth metals, such as lithium, cesium, magnesium, calcium, erbium, ytterbium, or the like. Alternatively, it is preferable to use any of alkali metal oxides or alkaline earth metal oxides, such as lithium oxide, calcium oxide, or barium oxide. A Lewis base such as magnesium oxide can also be used. Alternatively, an organic compound such as tetrathiafulvalene (abbreviation: TTF) can be used.

Note that the hole-injection layer 111, hole-transport layer 112, light-emitting layer 113, electron-transport layer 114, and electron-injection layer 115 which are described above can each be formed by an evaporation method (including a vacuum evaporation method), an inkjet method, a coating method, or the like.

The second electrode 103 functioning as a cathode is preferably formed using a metal, an alloy, an electrically conductive compound, a mixture thereof, or the like which has a low work function (preferably, 3.8 eV or lower). Specifically, any of the following materials can be used: aluminum, silver, and the like, as well as elements that belong to Group 1 or Group 2 of the periodic table, that is, alkali metals such as lithium and cesium or alkaline earth metals such as magnesium, calcium, and strontium, or alloys thereof; rare earth metals such as europium and ytterbium, or alloys thereof.

Note that, when a layer of the EL layer 102 which is in contact with the second electrode 103 is formed using the above-described composite material of the organic compound and the electron donor, a material used for the second electrode 103 can be selected without being limited by the work function. For example, any of a variety of conductive materials such as aluminum, silver, ITO, and indium oxide-tin oxide containing silicon or silicon oxide can be used.

Note that the second electrode 103 can be formed by a vacuum evaporation method or a sputtering method. Alternatively, when a silver paste or the like is used, a coating method, an inkjet method, or the like may be used.

In the above-described light-emitting element, holes and electrons generated by a potential difference between the first electrode 101 and the second electrode 103 recombine in the EL layer 102, whereby light is emitted. Then, this emitted light is extracted through either of the first electrode 101 or the second electrode 103, or both. Accordingly, either the first electrode 101 or the second electrode 103 or both have a visible-light-transmitting property.

Note that with the use of the light-emitting element described in this embodiment, a passive-matrix light-emitting device or an active-matrix light-emitting device in which drive of the light-emitting element is controlled by a thin film transistor (TFT) can be fabricated.

Note that there is no particular limitation on the structure of the TFT in the case of fabricating an active-matrix light-emitting device. Further, either an n-type TFT or a p-type TFT may be used. Furthermore, there is no particular limitation on a semiconductor material used for the TFT. For example, any of the following materials can be used: silicon-based semiconductor materials (which may be amorphous, crystalline, or single crystal), germanium-based semiconductor materials, chalcogenide-based semiconductor materials, or any other semiconductor materials. Obviously, an oxide semiconductor material may be used.

In this embodiment, any of the above-described quinoxaline derivatives is used to form the light-emitting layer 113. Accordingly, a light-emitting element with high current efficiency can be provided.

Note that this embodiment can be combined as appropriate with any structure described in the other embodiments.

Embodiment 3

A light-emitting element which is one embodiment of the disclosed invention may have a plurality of light-emitting layers. By producing light emission from each of the plurality of light-emitting layers, mixed light can be obtained. White light emission can thus be obtained, for example. In this embodiment, one embodiment of a light-emitting element having a plurality of light-emitting layers is described with reference to a drawing.

Figure 2:
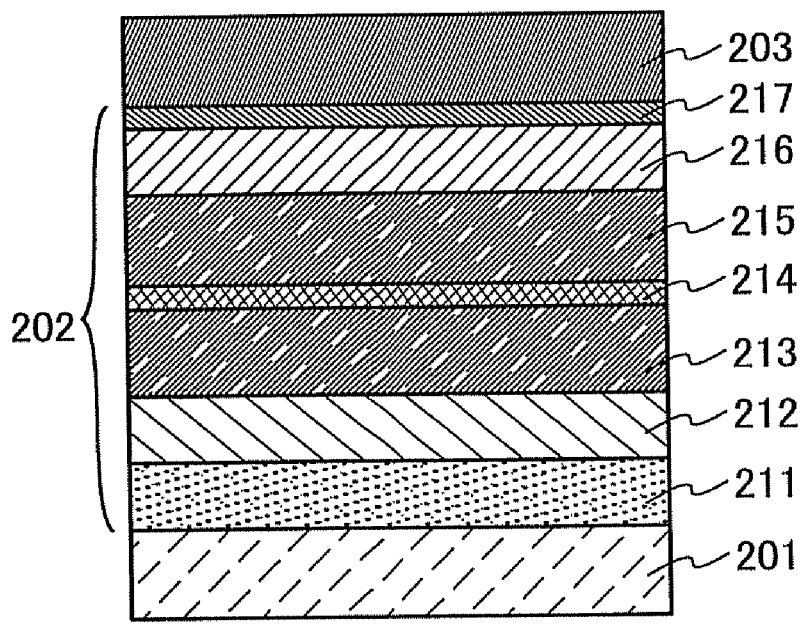
FIG. 2 illustrates a light-emitting element.

In FIG. 2, an EL layer 202 including a first light-emitting layer 213 and a second light-emitting layer 215 is provided between a first electrode 201 and a second electrode 203, and emission of light that is a mixture of light emitted from the first light-emitting layer 213 and light emitted from the second light-emitting layer 215 can be obtained. A separation layer 214 is preferably provided between the first light-emitting layer 213 and the second light-emitting layer 215.

When a voltage is applied such that the potential of the first electrode 201 becomes higher than that of the second electrode 203, a current flows between the first electrode 201 and the second electrode 203, and holes or electrons move to the first light-emitting layer 213, the second light-emitting layer 215, or the separation layer 214. Accordingly, a first light-emitting substance included in the first light-emitting layer 213 and a second light-emitting substance included in the second light-emitting layer 215 are raised to an excited state. Then, the light-emitting substances in the excited state emit light in returning to the ground state.

The first light-emitting layer 213 includes the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)gallium chloride (abbreviation: $Gamq_2Cl$) or a phosphorescent compound such as bis{2-[3,5-bis(trifluoromethyl)phenyl]pyridinato-N,$C^{2'}$}iridium(III) picolinate (abbreviation: $Ir(CF_3 \ ppy)_2(pic)$), bis[2-(4,6-difluorophenyppyridinato-N,$C^{2'}$]iridium(III) acetylacetonate (abbreviation: FIr(acac)), bis[2-(4,6-difluorophenyppyridinato-N,$C^{2'}$]iridium(III) picolinate (abbreviation: FIrpic), or bis[2-(4,6-difluorophenyppyridinato-N,$C^{2'}$]iridium(III) tetra (1-pyrazolyl)borate (abbreviation: FIr6), from which light emission with a peak at 450 nm to 510 nm in an emission spectrum (i.e., blue light to blue green light) can be obtained.

When a fluorescent compound is used as the first light-emitting substance, the first light-emitting layer 213 preferably has a structure in which a substance having larger singlet excited energy than the first light-emitting substance is used as a first host and the first light-emitting substance is dispersed as a guest. Alternatively, when a phosphorescent compound is used as the first light-emitting substance, the first light-emitting layer 213 preferably has a structure in which a substance having larger triplet excited energy than the first light-emitting substance is used as a first host and the first light-emitting substance is dispersed as a guest. As the first host, NPB, CBP, TCTA, or the like, which is described above, or DNA, t-BuDNA, or the like can be used. Note that the singlet excitation energy refers to an energy difference between a ground state and a singlet excited state. In addition, the triplet excitation energy refers to an energy difference between a ground state and a triplet excited state.

On the other hand, the second light-emitting layer 215 includes any of the quinoxaline derivatives described in the above embodiment. The structure of the second light-emitting layer 215 may be similar to that of the light-emitting layer 113 which is described in the above embodiment.

In addition, the separation layer 214 can be formed using, for example, TPAQn, NPB, CBP, TCTA, Znpp$_2$, ZnBOX, or the like mentioned above. The separation layer 214 as described above can prevent an undesirable increase in the emission intensity of only one of the first light-emitting layer 213 and the second light-emitting layer 215. Note that the separation layer 214 is not an essential component. The separation layer 214 may be provided in the case where the ratio of the emission intensity of the first light-emitting layer 213 to that of the second light-emitting layer 215 needs to be adjusted. Further, any of the quinoxaline derivatives of an embodiment of the disclosed invention may be used for the separation layer 214.

Note that in this embodiment, any of the quinoxaline derivatives described in the above embodiment is used for the second light-emitting layer 215, while another light-emitting substance is used for the first light-emitting layer 213. However, any of the quinoxaline derivatives described in the above embodiment may be used for the first light-emitting layer 213, while another light-emitting substance may be used for the second light-emitting layer 215.

Further, although a light-emitting element including two light-emitting layers is described in this embodiment, the number of light-emitting layers is not limited to two and may be three or more.

Note that the first electrode 201 may have a structure similar to that of the first electrode 101 which is described in the above embodiment. Also, the second electrode 203 may have a structure similar to that of the second electrode 103 which is described in the above embodiment.

Further, in this embodiment, a description is given of an example in which a hole-injection layer 211, a hole-transport layer 212, an electron-transport layer 216, and an electron-injection layer 217 are provided. These layers may have structures similar to those described in the above embodiment. Note that they are not essential components. These layers may be provided depending on element characteristics.

Note that this embodiment can be combined as appropriate with any structure described in the other embodiments.

Embodiment 4

In this embodiment, a light-emitting element having a plurality of EL layers (hereinafter referred to as a stacked-type element) is described with reference to a drawing.

Figure 3:
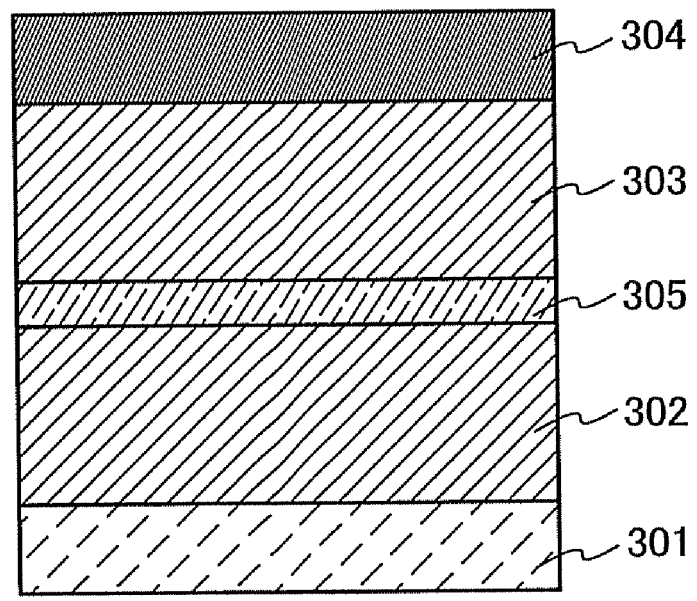
FIG. 3 illustrates a light-emitting element

FIG. 3 illustrates a stacked-type light-emitting element which has a plurality of EL layers (a first EL layer 302 and a second EL layer 303) between a first electrode 301 and a second electrode 304. Note that although a structure in which two EL layers are provided is described in this embodiment, three or more EL layers may be provided.

In this embodiment, the first electrode 301 functions as an anode, and the second electrode 304 functions as a cathode. Note that the first electrode 301 and the second electrode 304 may have structures similar to those described in the above embodiments. Further, the plurality of EL layers (the first EL layer 302 and the second EL layer 303) may have structures similar to any of those of the EL layers described in the above embodiments, or may have structures in which any of the layers is different. In other words, the first EL layer 302 and the second EL layer 303 may have the same structure or different structures.

Further, a charge-generation layer 305 is provided between the plurality of EL layers (the first EL layer 302 and the second EL layer 303). The charge-generation layer 305 functions to inject electrons into one of the EL layers and inject holes into the other of the EL layers when a voltage is applied between the first electrode 301 and the second electrode 304. In this embodiment, when a voltage is applied such that the potential of the first electrode 301 becomes higher than that of the second electrode 304, the charge-generation layer 305 injects electrons into the first EL layer 302 and injects holes into the second EL layer 303.

Note that the charge-generation layer 305 preferably has a visible-light-transmitting property in view of light extraction efficiency. Further, the electrical conductivity of the charge-generation layer 305 may be lower than that of the first electrode 301 or the second electrode 304.

The charge-generation layer 305 may have either a structure including an organic compound with a high hole-transporting property and an electron acceptor or a structure including an organic compound with a high electron-transporting property and an electron donor. Alternatively, both of these structures may be stacked.

The description in the above embodiment can be referred to for details of the organic compound with a high hole-transporting property and the electron acceptor. Also, the description in the above embodiment can be referred to for details of the organic compound with a high electron-transporting property and the electron donor.

When the charge-generation layer 305 is formed using the above-mentioned material, an increase in drive voltage which is caused when the EL layers are stacked can be suppressed.

By an arrangement in which the charge-generation layer separates the plurality of EL layers, as in the light-emitting element according to this embodiment, luminance can be increased while current density is kept low. Thus, a light-emitting element which can emit light with high luminance and has long lifetime can be achieved.

Further, by forming the EL layers to emit light of different colors, an emission color that is provided by the light-emitting element as a whole can be controlled. For example, by forming a light-emitting element having two EL layers such that the emission color of the first EL layer and the emission color of the second EL layer are complementary colors, the light-emitting element can provide white light emission as a whole.

In addition, when a plurality of different EL layers are provided as described above, a light-emitting element having a broad emission spectrum can be easily provided. For example, a light-emitting element having a first EL layer which emits red light, a second EL layer which emits green light, and a third EL layer which emits blue light is a light-emitting element which emits white light as a whole and has an excellent color rendering property.

Note that the structure described in this embodiment can be combined as appropriate with any of the structures described in the other embodiments.

Embodiment 5

In this embodiment, a description is given of a passive-matrix light-emitting device and an active-matrix light-emitting device each of which uses a light-emitting element, as one embodiment of the disclosed invention.

FIGS. 4A to 4D and FIG. 5 show examples of passive-matrix light-emitting devices.

In a passive-matrix (also called simple-matrix) light-emitting device, a plurality of anodes arranged in stripes (in stripe form) are provided orthogonal to a plurality of cathodes arranged in stripes. Light-emitting layers are formed at the intersections. Therefore, light is emitted from a light-emitting layer (hereinafter, referred to as a pixel) at an intersection of an anode selected (to which a voltage is applied) and a cathode selected.

Figure 4A:
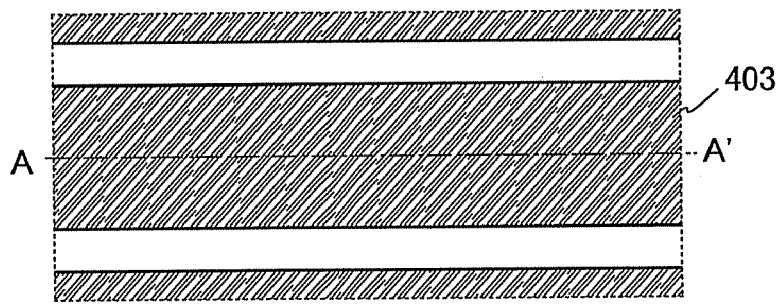
FIGS. 4A to 4D illustrate a passive-matrix light-emitting device.
Figure 4B:
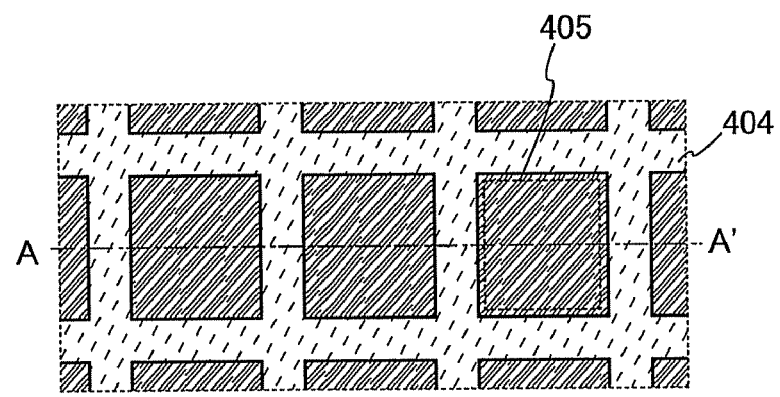
Figure 4C:
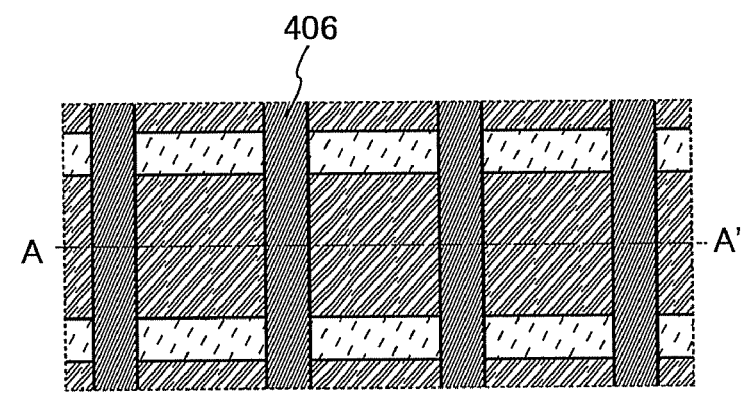
Figure 4D:
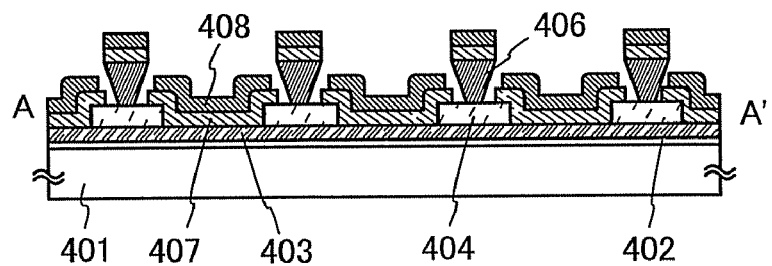

FIGS. 4A to 4C are top views of a pixel portion before sealing. FIG. 4D is a cross-sectional view taken along dashed line A-A' in FIGS. 4A to 4C.

Over a substrate 401, an insulating layer 402 is formed as a base insulating layer. Note that the base insulating layer is not an essential component and thus may be formed as needed. A plurality of first electrodes 403 are arranged at regular intervals over the insulating layer 402 (see FIG. 4A).

In addition, a partition 404 having openings in regions corresponding to pixels is provided over the first electrodes 403. The partition 404 having openings is formed using an organic material (polyimide, acrylic, polyamide, polyimide amide, resist, or benzocyclobutene), an inorganic material (e.g., $SiO_x$ including an alkyl group), or the like. Note that openings 405 corresponding to the pixels serve as light-emitting regions (see FIG. 4B).

Over the partition 404, a plurality of partitions 406 are provided so as to intersect with the first electrodes 403 (see FIG. 4C). The partitions 406 are each reversely tapered and arranged in parallel to one another.

In regions over the first electrodes 403 where the partitions 406 are not formed, EL layers 407 and second electrodes 408 are provided in that order (see FIG. 4D). Here, the EL layers 407 and the second electrodes 408 are separated, which are electrically isolated from each other. Such a structure can be obtained when the height of the partitions 406 is set larger than the sum of the thicknesses of the EL layers 407 and the second electrodes 408.

The second electrodes 408 extend in the direction in which they intersect with the first electrodes 403. Note that over the partitions 406, layers of the same material as the EL layers 407 and layers of the same material as the second electrodes 408 are also formed, which are isolated from the EL layers 407 and the second electrodes 408.

Note that the first electrode 403 and the second electrode 408 may serve as an anode and a cathode, respectively, or vice versa. The stack structure of the EL layer 407 is adjusted depending on the polarity of the electrodes, as appropriate.

Further, the substrate 401 may be sealed so that a light-emitting element is provided in a sealed space. Sealing is carried out with an adhesive such as a seal material to attach the substrate 401 to a sealing can or a sealant. Such sealing can suppress deterioration of the light-emitting element. Note that the sealed space may be filled with a filler, a dry inert gas, a drying agent (a desiccant), or the like. Sealing a drying agent in the space enables removal of a minute amount of moisture, whereby deterioration of the light-emitting element which is caused by moisture is suppressed. Note that as a drying agent, a substance that adsorbs moisture by chemical adsorption can be used. For example, oxides of alkaline earth metals such as calcium oxide and barium oxide can be used. Alternatively, a substance that adsorbs moisture by physical adsorption, such as zeolite or silicagel, may be used.

Figure 5:
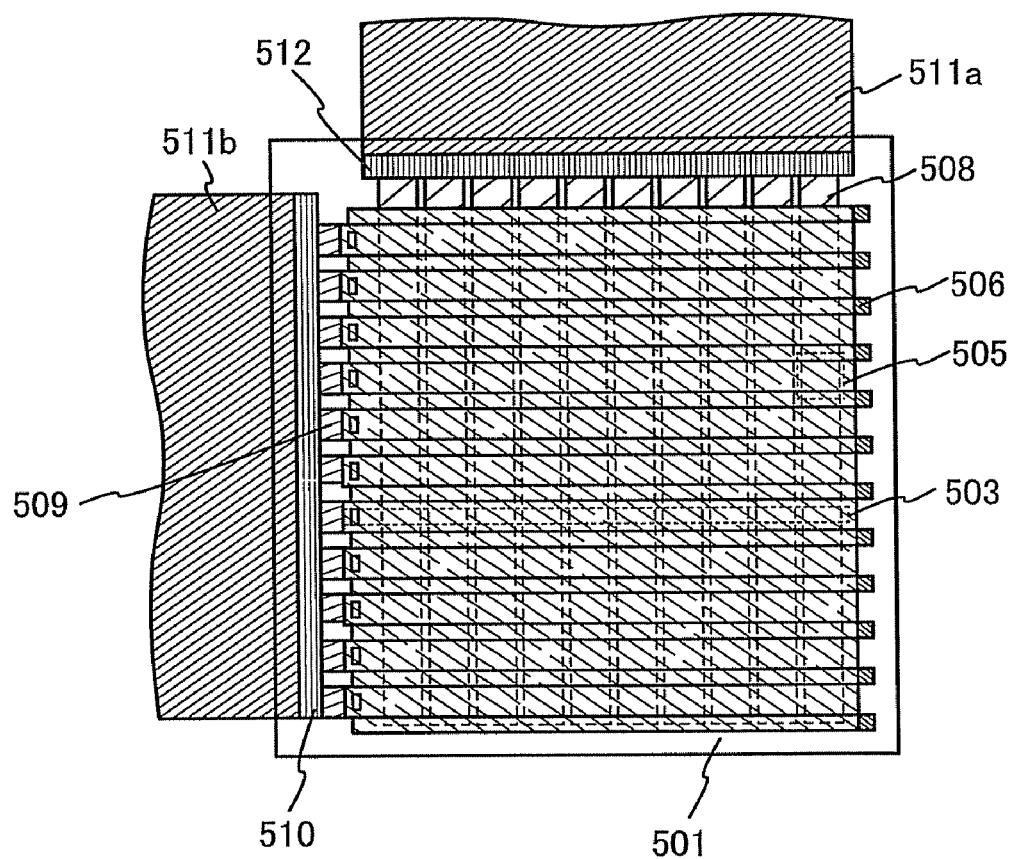
FIG. 5 illustrates a passive-matrix light-emitting device.

Next, FIG. 5 illustrates a structure of a passive-matrix light-emitting device as illustrated in FIGS. 4A to 4D, on which an FPC and the like are mounted.

In a pixel portion in FIG. 5, scan lines and data lines are arranged to intersect with each other so that they are orthogonal to each other. Note that the first electrodes 403 in FIGS. 4A to 4D correspond to scan lines 503 in FIG. 5, the second electrodes 408 in FIGS. 4A to 4D correspond to data lines 508 in FIG. 5, and the partitions 406 in FIGS. 4A to 4D correspond to partitions 506 in FIG. 5. An EL layer is formed between the data line 508 and the scan line 503, and a region 505 corresponds to one pixel.

Note that the scan lines 503 are electrically connected at their ends to connection wirings 509, and the connection wirings 509 are connected to an FPC 511b through an input terminal 510. The data lines 508 are connected to an FPC 511a through an input terminal 512.

A surface where light is extracted may be provided with an optical film such as a polarizing plate, a circularly polarizing plate (including an elliptically polarizing plate), a retardation plate (a quarter-wave plate or a half-wave plate), a color filter, or an anti-reflection film. In addition, the surface where light is extracted or a surface of the various films may be subjected to treatment. For example, by forming a slightly uneven surface, the surface diffuses reflected light and reduces glare.

Note that although FIG. 5 illustrates the example in which an IC chip including a driver circuit is not provided over the substrate, an IC chip may be mounted on the substrate. As a method for mounting an IC chip, a COG method, a wire bonding method, TCP, or the like can be used.

Figure 6A:
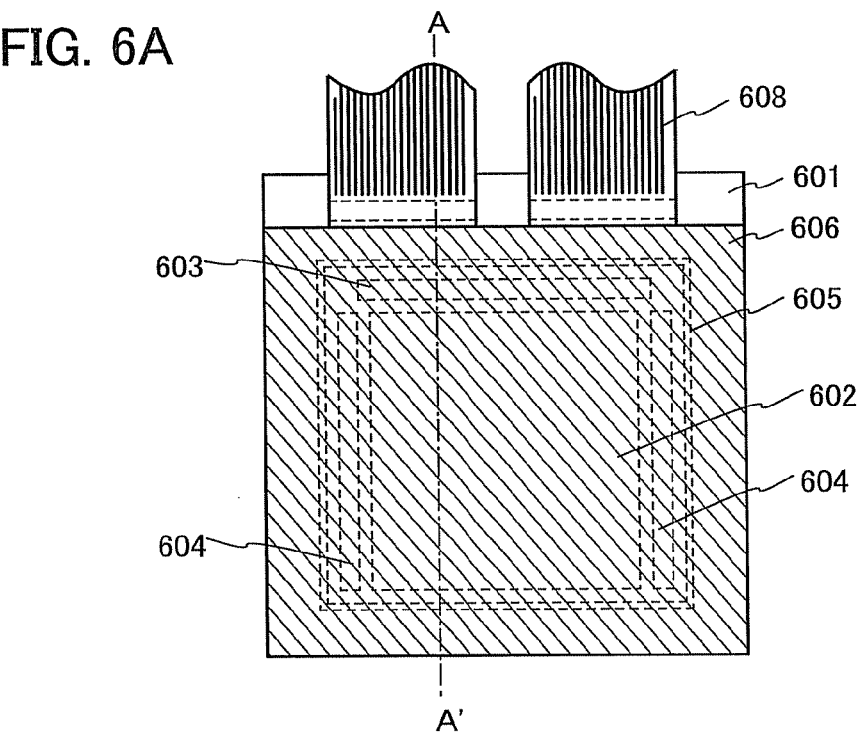
FIGS. 6A and 6B illustrate an active-matrix light-emitting device.
Figure 6B:
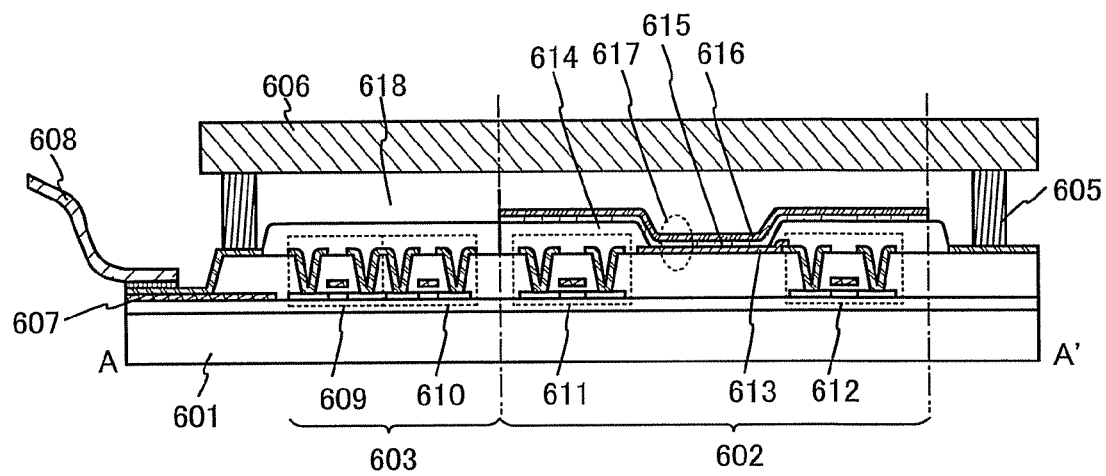

FIGS. 6A and 6B illustrate an example of an active-matrix light-emitting device.

FIG. 6A is a top view of the light-emitting device. FIG. 6B is a cross-sectional view taken along dashed line A-A' in FIG. 6A.

The active-matrix light-emitting device of this embodiment includes a pixel portion 602, a driver circuit portion 603 (a source side driver circuit), and a driver circuit portion 604 (a gate side driver circuit) which are provided over an element substrate 601. The pixel portion 602, the driver circuit portion 603, and the driver circuit portion 604 are sealed between the element substrate 601 and a sealing substrate 606 with a sealant 605 (see FIG. 6A).

In addition, over the element substrate 601, a lead wiring 607 for connecting an external input terminal is provided. Note that an example is described here in which a flexible printed circuit (FPC) is provided as the external input terminal. Although only an FPC 608 is illustrated in FIGS. 6A and 6B, this FPC may be provided with a printed wiring board (PWB). The term "light-emitting device" in this specification and the like includes not only a light-emitting device body but also a light-emitting device to which an FPC, a PWB, or the like is attached.

In the driver circuit portion 603, a CMOS circuit is formed by combining an n-channel TFT 609 and a p-channel TFT 610 (see FIG. 6B). It is needless to say that the circuit configuration is not limited to this example, and any of various circuits such as CMOS circuits, PMOS circuits, or NMOS circuits can be applied. In addition, although a driver circuit-integrated type where the driver circuit is formed over the substrate is described in this embodiment, the present invention is not to be construed as being limited to this structure. The driver circuit can be formed outside. Note that FIG. 6B shows only the driver circuit portion 603 which is the source side driver circuit and the pixel portion 602.

The pixel portion 602 has a plurality of pixels each of which includes a switching TFT 611, a current control TFT 612, and an anode 613 which is electrically connected to an electrode (a source electrode or a drain electrode) of the current control TFT 612. Note that an insulator 614 is formed to cover the edge portion of the anode 613. Further, for the insulator 614, either a negative type photosensitive material which becomes insoluble in an etchant by light or a positive type photosensitive material which becomes soluble in an etchant by light can be used. Without limitation to an organic compound, an inorganic compound such as silicon oxide or silicon oxynitride can be used.

Preferably, an upper edge portion or a lower edge portion of the insulator 614 is a curved surface having a specific curvature radius. The curved surface contributes to improvement of coverage by a film which is to be formed over the insulator 614. For example, when a positive type photosensitive acrylic resin is used as a material for the insulator 614, the upper edge portion thereof is preferably formed as a curved surface having a curvature radius of 0.2 μm to 3 μm.

Over the anode 613, an EL layer 615 and a cathode 616 are stacked. Here, by employing an ITO film as the anode 613 and employing a stack of a titanium nitride film and a film including aluminum as the main component or of a titanium nitride film, a film including aluminum as the main component, and a titanium nitride film as a wiring of the current control TFT 612 which is connected to the anode 613, favorable ohmic contact with the ITO film can be obtained and resistance of the wiring can be kept low. Note that, although not illustrated in FIGS. 6A and 6B, the cathode 616 is electrically connected to the FPC 608 which is an external input terminal.

Note that in the EL layer 615, at least a light-emitting layer is provided, and in addition to the light-emitting layer, a hole-injection layer, a hole-transport layer, an electron-transport layer, an electron-injection layer, and/or the like may be provided. The anode 613, the EL layer 615, and the cathode 616 are stacked to form a light-emitting element 617.

In addition, although one light-emitting element 617 is illustrated in the cross-sectional view in FIG. 6B, a plurality of light-emitting elements are arranged in matrix in the pixel portion 602. Note that full-color display can be achieved by providing light-emitting elements that emit light of three colors (R, G, and B) as selected in the pixel portion 602. Color filters may be used in combination to perform full-color display.

The light-emitting element 617 is provided in a space 618 surrounded by the element substrate 601, the sealing substrate 606, and the sealant 605. Note that the space 618 may be filled with an inert gas (nitrogen, argon, or the like) or any other material such as the sealant 605.

As a material for the sealant 605, an epoxy resin is preferably used. It is desirable to use a material that allows permeation of moisture or oxygen as little as possible. As a material for the element substrate 601 or the sealing substrate 606, a plastic substrate formed of fiberglass-reinforced plastics (FRP), polyvinyl fluoride (PVF), polyester, acrylic, or the like can be used besides a glass substrate or a quartz substrate.

Note that the structure described in this embodiment can be combined as appropriate with any of the structures described in the other embodiments.

Embodiment 6

In this embodiment, examples of various electronic devices and lighting devices, which are completed using light-emitting devices of an embodiment of the present invention, will be described with reference to FIGS. 7A to 7E and FIG. 8.

Examples of the electronic devices to which a light-emitting device is applied include television sets (also referred to as televisions or television receivers), monitors of computers or the like, cameras such as digital cameras or digital video cameras, digital photo frames, cellular phones (also referred to as cell phones or cellular phone sets), portable game machines, portable information terminals, audio reproducing devices, large-sized game machines such as pachinko machines, and the like. Specific examples of these electronic devices and lighting devices are illustrated in FIGS. 7A to 7E.

Figure 7A:
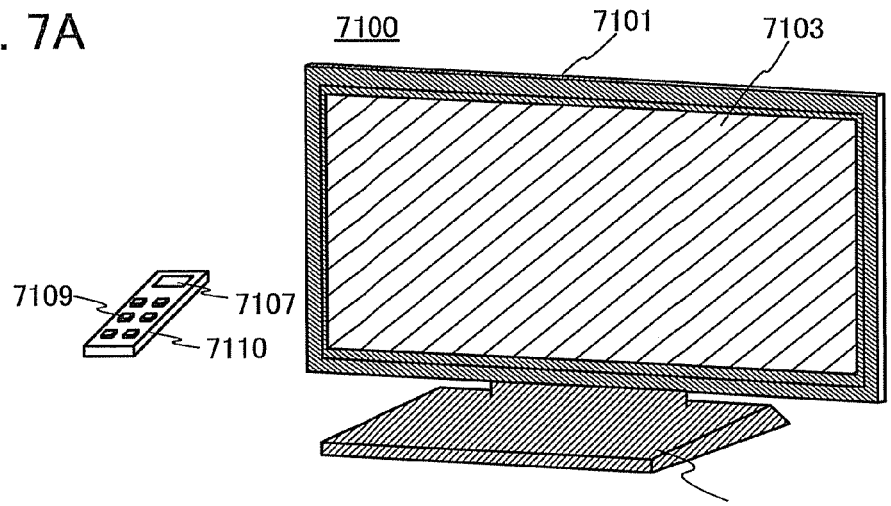
FIGS. 7A to 7E each illustrate an electronic device.

FIG. 7A illustrates an example of a television device 7100. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 7B:
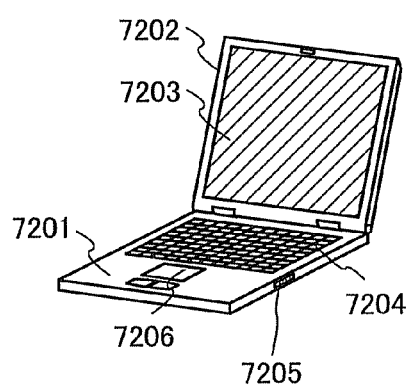

FIG. 7B illustrates an example of a computer. This computer includes a main body 7201, a housing 7202, a display portion 7203, a keyboard 7204, an external connecting port 7205, a pointing device 7206, and the like. This computer is manufactured by using a light-emitting device in the display portion 7203.

Figure 7C:
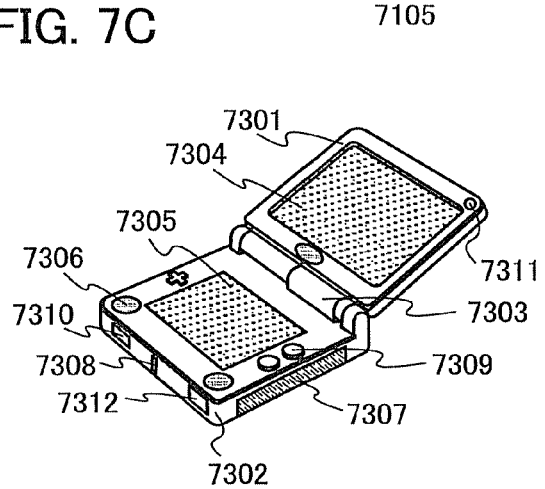

FIG. 7C illustrates an example of a portable game machine. This portable amusement machine includes two housings: a housing 7301 and a housing 7302. The housings 7301 and 7302 are connected with a connection portion 7303 that the portable game machine can be opened or folded. A display portion 7304 and a display portion 7305 are incorporated in the housing 7301 and the housing 7302, respectively. In addition, the portable game machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone 7312, and the like. It is needless to say that the structure of the portable game machine is not limited to the above as long as the light-emitting device is used for at least either the display portion 7304 or the display portion 7305, or both. The portable game machine illustrated in FIG. 7C has a function of reading a program or data stored in a recording medium to display it on the display portion, and a function of sharing information with another portable game machine by wireless communication. The portable game machine illustrated in FIG. 7C can have a variety of functions without limitation to the above.

Figure 7D:
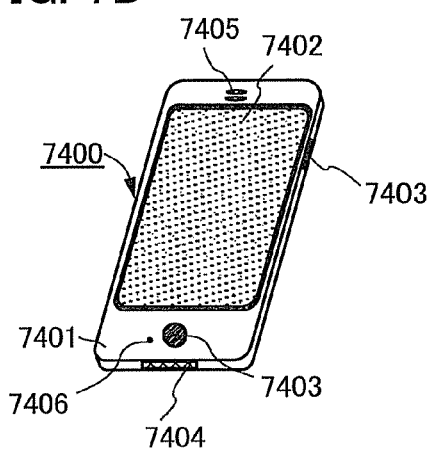

FIG. 7D illustrates an example of a cellular phone. The cellular phone 7400 is provided with a display portion 7402 incorporated in a housing 7401, operation buttons 7403, an external connection port 7404, a speaker 7405, a microphone 7406, and the like. Note that the light-emitting device is used for the display portion 7402 of the cellular phone 7400.

When the display portion 7402 of the cellular phone 7400 illustrated in FIG. 7D is touched with a finger or the like, data can be input into the cellular phone 7400. Furthermore, operations such as making calls and composing mails can be performed by touching the display portion 7402 with a finger or the like.

There are mainly three screen (image) modes for the display portion 7402. The first mode is a display mode mainly for displaying images. The second mode is an input mode mainly for inputting data such as text. The third mode is a display-and-input mode which is a combination of the two modes, that is, a combination of the display mode and the input mode.

For example, in the case of making a call or texting, a text input mode (a second mode) mainly for inputting text is selected for the display portion 7402 so that characters displayed on a screen can be inputted. In that case, it is preferable to display a keyboard or number buttons on the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone 7400 is placed horizontally or vertically for a landscape mode or a portrait mode).

The screen modes are changed by touching the display portion 7402 or using the operation buttons 7403 of the housing 7401. Alternatively, the screen modes may be changed depending on the kind of the image displayed on the display portion 7402. For example, when a signal of an image displayed on the display portion is the one of moving image data, the screen mode is changed to the display mode (a first mode). When the signal is the one of text data, the screen mode is changed to the input mode (the second mode).

When an input by touching the display portion 7402 is not performed for a certain period, the screen mode may be controlled so as to be changed from the input mode (the second mode) to the display mode (the first mode).

The display portion 7402 may function as an image sensor. For example, an image of a palm print, a fingerprint, or the like is taken when the display portion 7402 is touched with a palm or a finger, whereby personal identification can be performed. Further, by providing a backlight or a sensing light source which emits a near-infrared light in the display portion, an image of a finger vein, a palm vein, or the like can be taken.

Figure 7E:
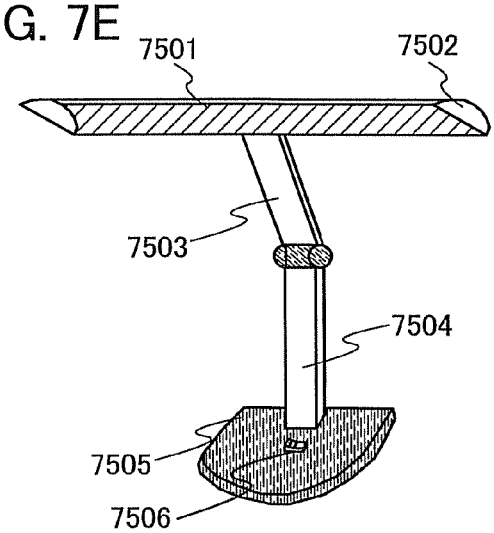

FIG. 7E illustrates a desk lamp, which includes a lighting portion 7501, a shade 7502, an adjustable arm 7503, a support 7504, a base 7505, and a power supply 7506. The desk lamp is manufactured using a light-emitting device for the lighting portion 7501. Note that a lamp includes a ceiling light, a wall light, and the like in its category.

Figure 8:
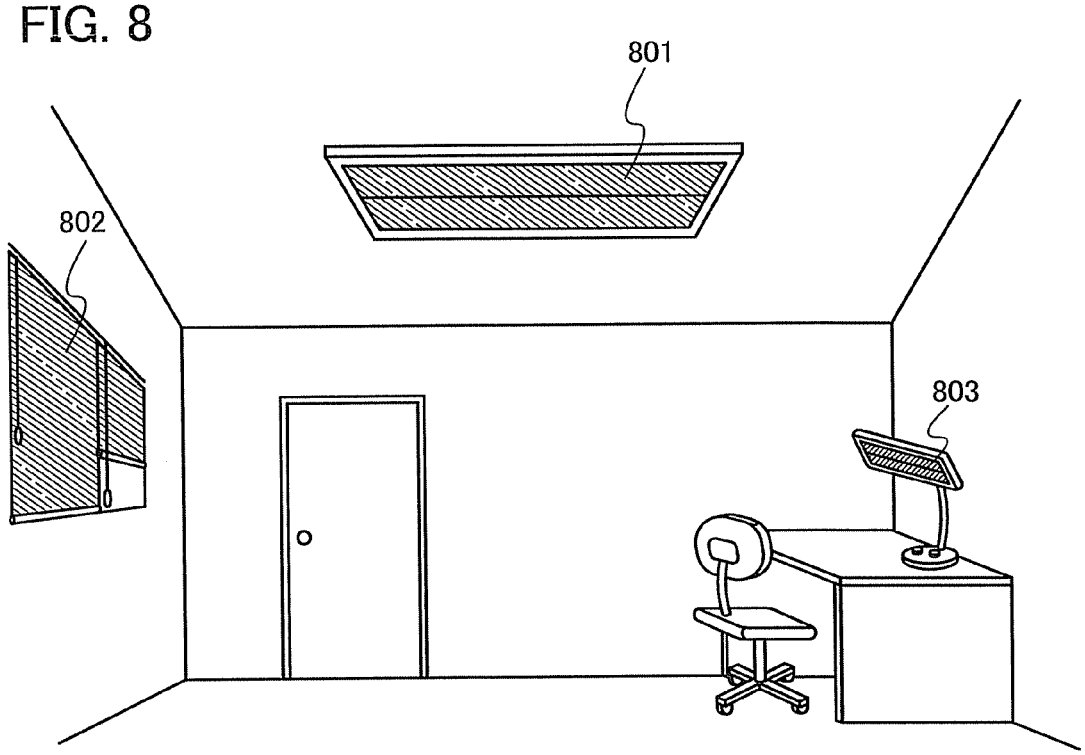
FIG. 8 illustrates lighting devices.

FIG. 8 illustrates an example in which the light-emitting device is used for an interior lighting device 801. The light-emitting device enables an increase in emission area, and therefore can be used as a large-sized lighting device. Furthermore, the light-emitting device may be used as a lighting device 802 which can be rolled up. In addition, a desk lamp 803 as illustrated in FIG. 7E may also be used in the room provided with the interior lighting device 801.

Electronic devices, lighting devices, and the like as described above can be provided by application of the light-emitting device described in the above embodiment, for example. Thus, the applicable range of the light-emitting device is wide so that the light-emitting device can be applied to electronic devices in a variety of fields.

Note that the structure described in this embodiment can be combined with a structure described in any of the other embodiments, as appropriate.

EXAMPLE 1

In this example, a method for synthesizing N,N'-(quinoxaline-2,3-diyldi-4,1-phenylene)bis{N-[4-(9H-carbazol-9-yl)phenyl]quinolin-8-amine} (abbreviation: YGQPQ), which is the quinoxaline derivative represented by Structural Formula (100), is specifically described.

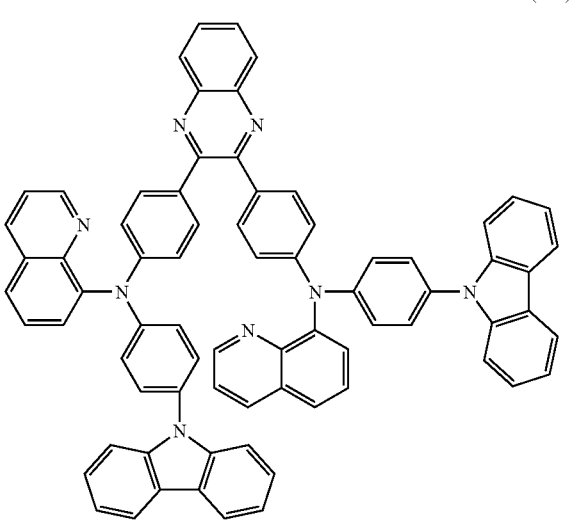

(100)

The reaction scheme of N,N'-(quinoxaline-2,3-diyldi-4,1-phenylene)bis{N-[4-(9H-carbazol-9-yl)phenyl]quinolin-8-amine} (abbreviation: YGQPQ) is shown in (C-1).

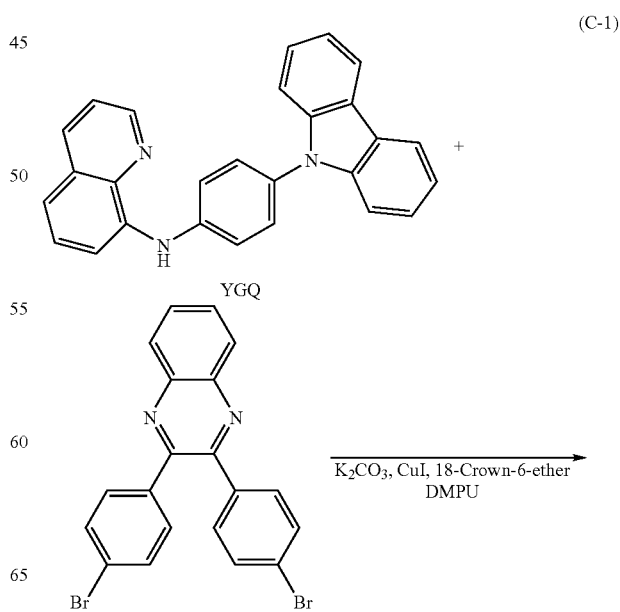

(C-1)

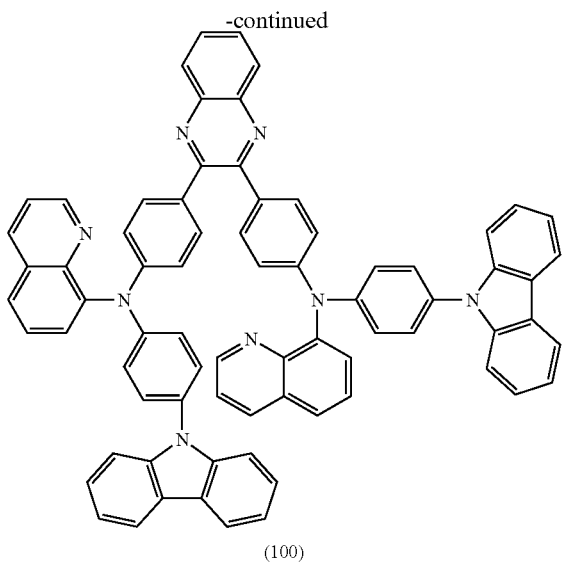

(100)

In a 50 mL three-necked flask were placed 1.2 g (3.2 mmol) of N-[4-(9H-carbazol-9-yl)phenyl]quinolin-8-amine (abbreviation: YGQ), 0.70 g (1.6 mmol) of 2,3-bis(4-bromophenyl)quinoxaline, 0.83 g (6.0 mmol) of potassium carbonate, 0.045 g (0.24 mmol) of copper iodide, and 0.050 g (0.19 mmol) of 18-crown-6-ether. After the mixture was degassed under reduced pressure, the air in the flask was replaced with nitrogen. To the mixture was added 5 mL of 1,3-dimethyl-3,4,5,6-tetrahydro-2(1H)-pyrimidinone (abbreviation: DMPU), and then the mixture was stirred at 180° C. for 5 hours under a nitrogen stream.

After the stirring, toluene was added to the mixture, and the suspension was subjected to suction filtration through Celite (manufactured by Wako Pure Chemical Industries, Ltd., Catalog No. 531-16855), alumina, and Florisil (manufactured by Wako Pure Chemical Industries, Ltd., Catalog No. 540-00135) to obtain a filtrate. The filtrate obtained was washed with water, and then an organic layer was dried with magnesium sulfate. After the drying, the mixture was subjected to suction filtration to obtain a filtrate. The compound obtained by concentration of the filtrate was recrystallized with a mixed solvent of chloroform and hexane, and 1.0 g of a powdery yellow solid, which was the desired substance, was obtained in a yield of 95%.

By a nuclear magnetic resonance (NMR), it has been confirmed that this compound is N,N'-(quinoxaline-2,3-diyldi-4,1-phenylene)bis{N-[4-(9H-carbazol-9-yl)phenyl]quinolin-8-amine} (abbreviation: YGQPQ) which is the desired substance.

The $^1$H NMR data of the obtained compound are shown below.

$^1$H NMR (CDCl$_3$, 300 MHz): δ=7.11 (d, J=9.8 Hz, 4H), 7.20-7.73 (m, 36H), 8.03-8.15 (m, 8H)

Figure 10A:
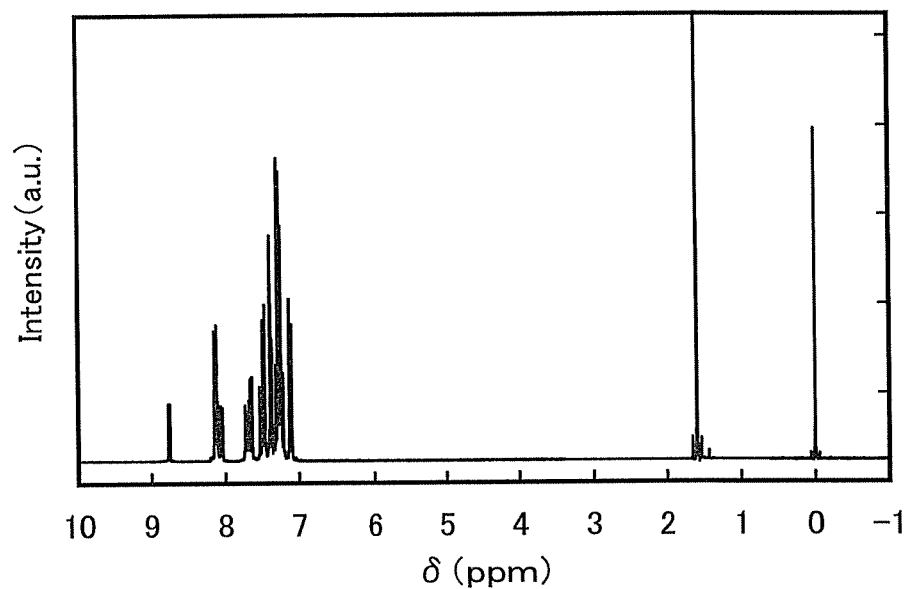
FIGS. 10A and 10B are NMR charts of YGQPQ (abbreviation).
Figure 10B:
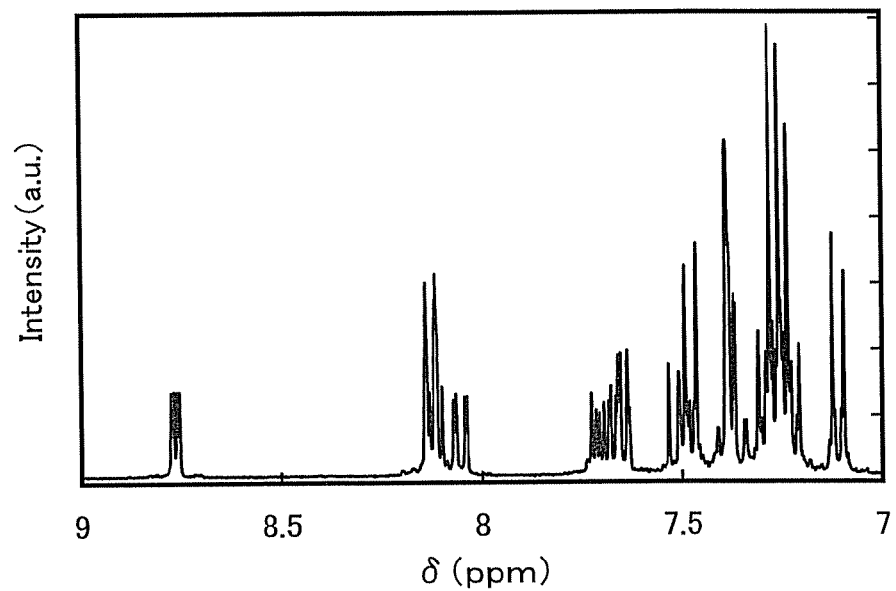

In addition, a $^1$H-NMR chart is shown in FIGS. 10A and 10B. Note that FIG. 10B is an enlarged chart of FIG. 10A in the range of 7.0 ppm to 9.0 ppm.

In addition, YGQPQ obtained as above was subjected to thermogravimetry-differential thermal analysis (TG-DTA). The measurement with a thermogravimetry-differential thermal analyzer (TG/DTA 320, manufactured by Seiko Instruments Inc.) under the atmospheric pressure from room temperature to 500° C. shows no decrease in weight. Further, the glass transition temperature of YGQPQ was measured with a differential scanning calorimeter (Pyris 1 DSC, manufactured by Perkin Elmer Co., Ltd.) and was found to be 145° C. These results indicate that YGQPQ is a material which has favorable heat resistance.

Figure 11A:
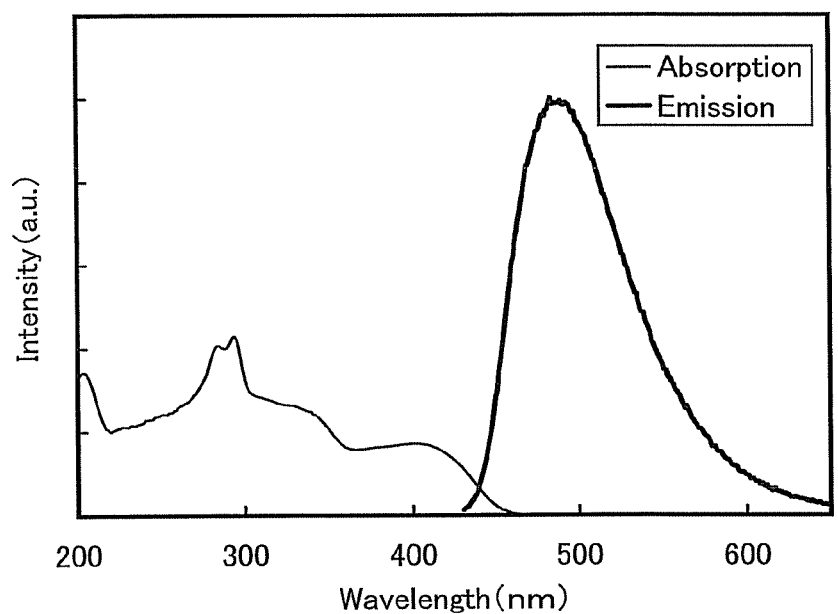
FIGS. 11A and 11B are graphs showing an absorption spectrum and an emission spectrum of YGQPQ (abbreviation).
Figure 11B:
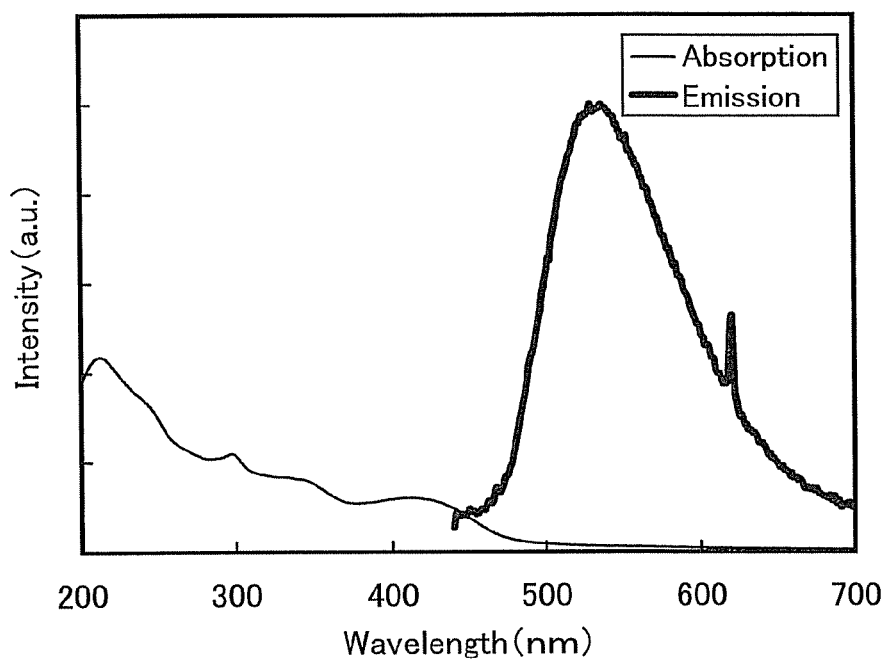

FIG. 11A shows an absorption spectrum and an emission spectrum of a toluene solution of YGQPQ. FIG. 11B shows an absorption spectrum and an emission spectrum of a thin film of YGQPQ. An ultraviolet-visible spectrophotometer (V-550, manufactured by JASCO Corporation) was used for the measurement of the absorption spectra. Samples were prepared with the solution put in a quartz cell and the thin film evaporated to a quartz substrate, which were measured. FIGS. 11A and 11B show the absorption spectrum of the solution and the absorption spectrum of the thin film from which the absorption spectrum of toluene alone in a quartz cell and the absorption spectrum of a quartz substrate have been subtracted, respectively. In FIGS. 11A and 11B, the horizontal axis indicates the wavelength (nm) and the vertical axis indicates the intensity (arbitrary unit). In the case of the toluene solution, absorption is observed at about 403 nm, and the maximum emission wavelength is 490 nm (excitation wavelength: 408 nm). In the case of the thin film, absorption is observed at about 409 nm, and the maximum emission wavelength is 536 nm (excitation wavelength: 412 nm).

Furthermore, the HOMO level and LUMO level of a thin film of YGQPQ were measured. The value of the HOMO level was obtained by converting the value of the ionization potential measured with a photoelectron spectrometer (AC-2, manufactured by Riken Keiki Co., Ltd.) in the air atmosphere into a negative value. In addition, the value of the LUMO level was obtained in such a manner that the absorption edge was obtained from Tauc plot, with an assumption of direct transition, using data about the absorption spectrum of the thin film of YGQPQ which is shown in FIG. 11B, and the absorption edge was added as an optical energy gap to the value of the HOMO level. The results show that the HOMO level, energy gap, and LUMO level of YGQPQ are −5.49 eV, 2.66 eV, and −2.83 eV, respectively.

In addition, the optimal molecular structure of YGQPQ in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable high-speed, high-accuracy calculations. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of is to 3s are considered in the case of hydrogen atoms, while orbits of 1s to 4s and 2p to 4p are considered in the case of carbon atoms. Furthermore, to improve calculation accuracy, the p function and the d function as polarization basis sets were added respectively to hydrogen atoms and atoms other than hydrogen atoms.

Note that Gaussian 03 was used as a quantum chemistry computational program. A high performance computer (Altix 4700, manufactured by SGI Japan, Ltd.) was used for the calculations.

Figure 16A:
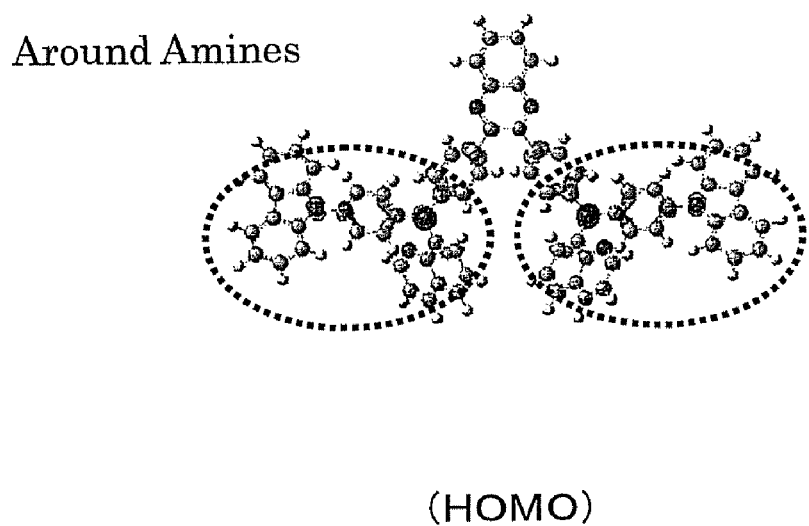
FIGS. 16A and 16B show the highest occupied molecular orbital (HOMO) and lowest unoccupied molecular orbital (LUMO) of YGQPQ, respectively.
Figure 16B:
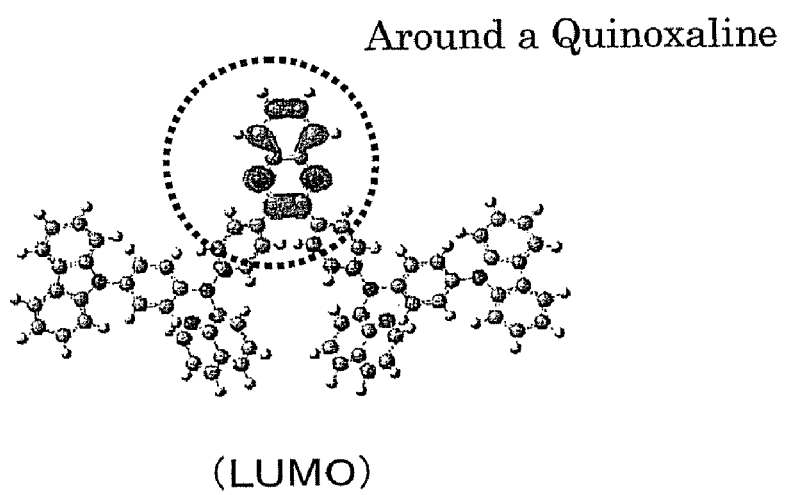

FIGS. 16A and 16B show the highest occupied molecular orbital (HOMO) and lowest unoccupied molecular orbital (LUMO) in the optimal molecular structure of YGQPQ which are obtained by calculation and visualized with GaussView 4.1. FIG. 16A shows the highest occupied molecular orbital (HOMO), and FIG. 16B shows the lowest unoccupied molecular orbital (LUMO). In the drawings, the spheres represent atoms which form YGQPQ and cloud-like objects around atoms represent the highest occupied molecular orbital (HOMO) or lowest unoccupied molecular orbital (LUMO).

It can be seen from FIGS. 16A and 16B that there are the highest occupied molecular orbitals around amines in YGQPQ and that amino groups significantly contribute to the hole-transporting property of YGQPQ. In addition, the existence of the lowest unoccupied molecular orbital around a quinoxaline shows that a quinoxalyl group significantly contributes to the electron-transporting property of YGQPQ. Accordingly, it is found that YGQPQ is a bipolar material having electron and hole-transporting properties because a quinoxaline skeleton which is a heteroaromatic ring having the electron-transporting property and amine skeletons having the hole-transporting property are introduced in a molecule.

EXAMPLE 2

In this example, a method for manufacturing a light-emitting element including any of the quinoxaline derivatives described in Embodiment 1 as a host material in a light-emitting layer and the results of measurement of element characteristics are described. Specifically, Light-Emitting Element 1 formed using N,N'-(quinoxaline-2,3-diyldi-4,1-phenylene)bis{N-[4-(9H-carbazol-9-yl)phenyl]quinolin-8-amine} (abbreviation: YGQPQ), which is described in Example 1, is described.

Figure 9:
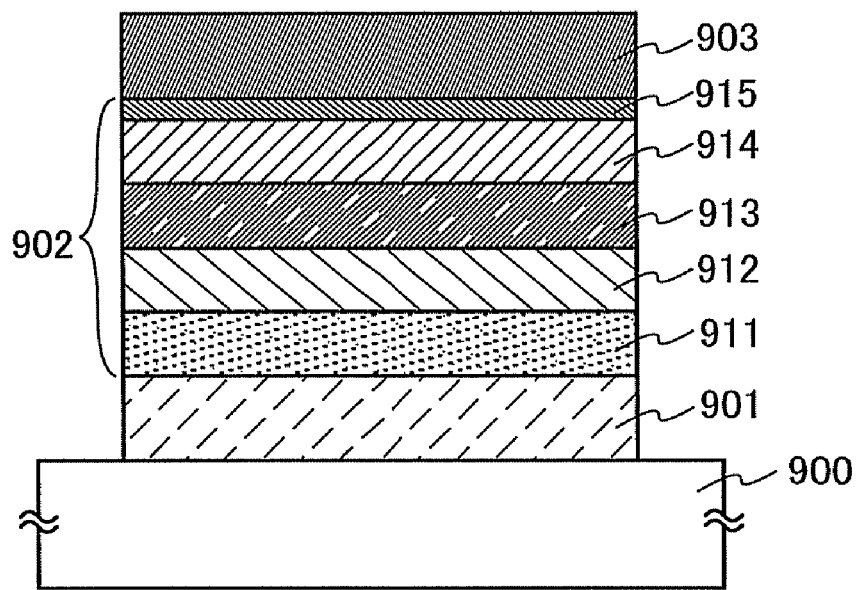
FIG. 9 illustrates a light-emitting element.

Note that the light-emitting element of this example has a structure illustrated in FIG. 9, in which a third layer 913 which is a light-emitting layer is formed using one of the above-described quinoxaline derivatives. Structural formulae of organic compounds used in this example are shown below.

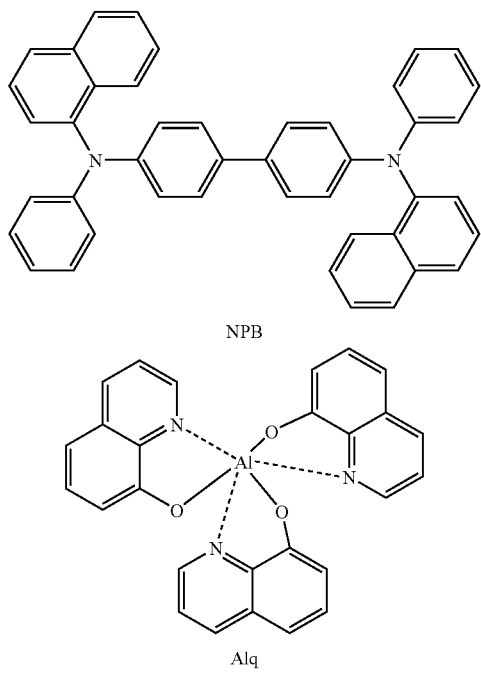

NPB

Alq

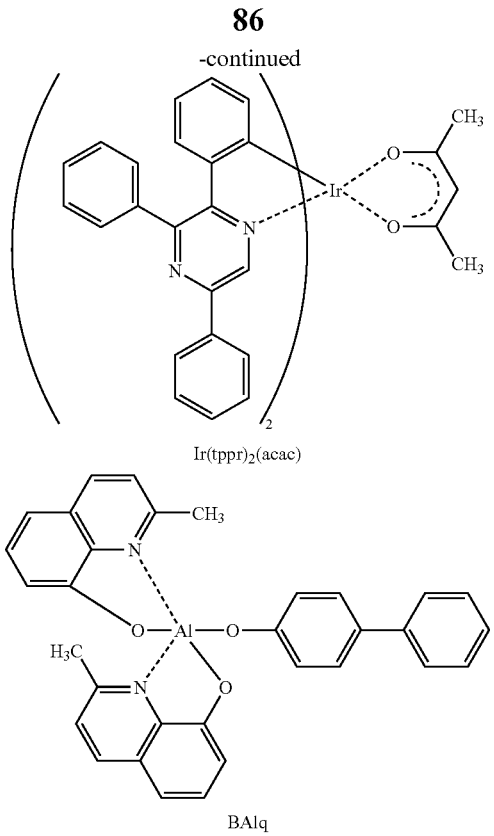

Ir(tppr)$_2$(acac)

BAlq (Light-Emitting Element 1)

First, indium oxide-tin oxide containing silicon oxide was deposited to a substrate 900 which was a glass substrate by a sputtering method to form a first electrode 901. Note that the thickness was 110 nm and the electrode area was 2 mm×2 mm.

Next, an EL layer 902 including a stack of a plurality of layers was formed over the first electrode 901. In this example, the EL layer 902 has a structure in which a first layer 911 which is a hole-injection layer, a second layer 912 which is a hole-transport layer, the third layer 913 which is a light-emitting layer, a fourth layer 914 which is an electron-transport layer, and a fifth layer 915 which is an electron-injection layer are stacked in that order.

The substrate 900 provided with the first electrode 901 was fixed to a substrate holder that was provided in a vacuum evaporation apparatus so that a surface on which the first electrode 901 was formed faced downward. The pressure in the vacuum evaporation apparatus was reduced to about $10^{-4}$ Pa. Then, on the first electrode 901, 4,4'-bis[N-(1-naphthyl)-N-phenylamino]biphenyl (abbreviation: NPB) and molybdenum(VI) oxide were co-evaporated to form the first layer 911 which was a hole-injection layer. The thickness of the first layer 911 was set to 50 nm, and the evaporation rate was controlled so that the weight ratio of NPB to molybdenum (VI) oxide was 4:1 (=NPB:molybdenum oxide). Note that the co-evaporation method refers to an evaporation method by which evaporation is performed from a plurality of evaporation sources in one treatment chamber simultaneously.

Next, a 10-nm-thick film of a hole-transport material was formed on the first layer 911 by an evaporation method with resistance heating to form the second layer 912 which was a hole-transport layer. Note that 4,4'-bis[N-(1-naphthyl)-N-phenylamino]biphenyl (abbreviation: NPB) was used for the second layer 912.

Next, the third layer 913 which was a light-emitting layer was formed on the second layer 912 by an evaporation method with resistance heating. As the third layer 913 of Light-Emitting Element 1, N,N'-(quinoxaline-2,3-diyldi-4,1-phenylene)bis{N-[4-(9H-carbazol-9-yl)phenyl]quinolin-8-amine} (abbreviation: YGQPQ) and (acetylacetonato)bis(2,3,5-triphenylpyridinato)iridium(III) (abbreviation: Ir(tppr)$_2$(acac)) were co-evaporated to a thickness of 40 nm. Here, the evaporation rate was controlled so that the weight ratio of YGQPQ to Ir(tppr)$_2$(acac) was 1:0.06 (=YGQPQ:Ir(tppr)$_2$(acac)).

Furthermore, on the third layer 913, a 10-nm-thick film of bis(2-methyl-8-quinolinolato)(4-phenylphenolato)aluminum (abbreviation: BAlq) and, thereon, a 20-nm-thick film of bathophenanthroline (abbreviation: BPhen) were formed by an evaporation method with resistive heating to form the fourth layer 914 which was an electron-transport layer.

On the fourth layer 914, tris(8-quinolinolato)aluminum (abbreviation: Alq) and lithium were co-evaporated to a thickness of 50 nm as the fifth layer 915 which was an electron-injection layer. Here, the evaporation rate was controlled so that the weight ratio of Alq to lithium was 1:0.01 (=Alq:lithium).

Lastly, a 200-nm-thick film of aluminum was formed by an evaporation method with resistance heating to form the second electrode 903. In this manner, Light-Emitting Element 1 was manufactured.

(Comparative Light-Emitting Element 2)

Comparative Light-Emitting Element 2 was manufactured in a manner similar to that of Light-Emitting Element 1 except for a light-emitting layer. A method for manufacturing the light-emitting layer of Comparative Light-Emitting Element 2 will be hereinafter described.

The third layer 913 which was a light-emitting layer was formed on the second layer 912 by an evaporation method with resistance heating. As the third layer 913 of Comparative Light-Emitting Element 2, N,N'-(quinoxaline-2,3-diyldi-4,1-phenylene)bis{N-[4-(9H-carbazol-9-yl)phenyl]benzene-8-amine} (abbreviation: YGAPQ) and (acetylacetonato)bis(2,3,5-triphenylpyridinato)iridium(III) (abbreviation: Ir(tppr)$_2$(acac)) were co-evaporated to a thickness of 40 nm. Here, the evaporation rate was controlled so that the weight ratio of YGAPQ to Ir(tppr)$_2$(acac) was 1:0.06 (=YGAPQ:Ir(tppr)$_2$(acac)).

Note that YGAPQ (abbreviation) used for Comparative Light-Emitting Element 2 is represented by Structural Formula (300).

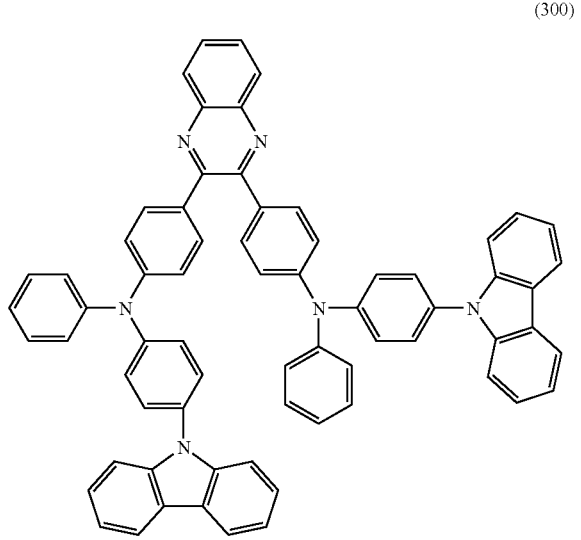

(300)

Light-Emitting Element 1 and Comparative Light-Emitting Element 2 obtained in the above manner were sealed in a glove box containing a nitrogen atmosphere so as not to be exposed to air. Then, operation characteristics of these light-emitting elements were measured. Note that the measurement was carried out at room temperature (in an atmosphere kept at 25° C.).

Figure 12:
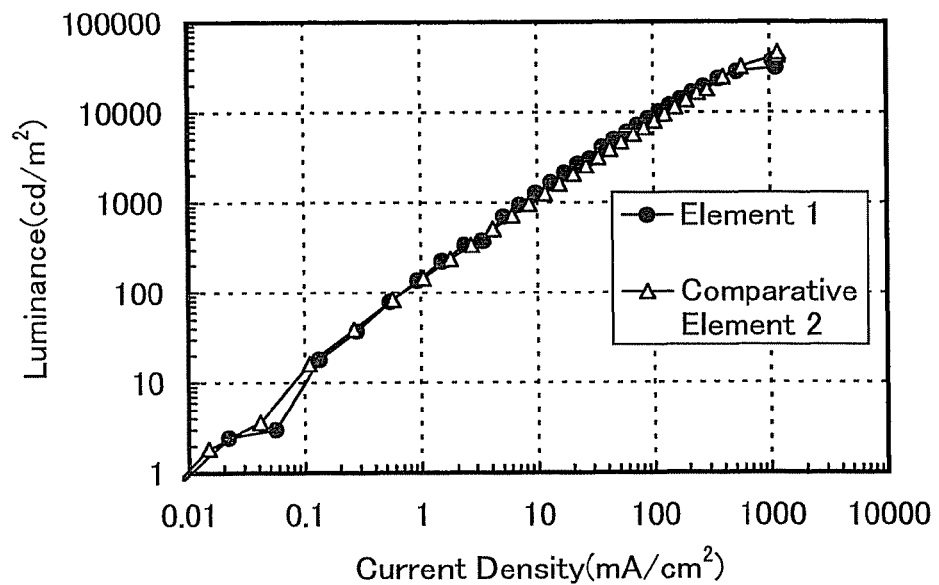
FIG. 12 shows current density-luminance characteristics of Light-Emitting Element 1 and Comparative Light-Emitting Element 2.
Figure 13:
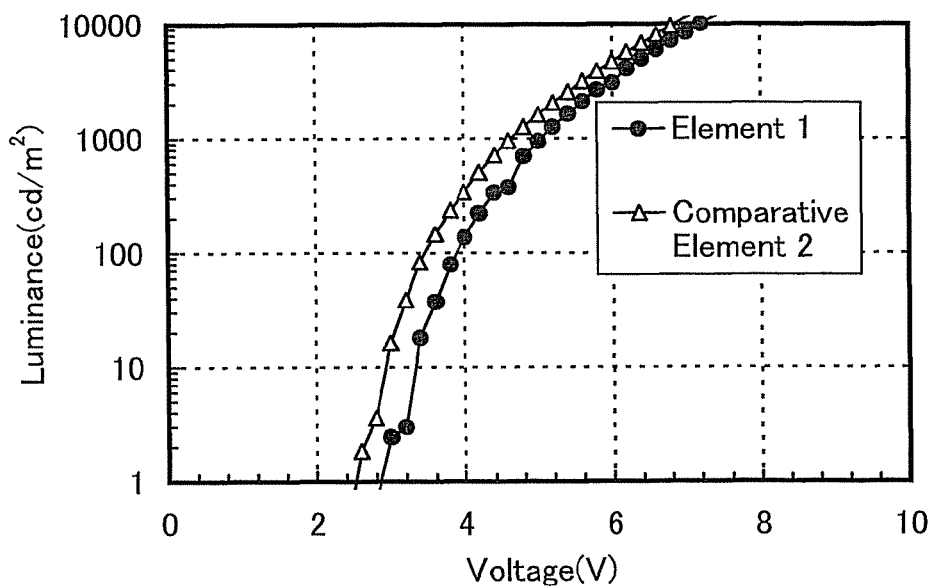
FIG. 13 shows voltage-luminance characteristics of Light-Emitting Element 1 and Comparative Light-Emitting Element 2.
Figure 14:
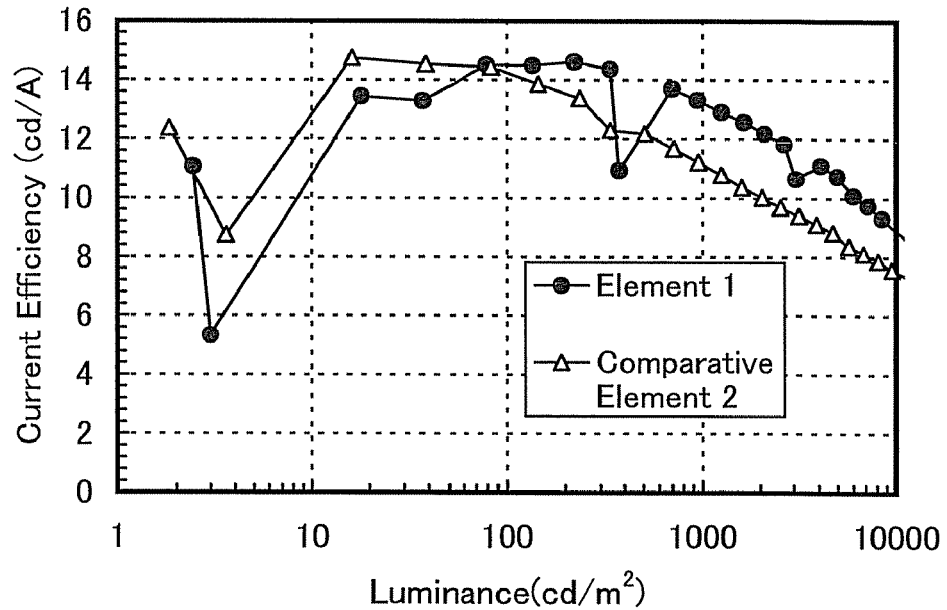
FIG. 14 shows luminance-current efficiency characteristics of Light-Emitting Element 1 and Comparative Light-Emitting Element 2.
Figure 15:
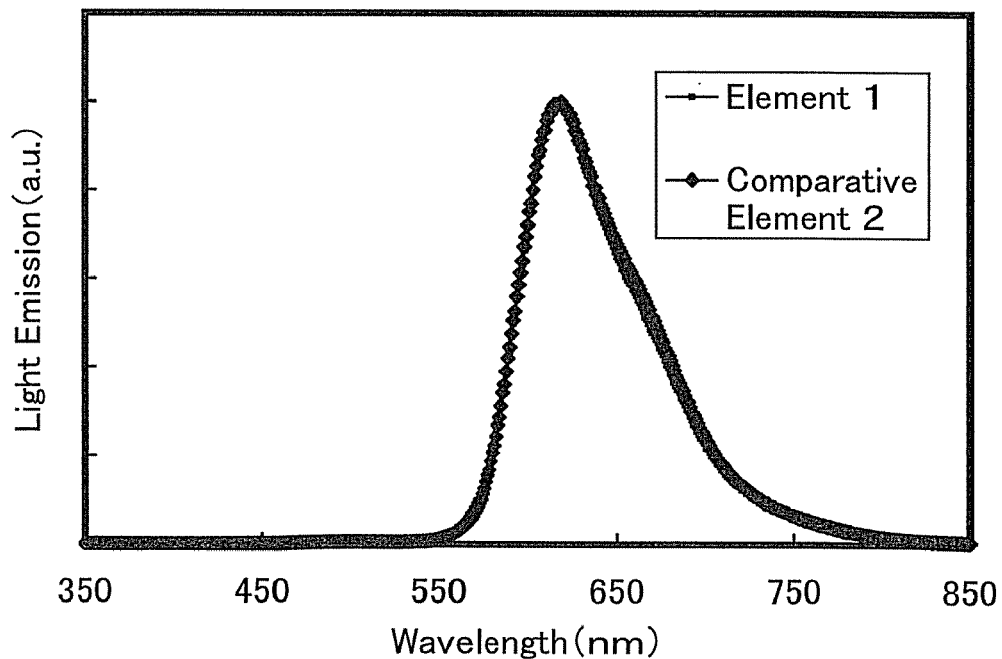
FIG. 15 shows emission spectra of Light-Emitting Element 1 and Comparative Light-Emitting Element 2.

FIG. 12 shows current density-luminance characteristics of Light-Emitting Element 1 and Comparative Light-Emitting Element 2. FIG. 13 shows voltage-luminance characteristics thereof. FIG. 14 shows luminance-current efficiency characteristics thereof. FIG. 15 shows emission spectra obtained at a current of 1 mA. FIG. 15 shows that light emissions of Light-Emitting Element 1 and Comparative Light-Emitting Element are light emissions from Ir(tppr)$_2$(acac).

In Light-Emitting Element 1, the CIE chromaticity coordinates were (x=0.66, y=0.34) at a luminance of 947 cd/m$^2$, and red light emission was obtained. The current efficiency was 13.3 cd/A at a luminance of 947 cd/m$^2$. In addition, the voltage was 5.0 V at a luminance of 974 cd/m$^2$.

On the other hand, in Comparative Light-Emitting Element 2, the CIE chromaticity coordinates were (x=0.66, y=0.34) at a luminance of 954 cd/m$^2$, and red light emission was obtained. The current efficiency was 11.2 cd/A at a luminance of 954 cd/m$^2$. In addition, the voltage was 7.8 V at a luminance of 970 cd/m$^2$.

This shows that Light-Emitting Element 1 has higher current efficiency and external quantum efficiency than Comparative Light-Emitting Element 2. Thus, by using the quinoxaline derivative of an embodiment of the present invention, a highly efficient light-emitting element can be obtained.

This application is based on Japanese Patent Application serial no. 2009-085977 filed with Japan Patent Office on Mar. 31, 2009, the entire contents of which are hereby incorporated by reference.

What is claimed is:

1. A quinoxaline derivative represented by General Formula (G1):

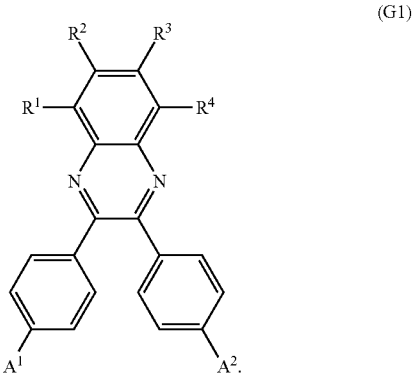

(G1)

wherein R$^1$ to R$^4$ each independently represent hydrogen, an alkyl group having 1 to 4 carbon atoms, or an aryl group having 6 to 10 carbon atoms in a ring, wherein A$^1$ and A$^2$ each independently represent a hydrogen atom, an alkyl group having 1 to 4 carbon atoms, an aryl group having 6 to 10 carbon atoms in a ring, or a substituent represented by General Formula (A1), wherein at least one of A$^1$ and A$^2$ is the substituent represented by General Formula (A1):

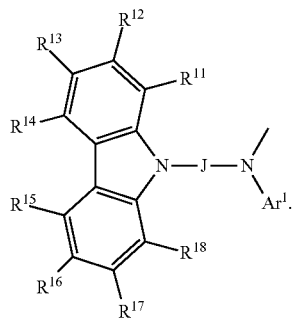

(A1)

wherein Ar¹ represents a quinolyl group, wherein $R^{11}$ to $R^{18}$ each independently represent a hydrogen atom, an alkyl group having 1 to 4 carbon atoms, or a substituted or unsubstituted aryl group having 6 to 10 carbon atoms in a ring, and wherein J represents a substituted or unsubstituted arylene group having 6 to 12 carbon atoms.

2. The quinoxaline derivative according to claim 1, wherein $R^1$ to $R^4$ represent hydrogen.

3. The quinoxaline derivative according to claim 1, wherein $R^1$ to $R^4$ represent hydrogen, wherein $A^1$ and $A^2$ each independently represent a hydrogen atom, an alkyl group having 1 to 4 carbon atoms, an aryl group having 6 to 10 carbon atoms in a ring, or a substituent represented by General Formula (A3), wherein at least one of $A^1$ and $A^2$ has the substituent represented by General Formula (A3):

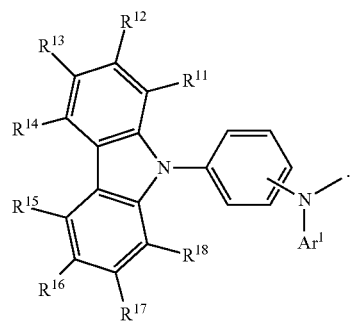

(A3)

wherein Ar¹ represents a quinolyl group, and wherein $R^{11}$ to $R^{18}$ each independently represent a hydrogen atom, an alkyl group having 1 to 4 carbon atoms, or a substituted or unsubstituted aryl group having 6 to 10 carbon atoms in a ring.

4. The quinoxaline derivative according to claim 1, wherein $R^1$ to $R^4$ represent hydrogen, wherein $A^1$ and $A^2$ each independently represent a hydrogen atom, an alkyl group having 1 to 4 carbon atoms, an aryl group having 6 to 10 carbon atoms in a ring, or a substituent represented by General Formula (A4), and wherein at least one of $A^1$ and $A^2$ has the substituent represented by General Formula (A4):

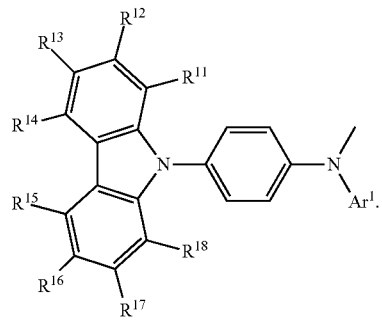

(A4)

wherein Ar¹ represents a quinolyl group, and wherein $R^{11}$ to $R^{18}$ each independently represent a hydrogen atom, an alkyl group having 1 to 4 carbon atoms, or a substituted or unsubstituted aryl group having 6 to 10 carbon atoms in a ring.

5. The quinoxaline derivative according to claim 4, wherein $R^{11}$ to $R^{18}$ each represent a hydrogen atom.

6. A light-emitting device having a light-emitting element, the light-emitting element comprising:
a pair of electrodes; and
a quinoxaline derivative provided between the pair of electrodes, the quinoxaline derivative being represented by General Formula (G1):

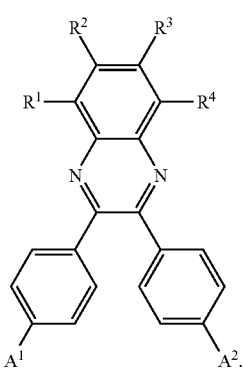

(G1)

wherein $R^1$ to $R^4$ each independently represent hydrogen, an alkyl group having 1 to 4 carbon atoms, or an aryl group having 6 to 10 carbon atoms in a ring, wherein $A^1$ and $A^2$ each independently represent a hydrogen atom, an alkyl group having 1 to 4 carbon atoms, an aryl group having 6 to 10 carbon atoms in a ring, or a substituent represented by General Formula (A1), wherein at least one of $A^1$ and $A^2$ has the substituent represented by General Formula (A1):

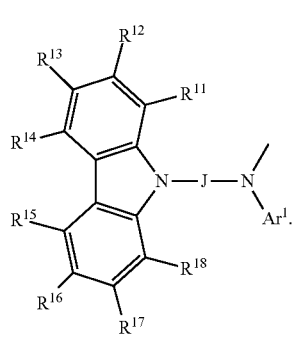

(A1)

wherein Ar$^1$ represents a quinolyl group, wherein R$^{11}$ to R$^{18}$ each independently represent a hydrogen atom, an alkyl group having 1 to 4 carbon atoms, or a substituted or unsubstituted aryl group having 6 to 10 carbon atoms in a ring, and wherein J represents a substituted or unsubstituted arylene group having 6 to 12 carbon atoms.

7. The light-emitting device according to claim 6, wherein the light-emitting element comprises a light-emitting layer between the pair of electrodes, and wherein the quinoxaline derivative is included in the light-emitting layer.

8. The light-emitting device according to claim 6, wherein the light-emitting device comprises a light-emitting layer between the pair of electrodes, and wherein the quinoxaline derivative and a substance which provides a fluorescent emission are included in the light-emitting layer.

9. The light-emitting device according to claim 6, wherein the light-emitting device comprises a light-emitting layer between the pair of electrodes, and wherein the quinoxaline derivative and a substance which provides a phosphorescent emission are included in the light-emitting layer.

10. The light-emitting device according to claim 6, wherein the light-emitting device comprises a light-emitting layer between the pair of electrodes, and wherein the quinoxaline derivative is included in a layer which is in contact with the light-emitting layer.

11. The light-emitting device according to claim 6, further comprising a control unit configured to control light emission of the light-emitting element.

12. An electronic device comprising the light-emitting element according to claim 6.

13. A lighting device comprising the light-emitting device according to claim 6.

14. The quinoxaline derivative according to claim 1, wherein the quinolyl group is a 8-qunolinyl group.

15. The quinoxaline derivative according to claim 1, wherein the quinolyl group is a 8-qunolinyl group, and wherein R$^1$ to R$^4$ each represent hydrogen.

16. The quinoxaline derivative according to claim 1, wherein the quinolyl group is a 8-qunolinyl group, and wherein R$^1$ to R$^4$ and R$^{11}$ to R$^{18}$ each represent hydrogen.

17. The quinoxaline derivative according to claim 1, wherein the quinolyl group is a 8-qunolinyl group, wherein R$^1$ to R$^4$ and R$^{11}$ to R$^{18}$ each represent hydrogen, and wherein J is a phenylene group.

* * * * *